US012741964B2

(12) United States Patent
Babich et al.

(10) Patent No.: US 12,741,964 B2
(45) Date of Patent: Sep. 22, 2026

(54) MACROCYCLIC COMPLEXES OF ALPHA-EMITTING RADIONUCLIDES AND THEIR USE IN TARGETED RADIOTHERAPY OF CANCER

(71) Applicant: Cornell University, Ithaca, NY (US)

(72) Inventors: John W. Babich, New York, NY (US); Justin Wilson, Ithaca, NY (US); Nikki Thiele, Brooktondale, NY (US); James Kelly, New York, NY (US); Shashikanth Ponnala, Ithaca, NY (US)

(73) Assignee: Cornell University, Ithaca, NY (US)

( * ) Notice: Subject to any disclaimer, the term of this patent is extended or adjusted under 35 U.S.C. 154(b) by 758 days.

(21) Appl. No.: 17/678,793

(22) Filed: Feb. 23, 2022

(65) Prior Publication Data

US 2022/0177461 A1 Jun. 9, 2022

Related U.S. Application Data

(62) Division of application No. 16/689,856, filed on Nov. 20, 2019, now Pat. No. 11,279,698.

(Continued)

(51) Int. Cl.

*C07D 413/14* (2006.01)
*A61K 51/04* (2006.01)

(Continued)

(52) U.S. Cl.

CPC ........ *C07D 413/14* (2013.01); *A61K 51/0463* (2013.01); *A61K 51/0482* (2013.01);

(Continued)

(58) Field of Classification Search

CPC .............................. A61K 51/04; C07D 413/14

See application file for complete search history.

(56) References Cited

U.S. PATENT DOCUMENTS 5,162,504 A 11/1992 Horoszewicz
5,595,721 A 1/1997 Kaminski et al.

(Continued)

FOREIGN PATENT DOCUMENTS

AU 2018249559 10/2019
CA 3058663 A1 10/2018

(Continued)

OTHER PUBLICATIONS

Nikki Thiele et al. An eighteen-membered macrocyclic ligand for actinium-225 targeted alpha therapy, Angew Chem Int Ed, 56, 14712-14717. (Year: 2017).*

(Continued)

*Primary Examiner* — Michael G. Hartley
*Assistant Examiner* — Jagadishwar R Samala

(74) *Attorney, Agent, or Firm* — Foley & Lardner LLP

(57) ABSTRACT

The present technology provides compounds as well as compositions including such compounds useful in targeted radiotherapy of cancer and/or mammalian tissue overexpressing prostate specific membrane antigen ("PSMA") where the compounds are represented by the following:

(I)

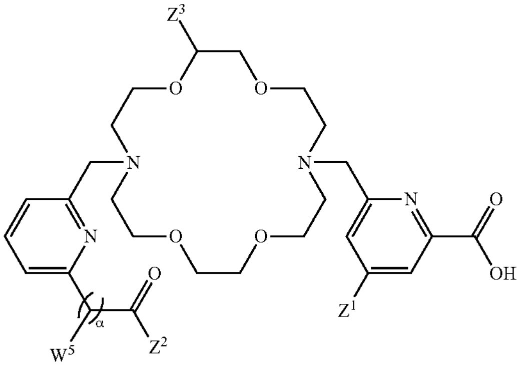

or a pharmaceutically acceptable salt thereof, (IA)

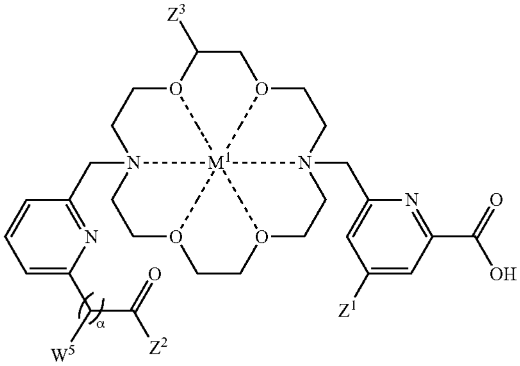

or a pharmaceutically acceptable salt thereof, (Continued)

(II)

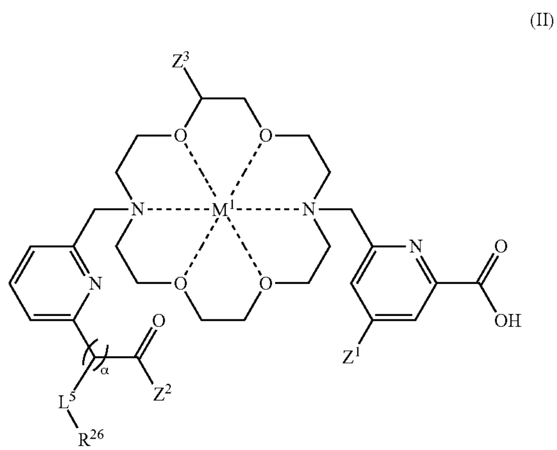

or a pharmaceutically acceptable salt thereof, wherein $M^1$ is independently at each occurrence an alpha-emitting radionuclide. Equivalents of such compounds are also disclosed.

13 Claims, 5 Drawing Sheets

Related U.S. Application Data

(60) Provisional application No. 62/769,989, filed on Nov. 20, 2018, provisional application No. 62/788,700, filed on Jan. 4, 2019, provisional application No. 62/792,835, filed on Jan. 15, 2019.

(51) Int. Cl.
*A61K 51/10* (2006.01)
*A61K 45/06* (2006.01)
*C07B 59/00* (2006.01)

(52) U.S. Cl.
CPC .......... *A61K 51/1072* (2013.01); *A61K 45/06* (2013.01); *C07B 59/002* (2013.01)

(56) References Cited

U.S. PATENT DOCUMENTS

| | | | |
|---|---|---|---|
| 5,736,137 | A | 4/1998 | Anderson et al. |
| 5,773,001 | A | 6/1998 | Hamann et al. |
| 5,776,456 | A | 7/1998 | Anderson et al. |
| 5,821,337 | A | 10/1998 | Carter et al. |
| 5,843,398 | A | 12/1998 | Kaminski et al. |
| 5,846,534 | A | 12/1998 | Waldmann et al. |
| 6,015,542 | A | 1/2000 | Kaminski et al. |
| 6,054,297 | A | 4/2000 | Carter et al. |
| 6,090,365 | A | 7/2000 | Kaminski et al. |
| 6,217,866 | B1 | 4/2001 | Schlessinger et al. |
| 6,235,883 | B1 | 5/2001 | Jakobovits et al. |
| 6,287,537 | B1 | 9/2001 | Kaminski et al. |
| 6,506,883 | B2 | 1/2003 | Meteo de Acosta del Rio et al. |
| 6,565,827 | B1 | 5/2003 | Kaminski et al. |
| 6,569,430 | B1 | 5/2003 | Waldmann et al. |
| 6,602,684 | B1 | 8/2003 | Umana et al. |
| 6,740,522 | B2 | 5/2004 | Anderson |
| 6,984,720 | B1 | 1/2006 | Korman et al. |
| 6,989,145 | B2 | 1/2006 | Shitara et al. |
| 7,070,959 | B1 | 7/2006 | Papadopoulos et al. |
| 7,090,843 | B1 | 8/2006 | Francisco et al. |
| 7,097,840 | B2 | 8/2006 | Erickson et al. |
| 7,112,324 | B1 | 9/2006 | Dorken et al. |
| 7,138,501 | B2 | 11/2006 | Ruben et al. |
| 7,432,357 | B2 | 10/2008 | Gillies |
| 7,498,414 | B2 | 3/2009 | Zhu |
| 7,598,350 | B2 | 10/2009 | Liu et al. |
| 7,612,182 | B2 | 11/2009 | Giles-Komar et al. |
| 7,638,605 | B2 | 12/2009 | Ludwig |
| 7,709,610 | B2 | 5/2010 | Williams et al. |
| 7,829,531 | B2 | 11/2010 | Senter et al. |
| 7,829,673 | B2 | 11/2010 | De Weers et al. |
| 7,862,817 | B2 | 1/2011 | Adams et al. |
| 7,968,093 | B2 | 6/2011 | Ludwig |
| 8,008,449 | B2 | 8/2011 | Korman et al. |
| 8,128,929 | B2 | 3/2012 | Loizos et al. |
| 8,153,768 | B2 | 4/2012 | Kunz et al. |
| 8,217,149 | B2 | 7/2012 | Irving et al. |
| 8,354,509 | B2 | 1/2013 | Carven et al. |
| 8,466,263 | B2 | 6/2013 | Marasco et al. |
| 8,529,902 | B2 | 9/2013 | Teeling et al. |
| 8,663,638 | B2 | 3/2014 | Lindhofer et al. |
| 8,779,108 | B2 | 7/2014 | Queva et al. |
| 8,809,502 | B2 | 8/2014 | Pastan et al. |
| 8,921,528 | B2 | 12/2014 | Holt et al. |
| 9,017,676 | B2 | 4/2015 | Lindhofer |
| 9,624,298 | B2 | 4/2017 | Nostri et al. |
| 9,987,500 | B2 | 6/2018 | Papadopoulos et al. |
| 10,806,806 | B2 | 10/2020 | Babich et al. |
| 11,285,227 | B2 | 3/2022 | Babich et al. |
| 11,400,165 | B2 | 8/2022 | Krantz et al. |
| 11,576,986 | B2 | 2/2023 | Salter et al. |
| 2004/0001835 | A1 | 1/2004 | Woessner et al. |
| 2013/0309234 | A1 | 11/2013 | Lindhofer |
| 2015/0064185 | A1 | 3/2015 | Holt et al. |
| 2017/0326261 | A1 | 11/2017 | Oukhatar et al. |
| 2020/0157087 | A1 | 5/2020 | Babich et al. |
| 2020/0353105 | A1 | 11/2020 | Salter et al. |
| 2021/0121584 | A1 | 4/2021 | Babich et al. |
| 2021/0236667 | A1 | 8/2021 | Fonge et al. |
| 2022/0143228 | A1 | 5/2022 | Ludwig et al. |
| 2022/0143231 | A1 | 5/2022 | Salter et al. |
| 2022/0184217 | A1 | 6/2022 | White et al. |
| 2023/0011134 | A1 | 1/2023 | Salter et al. |
| 2023/0044430 | A1 | 2/2023 | Krantz et al. |
| 2023/0114130 | A1 | 4/2023 | Babich et al. |
| 2023/0122503 | A1 | 4/2023 | Goldberg, et al. |

FOREIGN PATENT DOCUMENTS

| | | | | |
|---|---|---|---|---|
| CA | 3070610 A1 | | 7/2021 | |
| CN | 110612126 A | | 12/2019 | |
| EP | 3 609 541 A1 | | 2/2020 | |
| JP | 2020-516611 A | | 6/2020 | |
| KR | 20190129931 A | | 11/2019 | |
| WO | WO-2018/183906 A1 | | 10/2018 | |
| WO | WO-2018187631 A1 | * | 10/2018 | ............. A61P 35/00 |
| WO | WO-2022/162210 A1 | | 8/2022 | |
| WO | WO-2022/162549 A2 | | 8/2022 | |
| WO | WO-2023/026235 A1 | | 3/2023 | |
| WO | WO-2023/049963 A1 | | 4/2023 | |
| WO | WO-2023/084396 A1 | | 5/2023 | |
| WO | WO-2023/084397 A1 | | 5/2023 | |

OTHER PUBLICATIONS

Notice of Allowance issued in U.S. Appl. No. 17/678,782, dated Nov. 21, 2024.

Abou, et al., "Towards the stable chelation of radium for biomedical applications with an 18-membered macrocyclic ligand," Chemical Science, vol. 12, pp. 3733-3742 (2021).

Aluicio-Sarduy, et al., "Establishing Radiolanthanum Chemistry for Targeted Nuclear Medicine Applications," Chemistry A European Journal Communication, vol. 26, pp. 1238-1242 (2020).

Bobba, et al., "Influence of short PEG linkers on biodistribution of 225AC-Macropa-YS5, an immunoconjugate for treating CD46 expressing cancer," Abstracts/Nuclear Medicine and Biology, pp. 108-109 (2022).

(56) References Cited

OTHER PUBLICATIONS

Macropa-NCS Cat. No. HY-111605, Master of Bioactive Molecules, Aug. 2023, 3 pages.
Randhawa, et al., "Development of novel sulfur-rich ligands for incorporation into mercury-197m/g radiopharmaceuticals," Abstracts/Nuclear Medicine and Biology, pp. 108-109 (2022).
Reissig, et al., "Modulating the pharmacokinetic profile of Actinium-225-labeled macropa-derived radioconjugates by dual targeting of PSMA and albumin," Theranostics, vol. 12, No. 17, pp. 7203-7215 (2022).
Shalgunov, et al., "Radiolabeling of a polypeptide polymer for intratumoral delivery of alpha-particle emitter, 225AC, and beta-particle emitter, 177Lu," Nuclear Medicine and Biology, vol. 104-105, pp. 11-21 (2022).
Siwowska, et al., "Preclinical Comparison of Albumin-Binding Radiofolates: Impact of Linker Entities on the In Vitro and In Vivo Properties," *Molecular Pharmaceutics*, vol. 14, pp. 523-532 (2017).
Barrett, et al., "First-in-Man Evaluation of 2 High-Affinity PSMA-Avid Small Molecules for Imaging Prostate Cancer," J. Nucl. Med.,, vol. 54, 380-387 (2013).
Beyer, et al., Comparison of the Blodistribution of $^{225}$Ac and Radio-Lanthanides as Citrate Complexes, Isot. Environ. Heal. Stud., vol. 26, 111-114 (1990).
Chamas, et al., "Clicked dipicolinic antennae for lanthanide luminescent probes," Dalton Trans., vol. 39, pp. 7091-7097 (2010).
Corson, et al., "Efficient Multigram Synthesis of the Bifunctional Chelating Agent (S)-1-p-Isothiocyanatobenzyl-diethylenetetraminepentaacetic Acid," Bioconjug. Chem., vol. 11, pp. 292-299 (2000).
Crawford, et al., "$^{211}$Rn/$^{211}$ At and $^{209}$At production with intense mass separated Fr ion beams for preclinical $^{211}$ At-based a-therapy research," Appl. Radiat. Isot., vol. 122, pp. 222-228 (2017).
Davis, et al., "Comparison of $^{225}$ Actinium Chelates: Tissue Distribution and Radiotoxicity," Nucl. Med. Biol., vol. 26, pp. 581-589 (1999).
Deal, et al., "Improved in Vivo Stability of Actinium-$^{225}$ Macrocyclic Complexes," J. Med. Chem. 1999, vol. 42, pp. 2988-2992 (1999).
Dennis, et al., "Albumin binding as a General Strategy for Improving the Pharmacokinetics of Proteins," J. Biol. Chem., vol. 277, pp. 35035-35043 (2002).
Dolomanov, et al., "OLEX2: a Complete Structure Solution, Refinement and Analysis Program, " J. Appl. Crystallogr., vol. 42, pp. 339-341 (2009).
Dumelin, et al., "A Portable Albumin Binder form a DNA-Encoded Chemical Library," Angew. Chem. Int. Ed., 47, 3196-3201 (2008).
Ferreirós-Martinez, "Macrocyclic Receptor Showing Extremely High Sr(II)/Ca(II) and Pb(II)/Ca(II) Selectivities with Potential Application in Chelation Treatment of Metal Intoxication," Inorg. Chem., vol. 50, pp. 3772-3784 (2011).
Ferrier, et al., "Synthesis and Characterization of the Actinium Aquo Ion," ACS Cent. Sci., vol. 3, pp. 176-185 (2017).
Ferrier, et al., " Spectroscopic and computational investigation of actinium coordination chemistry," Nat. Commun. 2016, 7, 12312 (2016), 8 pages.
Gatto, et al., "Synthesis of Calcium-Selective, Substituted Diaza-Crown Ethers: A Novel, One-Step Formation of Bibracchial Lariat Ethers (BIBLEs)," J. Am. Chem. Soc., vol. 106, 8240-8244 (1984).
Ghosh, et al., "Tumor Target Prostate Specific Membrane Antigen (PSMA) and Its Regulation in Prostate Cancer," J. Cell. Biochem., vol. 91, pp. 528-539 (Feb. 2004).
Hillier, et al., "Preclinical Evaluation of Novel Glutamate-Urea-Lysine Analogues That Target Prostate-Specific Membrane Antigen as Molecular Imaging Pharmaceuticals for Prostate Cancer," Cancer Res., vol. 69, pp. 6932-6940 (2009).
Jensen, "Aqueous Complexes for Efficient Size-based Separation of Americium from Curium," Inorg. Chem., vol. 53, pp. 6003-6012 (2014).
Kelly, Synthesis and pre-clinical evaluation of a new class of high-affinity 18F-labeled PSMA ligands for detection of prostate cancer by PET imagingA. Amor-Coarasa, A. Nikolopoulou, D. Kim, C. Williams, S. Ponnala, J. W. Babich, Eur. J. Nucl. Med. Mol. Imaging 2017, 44, 647-661.
Kozikowski, et al., Design of Remarkably Simply, Yet Potent Urea-Based Inhibitors of Glutamate Carboxypeptidase II (NAALADase), J. Med. Chem., vol. 44, pp. 298-301 (2001).
Leveque, et al., "Clinical Pharmacology of Trastuzumab," Curr. Clin. Pharmacol., vol. 3, pp. 51-55 (2008).
Leyland-Jones, et al., Pharmacokinetics, safety, and efficacy of trastuzumab administered every three weeks in combination with paclitaxel, J. Clin. Oncol., vol. 21, pp. 3965-3971 (Sep. 2003).
Maresca, et al., "A Series of Halogenated Heterodimeric Inhibitors of Prostate Specific Membrane Antigen (PSMA) as Radiolabeled Probes for Targeting Prostate Cancer." J. Med. Chem., vol. 52(2), pp. 347-357 (2009).
Mato-Iglesias, et al., Lanthanide Complexes Based on a 1,7-Diaza-12-crown-4 Platform Containing Picolinate Pendants: A New Structural Entry for the Design of Magnetic Resonance Imaging Contrast Agents, Inorg. Chem., vol. 47, pp. 7840-7851 (Aug. 2008).
McDevitt, et al., "Tumor Therapy with Targeted Atomic Nanogenerators," *Science*, vol. 294, 1537-1540 (Nov. 2001).
Miranda-Hernández, et al., "Theoretical approximations and experimental extinction coefficients of biopharmaceuticals," Anal. Bioanal. Chem., vol. 408, pp. 1523-1530 (2016).
Moasser, "The oncogene HER2: its signaling and transforming functions and its role in human cancer pathogenesis," Oncogene 2007, 26, 6469.
Müller, "Practice suggestions for better crystal structures," Crystallogr. Rev., vol. 15, pp. 57-83 (2009).
Neil, M. A. Fox, R. Pal, L.-O. Palsson, B. A. O'Sullivan, D. Parker, Dalton Trans., vol. 44, p. 14937-14951 (2015).
Price, et al., "A comparative evaluation of the chelators H4octapa and CHX-A'-DTPA with the therapeutic radiometal 9Y*," Nucl. Med. Biol., vol. 43(9), pp. 566-576 (2016).
Radchenko, et al., "Application of ion exchange and extraction chromatography to the separation of actinium from proton-irradiated thorium metal for analytical purposes," J. Chromatogr. A, vol. 1380, pp. 55-63 (2015).
Roca-Sabio, et al., "Macrocyclic Receptor Exhibiting Unprecedented Selectivity for Light Lanthanides," J. Am. Chem. Soc., vol. 131, pp. 3331-3341 (2009).
Sheldrick, "A short history of SHELX," Acta Crystallogr. Sect. A, vol. 64, pp. 112-122 (2008).
Sheldrick, "SHELXT—Integrated space-group and crystal-structure determination," Acta Crystallogr. Sect. A, vol. 71, pp. 3-8 (2015).
Zatelli, et al., Control of pituitary adenoma cell proliferation by somatostatin analogs, dopamine agonists and novel chimeric compounds, European Journal of Endocrinology, vol. 156, pp. S29-S35 (2007).
Zielinska, et al., "An Improved Method for the Production of Ac-225/Bi-213 from TH-229 for Targeted Alpha Therapy," Solvent Extr. And Ion Exch., vol. 25, pp. 339-349 (2007).
Search Report issued in co-pending European Patent Application No. 18775715.8, dated Oct. 16, 2020.
Price, et al., "Matching chelators to radiometals for radiopharmaceuticals", Chemical Society Reviews, vol. 43, pp. 260-290, (2014).
Wilson, et al., "Evaluation of nitrogen-rich macrocyclic ligands 1 chelation of therapeutic bismuth radioisotopes", Nuclear Medicine and Biology., vol. 42, No. 5, pp. 428-438 (May 2015).
International Search Report and Written Opinion Issued in International Application No. PCT/US2019/062479 on Feb. 27, 2020.
Pubchem. 7,16-Bis (6-carboxy-2-pyridinylmethyl)-1,4, 10, 13-tetraoxa-7, 16-diazacyclooctadecane. Jun. 20, 2012, pp. 1-6 [online], (retrieved on Dec. 27, 2019]. Retrieved from the Internet <URL:https://pubchem.ncbi.nlm.nih.gov/compound/57329142; p. 6.
Thiele, NA. An Eighteen-Membered Macrocyficligand for Actinium-225TargetedAlphaTherapy. Angewandte Chemie International Edition, vol. 56, pp. 14712-14717 (2017).
International Preliminary Report on Patentability issued in International Patent Application No. PCT/US2019/062479, dated Jun. 3, 2021.

(56) References Cited

OTHER PUBLICATIONS

Wilbur, "Chemical and radiochemical considerations in radiolabeling v [alpha]-emitting radionuclides", Current Radiopharmaceuticals, Bentham Science Publishers Ltd., NL, vol. 4, No. 3, pp. 214-247 (Jul. 2011).
Chen et al., "Novel molecular "add-on" based on Evans Blue confers superior pharmacokinetics and transforms drugs to theranostic agents", Journal of Nuclear Medicine, vol. 61, 2020, 44 pages.
Extended Search Report issued in European Patent Application No. 19887504.9, dated Oct. 5, 2022.
Kostelnik et al., "Radioactive Main Group and Rare Earth Metals for Imaging and Therapy", Chem. Rev., vol. 119, 2019, pp. 902-956.
Regueiro-Figueroa et al., "Stabilizing Divalent Europium in Aqueous Solution Using Size-Discrimination and Electrostatic Effects", Inorg. Chem., vol. 54, 2015, pp. 4940-4952.
Non-Final Office Action issued in U.S. Appl. No. 17/294,375, dated Jan. 16, 2025.
Non-Final Office Action issued in U.S. Appl. No. 17/294,375, dated Jan. 8, 2026.

* cited by examiner

Top View

Side View

Top View 1 2 3 4 5 6 7 8 9 10

MACROCYCLIC COMPLEXES OF ALPHA-EMITTING RADIONUCLIDES AND THEIR USE IN TARGETED RADIOTHERAPY OF CANCER

CROSS-REFERENCE TO RELATED APPLICATIONS

This application is a divisional of U.S. patent application Ser. No. 16/689,856, filed Nov. 20, 2019, which claims the benefit of and priority to U.S. Provisional Patent Application No. 62/769,989, filed Nov. 20, 2018, U.S. Provisional Patent Application No. 62/788,700, filed Jan. 4, 2019, and U.S. Provisional Patent Application No. 62/792,835, filed Jan. 15, 2019, each of which is incorporated herein by reference in its entirety for any and all purposes.

U.S. GOVERNMENT RIGHTS

This invention was made with government support under UL1TR00457 awarded by the National Institutes of Health. The government has certain rights in the invention.

FIELD

The present technology generally relates to macrocyclic complexes of alpha-emitting radionuclides, as well as compositions including such compounds and methods of use.

SUMMARY

In an aspect, a compound of Formula I is provided:

(I)

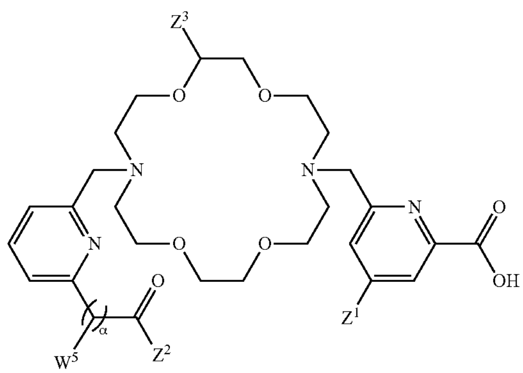

or a pharmaceutically acceptable salt thereof, wherein $Z^1$ is H or —$X^1$—$W^2$;

$Z^2$ is OH or NH—$W^3$:

$Z^3$ is H or $W^7$;

α is 0 or 1;

X is O, NH, or S;

$W^2$ and $W^3$ are each independently H, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2$R', —$SO_2$(OR'), —$SO_2NR'_2$, —P(O)$(OR')_2$, —P(O)R'(OR'), —P(O)$R'_2$, —CN, —OCN, —SCN, —NCO, —NCS, —NR'—$NH_2$, —N═C═N—R', —$SO_2$Cl, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2$R', —$SO_2$(OR'), —$SO_2NR'_2$, —P(O)$(OR')_2$, —P(O)R'(OR'), —P(O)$R'_2$, —CN, —OCN, —SCN, —NCO, —NCS, —NR'—$NH_2$, —N═C═N—R', —$SO_2$Cl, —C(O)Cl, or an epoxide group; and R' is independently at each occurrence H, halo, —$N_3$, $C_1$-$C_6$ alkyl, $C_3$-$C_6$ cycloalkyl, $C_2$-$C_6$ alkenyl, $C_5$-$C_8$ cycloalkenyl, $C_2$-$C_6$ alkynyl, $C_8$-$C_{10}$ cycloalkynyl, $C_5$-$C_6$ aryl, heterocyclyl, or heteroaryl.

In a related aspect, a compound of Formula IA is provided (IA)

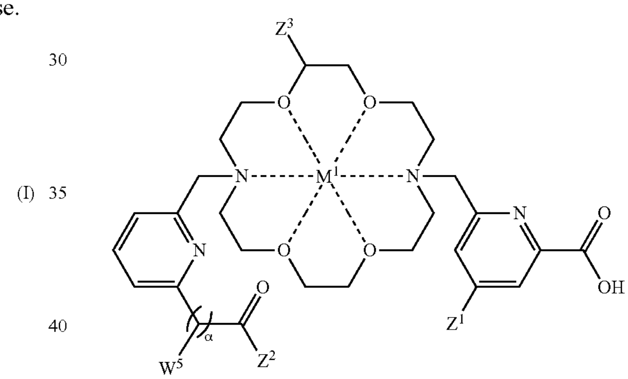

or a pharmaceutically acceptable salt thereof, wherein $M^1$ is an alpha-emitting radionuclide:

$Z^1$ is H or —$X^1$—$W^2$;

$Z^2$ is OH or NH—$W^3$;

$Z^3$ is H or $W^7$;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$OR' where z is 1, 2, 3, 4, 5, 6, 7, 8, 9, or 10, —SR', —OC(O)R', —C(O)OR', —C(S)OR', —S(O)R', —$SO_2$R', —$SO_2$(OR'), —$SO_2NR'_2$, —P(O)$(OR')_2$, —P(O)R'(OR'), —P(O)$R'_2$, —CN, —OCN, —SCN, —NCO, —NCS, —NR'—$NH_2$, —N═C═N—R', —$SO_2$Cl, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)_y—R'$ where y is 1, 2, 3, 4, 5, 6, 7, 8, 9, or 10, $—CH_2CH_2—(OCH_2CH_2)_zOR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group; and R' is independently at each occurrence H, halo, $—N_3$, $C_1$-$C_6$ alkyl, $C_3$-$C_6$ cycloalkyl, $C_2$-$C_6$ alkenyl, $C_5$-$C_8$ cycloalkenyl, $C_2$-$C_6$ alkynyl, $C_5$-$C_{10}$ cycloalkynyl, $C_5$-$C_6$ aryl, heterocyclyl, or heteroaryl.

In a further related aspect, the present technology provides a compound useful in targeted radiotherapy of cancer and/or mammalian tissue overexpressing prostate specific membrane antigen ("PSMA") (a "targeting compound") where the compound is of Formula II (II)

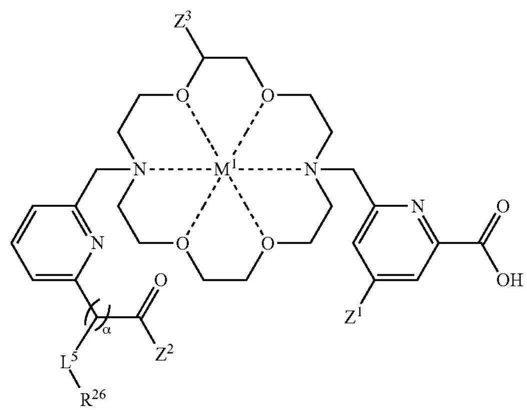

or a pharmaceutically acceptable salt thereof, wherein $M^1$ is an alpha-emitting radionuclide;

$Z^1$ is H or $-L^3-R^{22}$;

$Z^2$ is OH or $NH-L^4-R^{24}$;

$Z^3$ is H or $-L^6-R^{28}$;

α is 0 or 1;

$X^1$ is O, NH, or S;

$L^3$, $L^4$, $L^5$, and $L^6$ are independently at each occurrence a bond or a linker group; and $R^{22}$, $R^{24}$, $R^{26}$, and $R^{28}$ each independently comprises an antibody, antibody fragment (e.g., an antigen-binding fragment), a binding moiety, a binding peptide, a binding polypeptide (such as a selective targeting oligopeptide containing up to 50 amino acids), a binding protein, an enzyme, a nucleobase-containing moiety (such as an oligonucleotide, DNA or RNA vector, or aptamer), or a lectin.

In a further related aspect, a modified antibody, modified antibody fragment, or modified binding peptide comprising a linkage arising from conjugation of a compound of Formula I or pharmaceutically acceptable salt thereof, with an antibody, antibody fragment, or binding peptide. In a related aspect, a modified antibody, modified antibody fragment, or modified binding peptide is provided that includes a linkage arising from conjugation of a compound of Formula IA or a pharmaceutically acceptable salt thereof, with an antibody, antibody fragment, or binding peptide.

In any embodiment and/or aspect disclosed herein (for simplicity's sake, hereinafter recited as "in any embodiment disclosed herein" or the like), it may be that the antibody includes belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab. In any embodiment disclosed herein, it may be that the antibody fragment includes an antigen-binding fragment of belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab. In any embodiment disclosed herein, it may be that the binding peptide includes a prostate specific membrane antigen ("PSMA") binding peptide, a somatostatin receptor agonist, a bombesin receptor agonist, a seprase binding compound, or a binding fragment thereof.

In another aspect, the present technology also provides compositions (e.g., pharmaceutical compositions) and medicaments comprising any of one of the embodiments of the compounds of Formulas I, IA, or II (or a pharmaceutically acceptable salt thereof) disclosed herein and a pharmaceutically acceptable carrier or one or more excipients or fillers. In a similar aspect, the present technology also provides compositions (e.g., pharmaceutical compositions) and medicaments comprising any of one of the embodiments of the modified antibody, modified antibody fragment, or modified binding peptide of the present technology disclosed herein and a pharmaceutically acceptable carrier or one or more excipients or fillers.

In an aspect, a method of treating a subject is provided, wherein the method includes administering a targeting compound of the present technology to the subject or administering a modified antibody, modified antibody fragment, or modified binding peptide of the present technology to the subject. In any embodiment disclosed herein, it may be that the subject suffers from cancer and/or mammalian tissue overexpressing prostate specific membrane antigen ("PSMA").

In an aspect, a compound is provided that includes a first domain having a blood-protein binding moiety with low specific affinity for the blood-protein, a second domain having a tumor targeting moiety with high affinity for a tumor antigen, and a third domain having a chelator.

BRIEF DESCRIPTION OF THE DRAWINGS

FIG. 1D, top view). Ellipsoids are drawn at the 50% probability level. Counteranions and hydrogen atoms attached to carbons are omitted for clarity.

FIGS. 2A-C shows the biodistribution of $^{225}Ac(NO_3)_3$ (FIG. 2A), $[^{225}Ac(macropa)]^+$ (FIG. 2B), and $[^{225}Ac(DOTA)]^-$ (FIG. 2C) for select organs following intravenous injection in mice. Adult C57BL/6 mice were sacrificed 15 min, 1 h, or 5 h post injection. Values for each time point are given as mean % ID/g±1 SD.

DETAILED DESCRIPTION

Figure 1A:
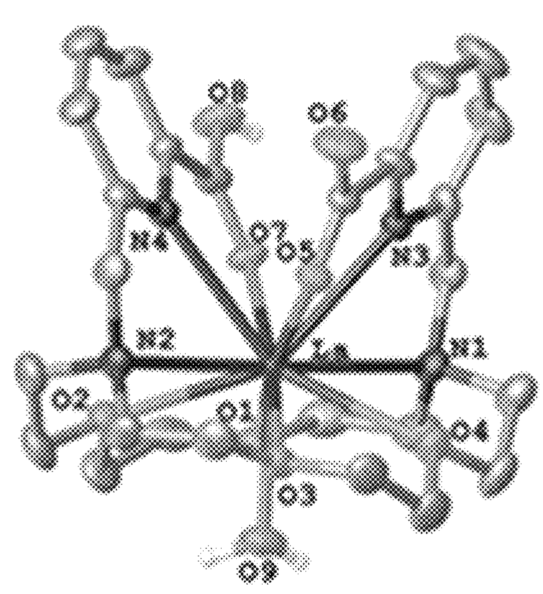
FIGS. 1A and 1B shows x-ray crystal structures of [La $(Hmacropa)(H_2O)]\cdot(ClO_4)_2$ (FIG. 1A, side view.
Figure 1B:
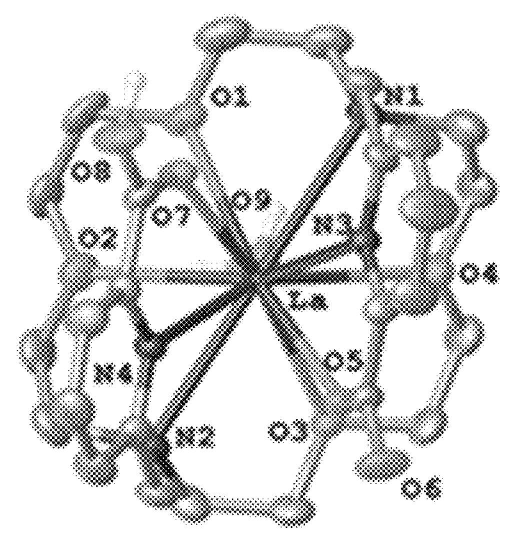
Figure 1C:
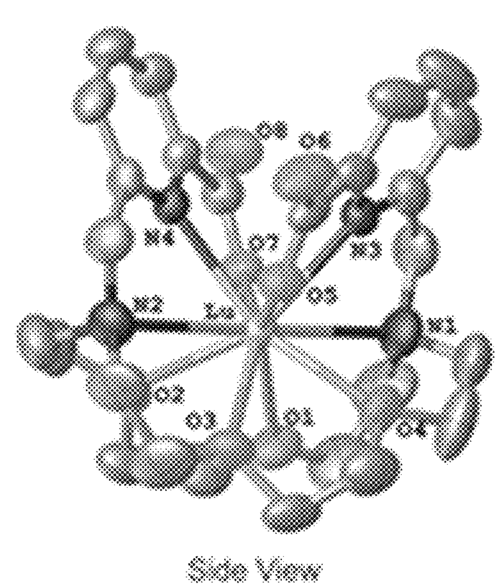
FIGS. 1C and 1D shows x-ray crystal structures of [Lu(macropa)]·$ClO_4$·DMF (FIG. 1C, side view.
Figure 1D:
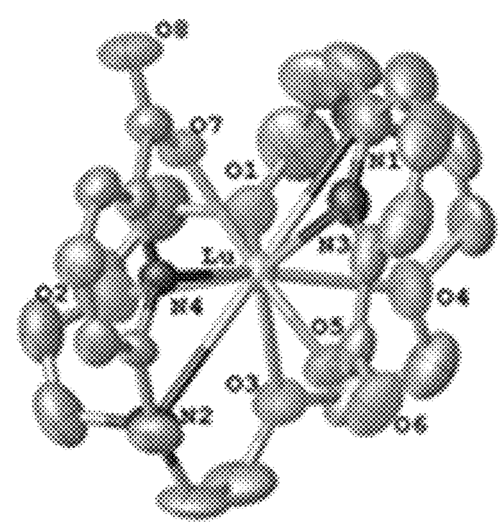

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; alkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $—CH═CH(CH_3)$, $—CH═C(CH_3)_2$, $—C(CH_3)═CH_2$, $—C(CH_3)═CH(CH_3)$, $—C(CH_2CH_3)═CH_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $—C≡CH$, $—C≡CCH_3$, $—CH_2C≡CCH_3$, $—C≡CCH_2CH(CH_2CH)_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O— group. A "protected carboxylate" refers to a —C(O)O—G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to $—COOR^{70}$ groups. $R^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., $—C(O)NR^{71}R^{72}$, and $—NR^{71}C(O)R^{72}$ groups, respectively. $R^{71}$ and $R^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups ($—C(O)NH_2$) and formamide groups (—NHC(O)H). In some embodiments, the amide is $—NR^{71}C(O)—(C_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., $—NR^{73}C(O)OR^{74}$ and $—OC(O)NR^{73}R^{74}$ groups, respectively. $R^{73}$ and $R^{74}$ are independently a substituted or unsubstituted alkyl, alkenyl, alkynyl, cycloalkyl, aryl, aralkyl, heterocyclylalkyl, or heterocyclyl group as defined herein. $R^{77}$ may also be H.

The term "amine" (or "amino") as used herein refers to $—NR^{75}R^{76}$ groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methyl-amino, dimethylamino, ethylamino, diethylamino, propylamino, isopropylamino, phenylamino, or benzylamino.

The term "sulfonamido" includes S- and N-sulfonamide groups, i.e., $—SO_2NR^{78}R^{79}$ and $—NR^{78}SO_2R^{79}$ groups, respectively. $R^{78}$ and $R^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups ($—SO_2NH_2$). In some embodiments herein, the sulfonamido is $—NHSO_2$-alkyl and is referred to as the "alkylsulfonylamino" group.

The term "thiol" refers to —SH groups, while sulfides include $—SR^{80}$ groups, sulfoxides include $—S(O)R^{81}$ groups, sulfones include $—SO_2R^{82}$ groups, and sulfonyls include $—SO_2OR^{83}$. $R^{80}$, $R^{81}$, $R^{82}$, and $R^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to $—NR^{84}—C(O)—NR^{85}R^{86}$ groups. $R^{84}$, $R^{85}$, and $R^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to $—C(NR^{87})NR^{88}R^{89}$ and $—NR^{87}C(NR^{88})R^{89}$, wherein $R^{87}$, $R^{88}$, and $R^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to $—NR^{90}C(NR^{91})NR^{92}R^{93}$, wherein $R^{90}$, $R^{91}$, $R^{92}$ and $R^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to $—C(R^{94})═C(R^{95})NR^{96}R^{97}$ and $—NR^{94}C(R^{95})═C(R^{96})R^{97}$, wherein $R^{94}$, $R^{95}$, $R^{96}$ and $R^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—.

The term "imide" refers to $—C(O)NR^{98}C(O)R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to $—CR^{100}(NR^{101})$ and $—N(CR^{100}R^{101})$ groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an $—NO_2$ group.

The term "trifluoromethyl" as used herein refers to $—CF_3$.

The term "trifluoromethoxy" as used herein refers to $—OCF_3$.

The term "azido" refers to $—N_3$.

The term "trialkyl ammonium" refers to a $—N(alkyl)_3$ group. A trialkylammonium group is positively charged and thus typically has an associated anion, such as halogen anion.

The term "trifluoromethyldiazirido" refers to

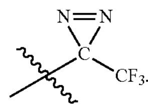 [SMILES: *C1(C(F)(F)F)N=N1]

The term "isocyano" refers to —NC.

The term "isothiocyano" refers to —NCS.

The term "pentafluorosulfanyl" refers to $—SF_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

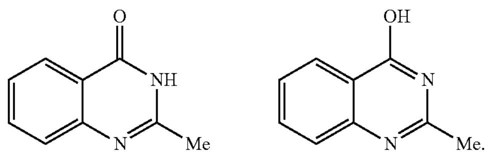 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

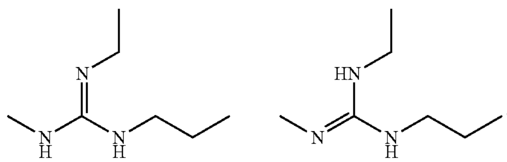

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the present technology.

The Present Technology

Although targeted radiotherapy has been practiced for some time using macrocyclic complexes of radionuclides, the macrocycles currently in use (e.g., DOTA) generally form complexes of insufficient stability with radionuclides, particularly for radionuclides of larger size, such as actinium, radium, bismuth, and lead isotopes. Such instability results in dissociation of the radionuclide from the macrocycle, and this results in a lack of selectivity to targeted tissue, which also results in toxicity to non-targeted tissue.

The present technology provides new macrocyclic complexes that are substantially more stable than those of the conventional art. Thus, these new complexes can advantageously target cancer cells more effectively, with substantially less toxicity to non-targeted tissue than complexes of the art. Moreover, the new complexes can advantageously be produced at room temperature, in contrast to DOTA-type complexes, which generally require elevated temperatures (e.g., at least 80° C.) for complexation with the radionuclide. The present technology also specifically employs alpha-emitting radionuclides instead of beta radionuclides. Alpha-emitting radionuclides are of much higher energy, and thus substantially more potent, than beta-emitting radionuclides.

Thus, in one aspect, a compound of Formula I is provided:

(I)

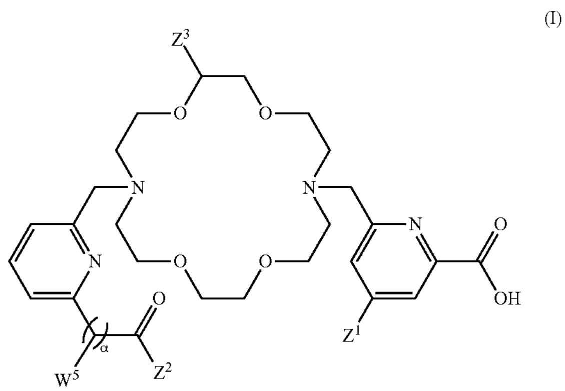

or a pharmaceutically acceptable salt thereof, wherein $Z^1$ is H or $—X^1—W^2$;

$Z^2$ is OH or $NH—W^3$;

$Z^3$ is H or W;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)_y—R'$ where y is 1, 2, 3, 4, 5, 6, 7, 8, 9, or 10, $—CH_2CH_2—(OCH_2CH_2)_zOR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, —$SO_2NR'_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, —$CH_2CH_2$—$(OCH_2C_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)y_x$-R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2R'$, —$SO_2$(OR'), —$SO_2NR'_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2Cl$, —C(O)Cl, or an epoxide group; and R' is independently at each occurrence H, halo, —$N_3$, $C_1$-$C_6$ alkyl, $C_3$-$C_6$ cycloalkyl, $C_2$-$C_6$ alkenyl, $C_5$-$C_8$ cycloalkenyl, $C_2$-$C_6$ alkynyl, $C_8$-$C_{10}$ cycloalkynyl, $C_5$-$C_6$ aryl, heterocyclyl, or heteroaryl.

Significantly, the uncomplexed form of Formula I can be complexed with a radionuclide, such as an alpha-emitting radionuclide, at room temperature (generally 18-30° C., or about or no more than 20° C., 25° C., or 30° C.) at high radiochemical yields, e.g., at least or greater than 90%, 95%, 97%, or 98%.

In a related aspect, a compound of Formula IA is provided (IA)

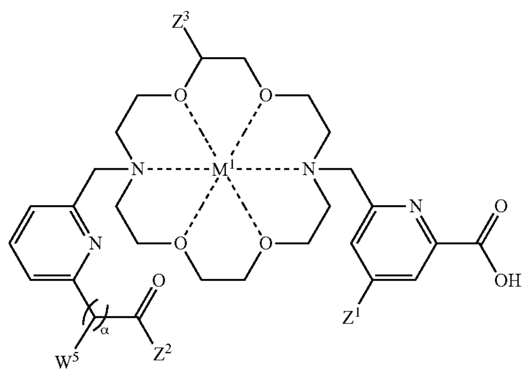

or a pharmaceutically acceptable salt thereof, wherein $M^1$ is an alpha-emitting radionuclide;

$Z^1$ is H or —$X^1$—$W^2$;

$Z^2$ is OH or NH—$W^3$.

$Z^3$ is H or $W^7$;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$OR' where z is 1, 2, 3, 4, 5, 6, 7, 8, 9, or 10, —SR', —OC(O)R', —C(O)OR', —C(S)OR', —S(O)R', —$SO_2R'$, —$SO_2$(OR'), —$SO_2NR'_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)y_x$-R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2R'$, —$SO_2$(OR'), —$SO_2NR'_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2Cl$, —C(O)Cl, or an epoxide group; and R' is independently at each occurrence H, halo, —$N_3$, $C_1$-$C_6$ alkyl, $C_3$-$C_6$ cycloalkyl, $C_2$-$C_6$ alkenyl, $C_5$-$C_8$ cycloalkenyl, $C_2$-$C_6$ alkynyl, $C_8$-$C_{10}$ cycloalkynyl, $C_5$-$C_6$ aryl, heterocyclyl, or heteroaryl.

In any embodiment disclosed herein, it may be that $M^1$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

In a further related aspect, the present technology provides a compound useful in targeted radiotherapy of cancer and/or mammalian tissue overexpressing prostate specific membrane antigen ("PSMA") (a "targeting compound") where the compound is of Formula II (II)

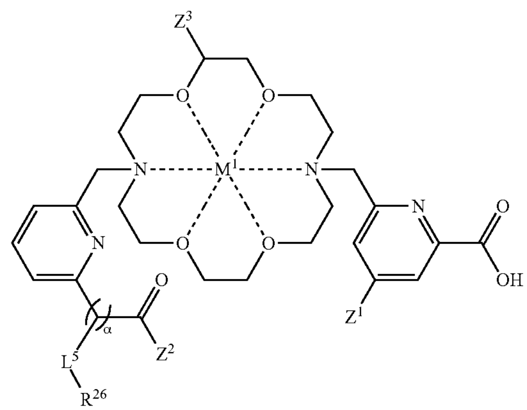

or a pharmaceutically acceptable salt thereof, wherein $M^1$ is an alpha-emitting radionuclide;

$Z^1$ is H or -$L^3$-$R^{22}$;

$Z^2$ is OH or NH-$L^4$-$R^{24}$;

$Z^3$ is H or -$L^6$-$R^{28}$;

α is 0 or 1;

$X^1$ is O, NH, or S;

$L^3$, $L^4$, $L^5$, and $L^6$ are independently at each occurrence a bond or a linker group; and $R^{22}$, $R^{24}$, $R^{26}$, and $R^{28}$ each independently comprises an antibody, antibody fragment (e.g., an antigen-binding fragment), a binding moiety, a binding peptide, a binding polypeptide (such as a selective targeting oligopeptide containing up to 50 amino acids), a binding protein, an enzyme, a nucleobase-containing moiety (such as an oligonucleotide, DNA or RNA vector, or aptamer), or a lectin.

In any embodiment disclosed herein encompassed by Formula II, $M^1$ may be actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

Representative $R^{22}$, $R^{24}$, $R^{26}$, and $R^{28}$ groups include those antibodies listed in Table A as well as antigen-binding fragments of such antibodies and any equivalent embodiments, as would be known to those of ordinary skill in the art.

TABLE A

Representative Antibodies

| Antibody (Trade Name(s)) | Disclosed In (U.S. Pat. No. or Patent Appl. Publ. No.)* |
|---|---|
| Belimumab (Benlysta) | 7,138,501 |
| Mogamulizumab (Poteligeo) | 6,989,145 |
| Blinatumomab (Blincyto) | 7,112,324 |
| Ibritumomab tiuxetan (Zevalin) | 5,776,456 |
| Obinutuzumab (Gazyva) | 6,602,684 |
| Ofatumumab[1] (Arzerra) | 8,529,902 |
| Rituximab (Rituxan, MabThera) | 5,736,137 |
| Inotuzumab ozogamicin (Besponsa) | 8,153,768 |
| Moxetumomab pasudotox (Lumoxiti) | 8,809,502 |
| Brentuximab vedotin (Adcetris) | 7,829,531; 7,090,843 |
| Daratumumab (Darzalex) | 7,829,673 |
| Ipilimumab (Yervoy) | 6,984,720 |
| Cetuximab (Erbitux) | 6,217,866 |
| Necitumumab (Portrazza) | 7,598,350 |
| Panitumumab (Vectibix) | 6,235,883 |
| Dinutuximab[2] (Unituxin) | 7,432,357 |
| Pertuzumab (Perjeta, Omnitarg) | 7,862,817 |
| Trastuzumab[3] (Herceptin) | 5,821,337 |
| Trastuzumab emtansine (Kadcyla) | 7,097,840 |
| Siltuximab (Sylvant) | 7,612,182 |
| Cemiplimab[4] (Libtayo) | 9,987,500 |
| Nivolumab (Opdivo) | 8,008,449 |
| Pembrolizumab (Keytruda) | 8,354,509 |
| Olaratumab (Lartruvo) | 8,128,929 |
| Atezolizumab (Tecentriq) | 8,217,149 |
| Avelumab[5] (Bavencio) | 9,624,298 |
| Durvalumab (Imfinzi) | 8,779,108 |
| Capromab pendetide (Prostascint) | 5,162,504 |
| Elotuzumab (Empliciti) | 7,709,610 |
| Denosumab (Prolia, Xgeva) | 6,740,522 |
| Ziv-aflibercept (Zaltrap) | 7,070,959 |
| Bevacizumab (Avastin) | 6,054,297 |
| Ramucirumab (Cyramza) | 7,498,414 |
| Tositumomab (Bexxar) | 6,565,827; 6,287,537;, 6,090,365; 6,015,542; 5,843,398; 5,595,721 |
| Gemtuzumab ozogamicin (Mylotarg) | 5,773,001 |
| Alemtuzumab (Campath-1H) | 6,569,430; 5,846,534 |
| Cixutumumab | 7,968,093; 7,638,605 |
| Girentuximab (Rencarex) | 8,466,263 |
| Nimotuzumab (Theracim, Theraloc) | 6,506,883 |
| Catumaxomab (Removab) | 9,017,676; 8,663,638; 2013/0309234A1 |
| Etaracizumab (Abegrin, Vitaxin) | 2004/0001835A1 |

*Note:
the disclosures of the each of the patents and patent publications listed in Table A are incorporated herein by reference.
[1]Also designated 2F2.
[2]Also designated Ch14.18.
[3]Also designated HuMaB4D5-8.
[4]Also designated H4H7798N.
[5]Also designated A09-246-2.

In any embodiment disclosed herein, it may be that the binding peptide comprises comprises a prostate specific membrane antigen ("PSMA") binding peptide, a somatostatin receptor agonist, a bombesin receptor agonist, a seprase binding compound, or a binding fragment thereof. Exemplary PSMA binding peptides include, but are not limited to, those according to the following structure

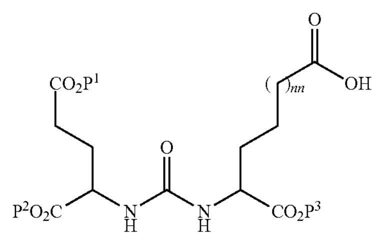

where nn is 0, 1, or 2, and $P^1$, $P^2$, and $P^3$ are each independently H, methyl, benzyl, 4-methoxybenzyl, or tert-butyl. In any embodiment herein, it may be that each of $P^1$, $P^2$, and $P^3$ are H.

Somatostatin, illustrated in Scheme A, is a peptide hormone that regulates the endocrine system and affects neurotransmission and cell proliferation via interaction with G protein-coupled somatostatin receptors and inhibition of the release of numerous secondary hormones. Somatostatin has two active forms produced by alternative cleavage of a single preproprotein. There are five known somatostatin receptors, all being G protein-coupled seven transmembrane receptors: SST1 (SSTR1); SST2 (SSTR2); SST3 (SSTR3); SST4 (SSTR4); and SST5 (SSTR5). Exemplary somatostatin receptor agonists include somatostatin itself, lanreotide, octreotate, octreotide, pasireotide, and vapreotide.

Scheme A.

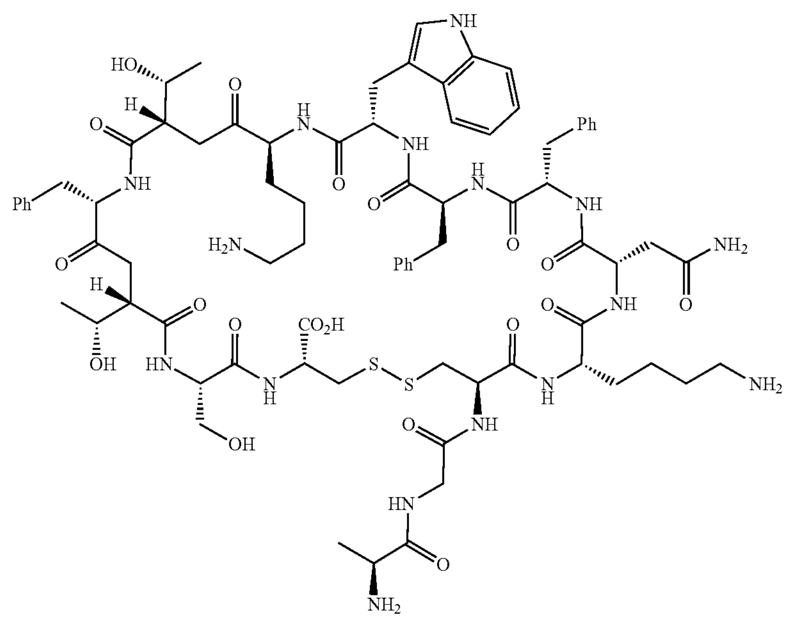

Many neuroendocrine tumors express SSTR2 and the other somatostatin receptors. Long acting somatostatin agonists (e.g., Octreotide, Lanreotide) are used to stimulate the SSTR2 receptors, and thus to inhibit further tumor proliferation. See, Zatelli M C, et al., (April 2007). "Control of pituitary adenoma cell proliferation by somatostatin analogs, dopamine agonists and novel chimeric compounds". European Journal of Endocrinology/European Federation of Endocrine Societies. 156 Suppl 1: S29-35. Octreotide is an octapeptide that mimics natural somatostatin but has a significantly longer half-life in vivo. Octreotide is used for the treatment of growth hormone producing tumors (acromegaly and gigantism), when surgery is contraindicated, pituitary tumors that secrete thyroid stimulating hormone (thyrotropinoma), diarrhea and flushing episodes associated with carcinoid syndrome, and diarrhea in people with vasoactive intestinal peptide-secreting tumors (VIPomas). Lanreotide is used in the management of acromegaly and symptoms caused by neuroendocrine tumors, most notably carcinoid syndrome. Pasireotide is a somatostatin analog with an increased affinity to SSTR5 compared to other somatostatin agonists and is approved for treatment of Cushing's disease and acromegaly. Vapreotide is is used in the treatment of esophageal variceal bleeding in patients with cirrhotic liver disease and AIDS-related diarrhea.

Bombesin is a peptide originally isolated from the skin of the European fire-bellied toad (*Bombina bombina*). In addition to stimulating gastrin release from G cells, bombesin activates at least three different G-protein-coupled receptors: BBR1, BBR2, and BBR3, where such activity includes agonism of such receptors in the brain. Bombesin is also a tumor marker for small cell carcinoma of lung, gastric cancer, pancreatic cancer, and neuroblastoma. Bombesin receptor agonists include, but are not limited to, BBR-1 agonists, BBR-2 agonists, and BBR-3 agonists.

Seprase (or Fibroblast Activation Protein (FAP)) is an integral membrane serine peptidase. In addition to gelatinase activity, seprase has a dual function in tumour progression. Seprase promotes cell invasiveness towards the ECM and also supports tumour growth and proliferation. Seprase binding compounds include seprase inhibitors In a further related aspect, a modified antibody, modified antibody fragment, or modified binding peptide comprising a linkage arising from conjugation of a compound of Formula I or pharmaceutically acceptable salt thereof, with an antibody, antibody fragment, or binding peptide. In a related aspect, a modified antibody, modified antibody fragment, or modified binding peptide is provided that includes a linkage arising from conjugation of a compound of Formula IA or a pharmaceutically acceptable salt thereof, with an antibody, antibody fragment, or binding peptide. In any embodiment disclosed herein, it may be that the antibody includes belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab. In any embodiment disclosed herein, it may be that the antibody fragment includes an antigen-binding fragment of belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab. In any embodiment disclosed herein, it may be that the binding peptide includes a prostate specific membrane antigen ("PSMA") binding peptide, a somatostatin receptor agonist, a bombesin receptor agonist, a seprase binding compound, or a binding fragment thereof.

As an example of a modified antibody, modified antibody fragment, or modified binding peptide of the present technology, it may be that the linkage is a thiocyanate linkage; wherein the thiocyanate linkage arises from conjugation of the compound with the antibody, antibody fragment, or binding peptide; and wherein the compound is

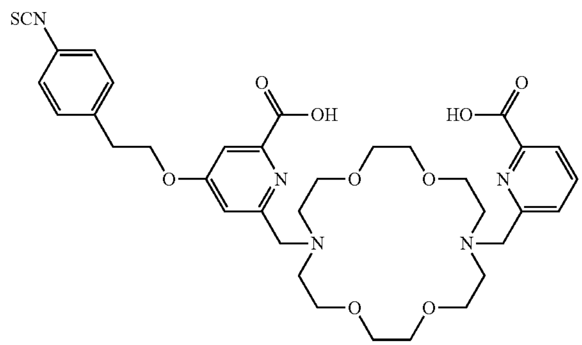

or pharmaceutically acceptable salt thereof.

As another example of a modified antibody, modified antibody fragment, or modified binding peptide of the present technology, it may be that the linkage is a thiocyanate linkage; wherein the thiocyanate linkage arises from conjugation of the compound with the antibody, antibody fragment, or binding peptide; and wherein the compound is

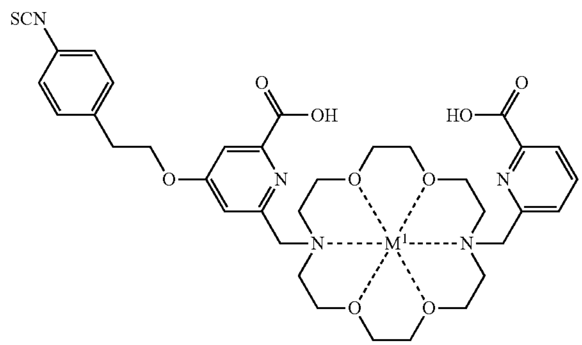

or a pharmaceutically acceptable salt thereof.

In any embodiment herein, it may be that the structures include compounds of Formula III, a modified antibody, modified antibody fragment, or modified binding peptide comprising a linkage arising from conjugation of a compound of Formula III or pharmaceutically acceptable salt thereof, with an antibody, antibody fragment, or binding peptide, compounds of Formula IV, a modified antibody, modified antibody fragment, or modified binding peptide comprising a linkage arising from conjugation of a compound of Formula IV or pharmaceutically acceptable salt thereof, with an antibody, antibody fragment, or binding peptide, and targeting compounds of Formula V (III)

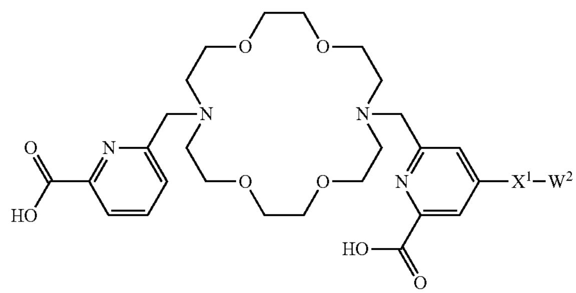

or a pharmaceutically acceptable salt thereof, (IV)

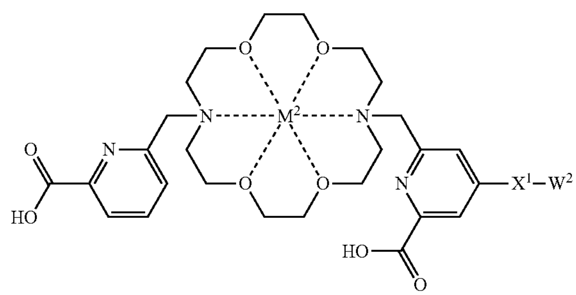

or a pharmaceutically acceptable salt thereof, (V)

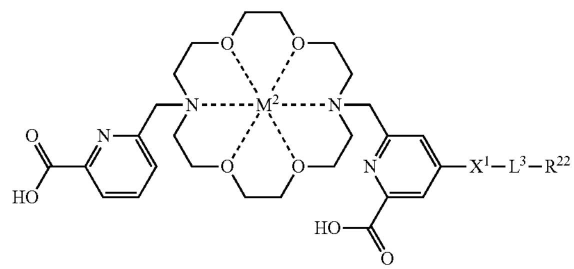

or a pharmaceutically acceptable salt thereof, wherein is independently at each occurrence an alpha-emitting radionuclide.

Targeting compounds of Formula V may be prepared by a process that includes reacting a compound of Formula III or IV with $R^{22}$—$W^1$, where Table B provides representative examples (where n is independently at each occurrence 1, 2, 3, 4, 5, 6, 7, 8, 9, or 10). As such, $R^{22}$ may be conjugated to macrocycle $R^{21}$ by reaction of complementary chemical functional groups $W^1$ and $W^2$ to form linker L. For example, $R^{22}$—$W^1$ may include a modified target amino acid residue within a protein (e.g., one of the representative antibodies disclosed in Table A or an antigen-binding fragment thereof; a PSMA binding peptide, a somatostatin receptor agonist, a bombesin receptor agonist, a seprase binding compound, or a binding fragment of any one thereof). $W^1$ may include a reactive chemical functional moiety, non-limiting examples of which are disclosed in the Table B, where $W^2$ may be selected to selectively react with $W^1$ in order to provide $L^3$ of Formula V.

TABLE B
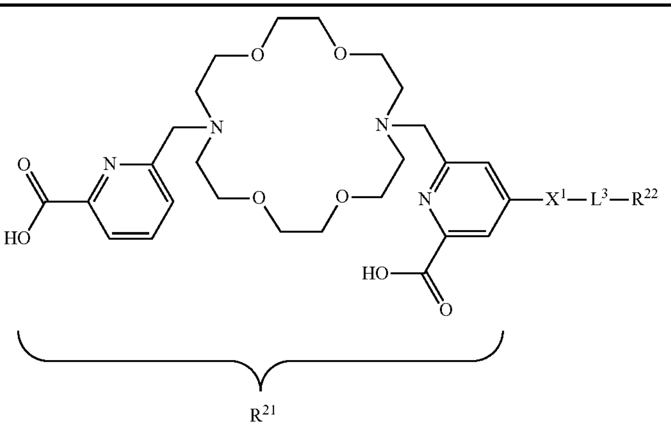
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| $N_3$—$R^{22}$ | 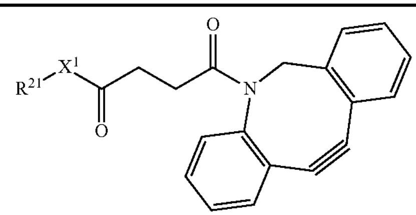 | NH | 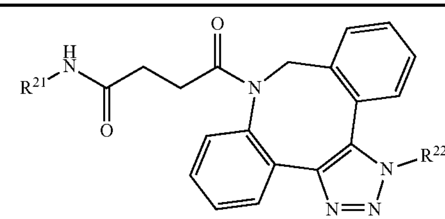 and/or 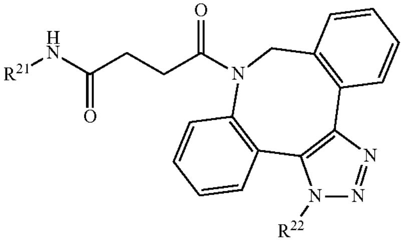 |

TABLE B-continued
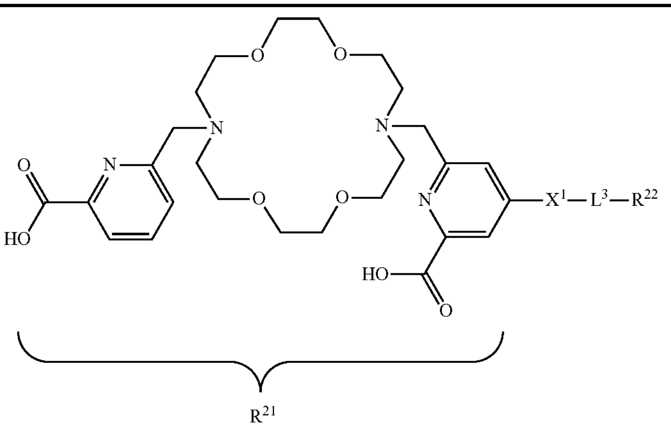
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 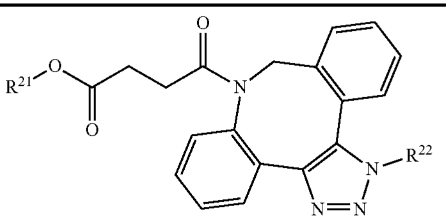 and/or 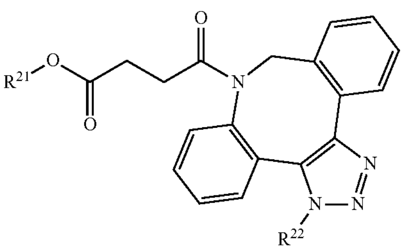 |

TABLE B-continued
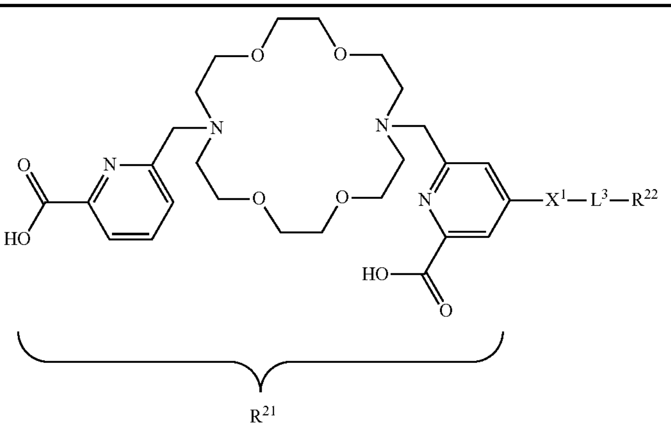
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | 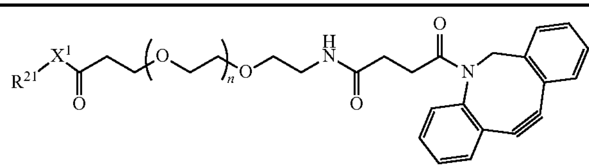 | NH | 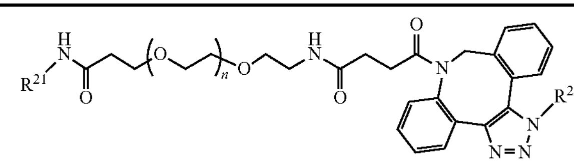 and/or 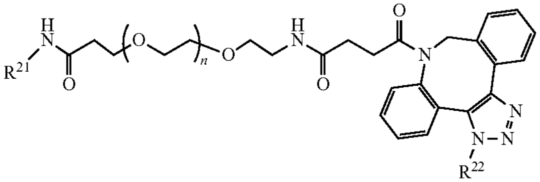 |
| | | O | 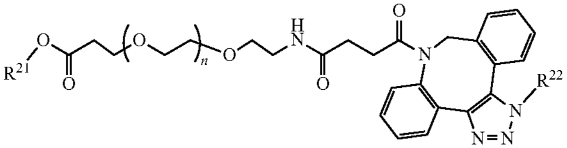 and/or |

TABLE B-continued
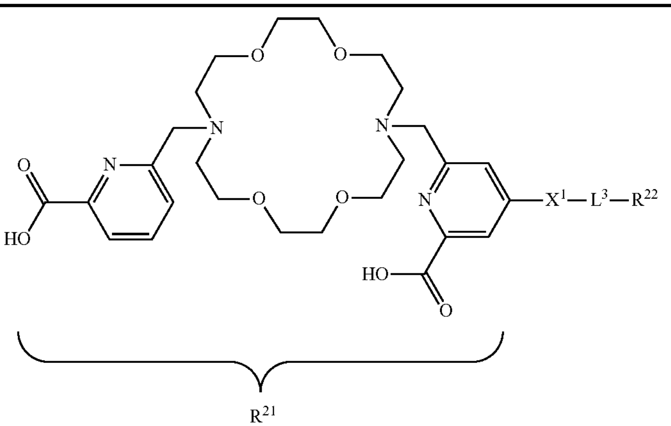
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| 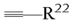 | 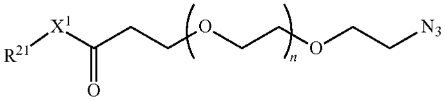 | NH | 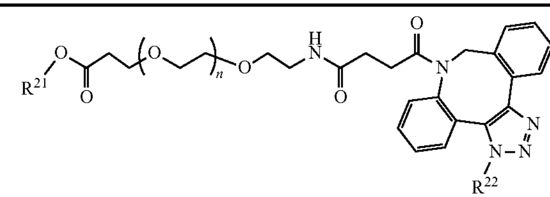 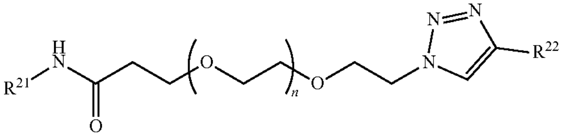 and/or 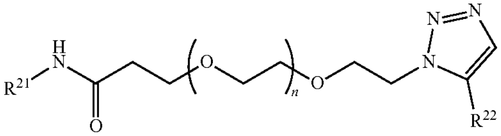 |

TABLE B-continued
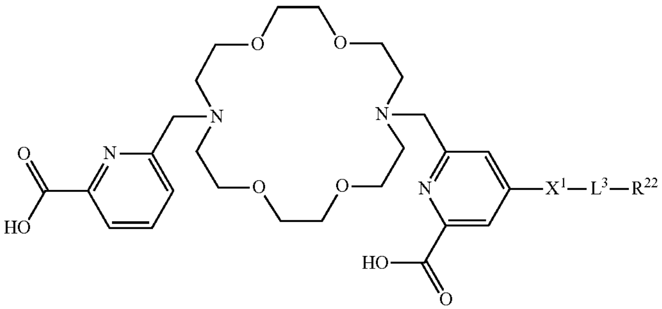
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 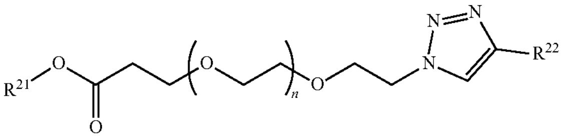 and/or 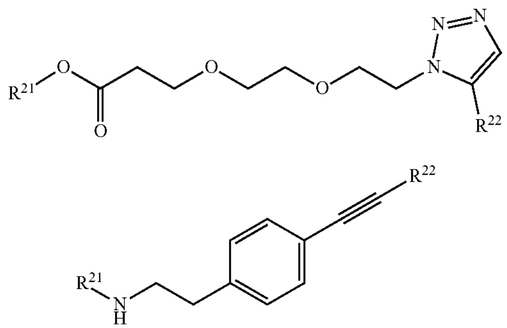 |
| | 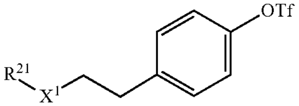 | NH | |

TABLE B-continued
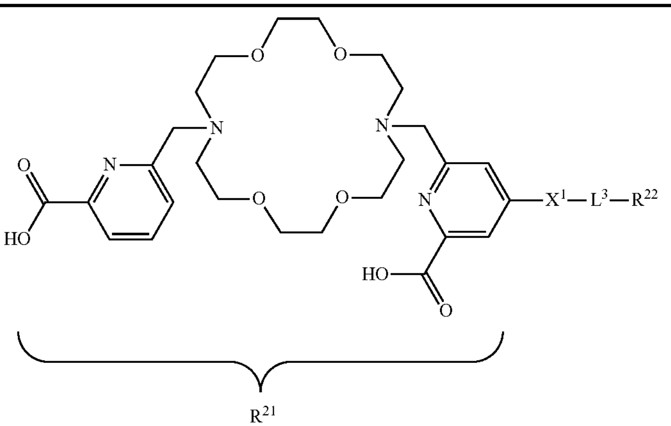
| W$^1$-R$^{22}$ | R$^{21}$-X$^1$-W$^2$ | X$^1$ | Final Conjugation Product (R$^{21}$-X$^1$-L$^3$-R$^{22}$) |
|---|---|---|---|
| | | O | 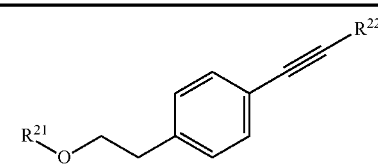 |
| | 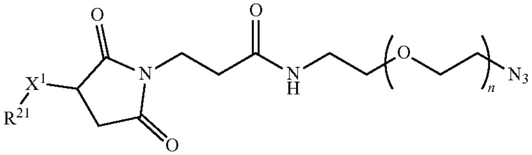 | S | 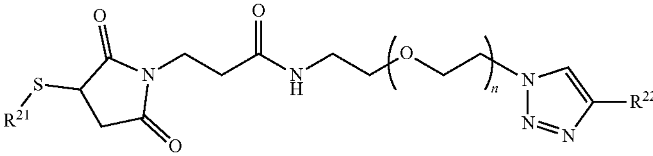 |
| 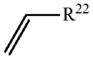 | 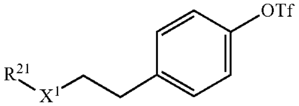 | NH | 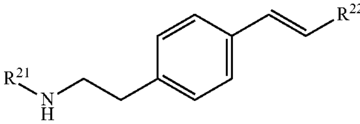 |
| | | O | 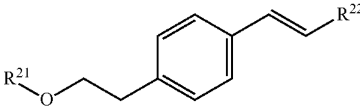 |

TABLE B-continued
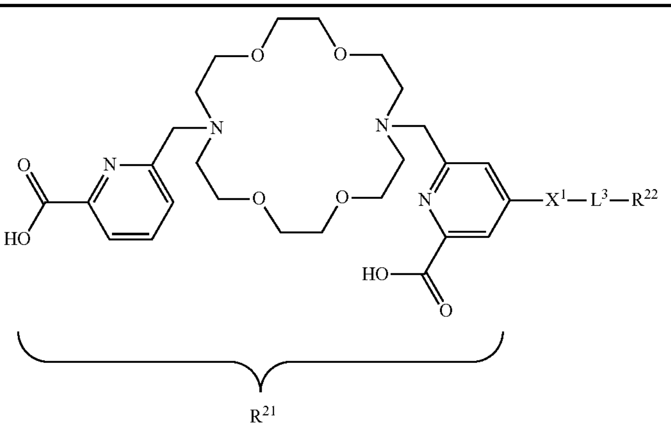
R$^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| 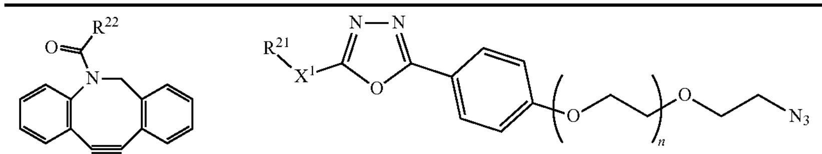 | | S | 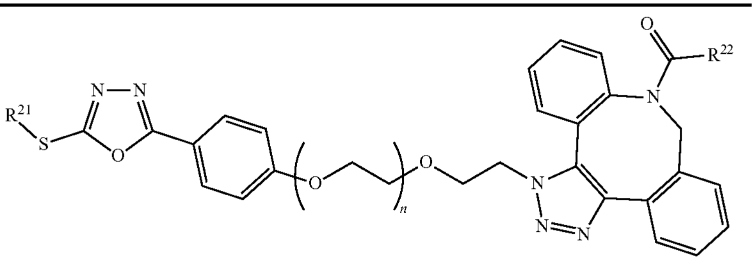 and/or 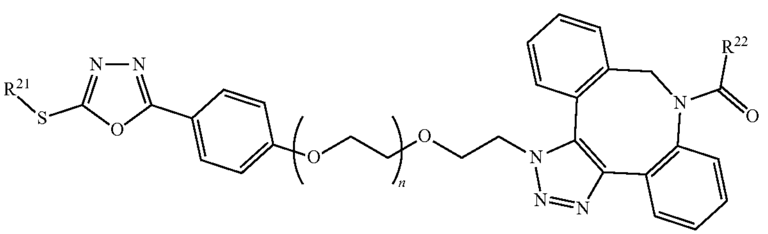 |

TABLE B-continued
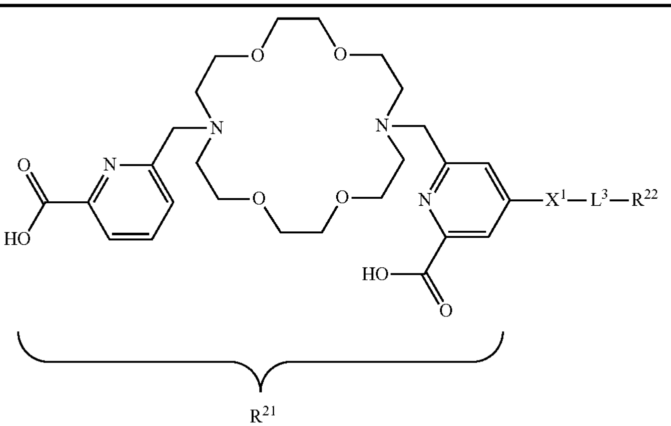
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
| --- | --- | --- | --- |
| 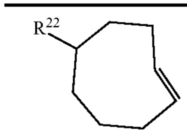 | 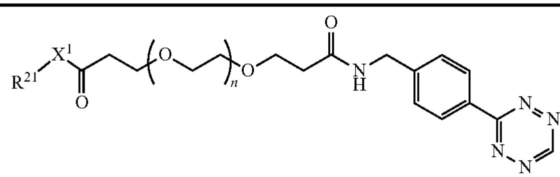 | NH | 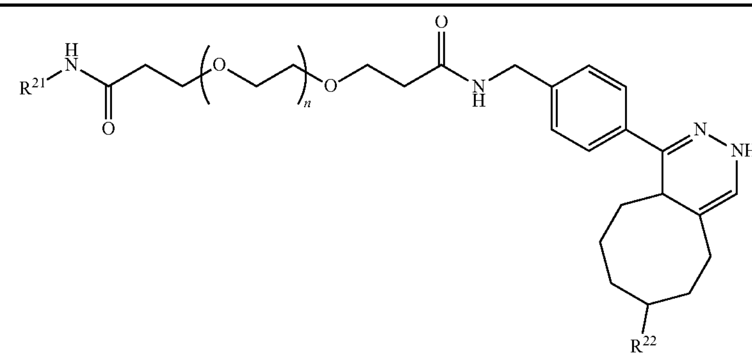 and/or |

TABLE B-continued
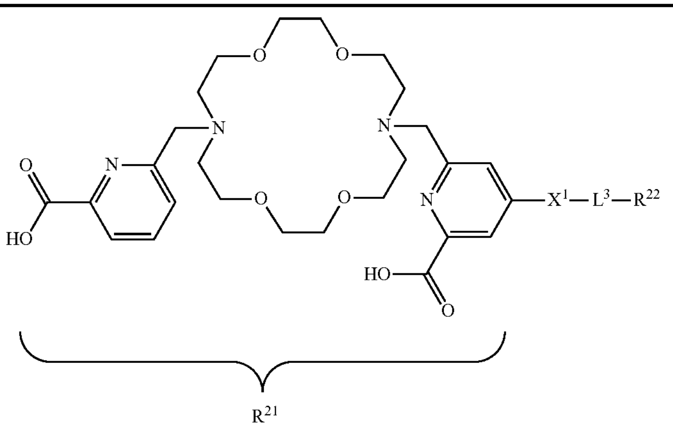
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | | 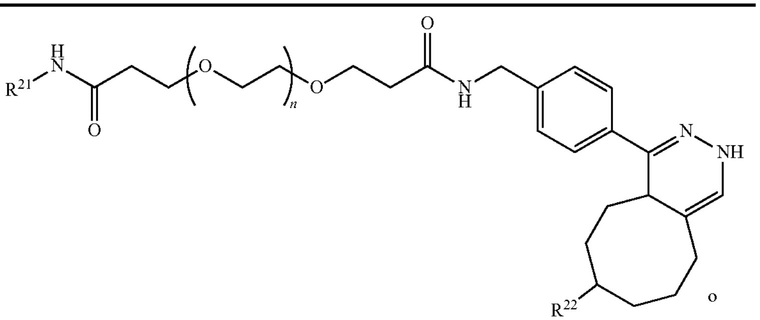 |

TABLE B-continued
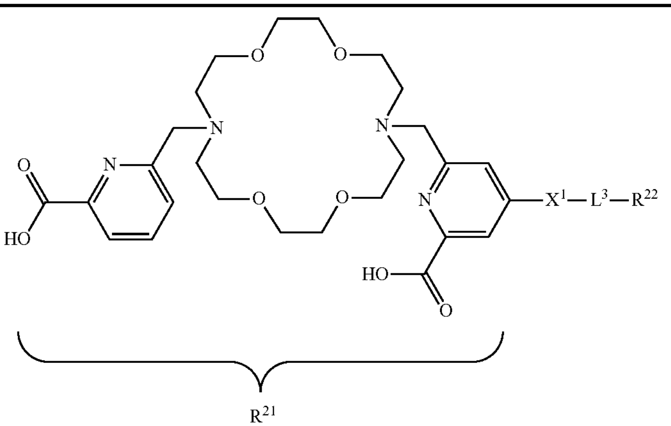
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 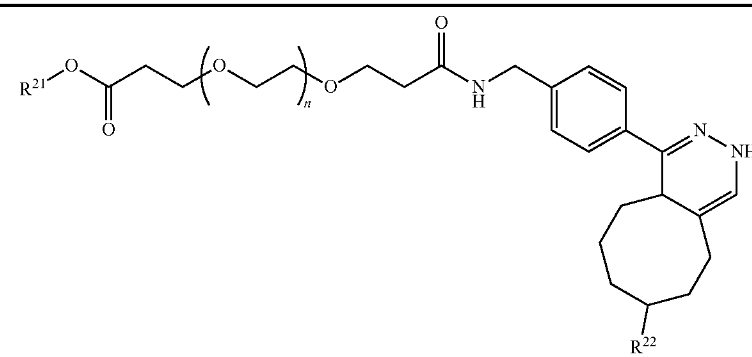 and/or |

TABLE B-continued
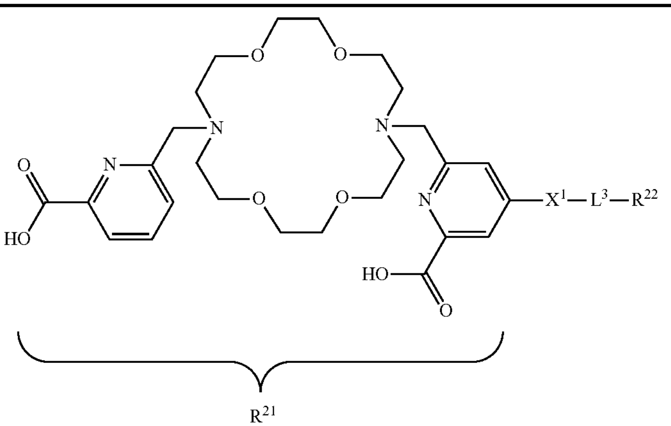
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | | 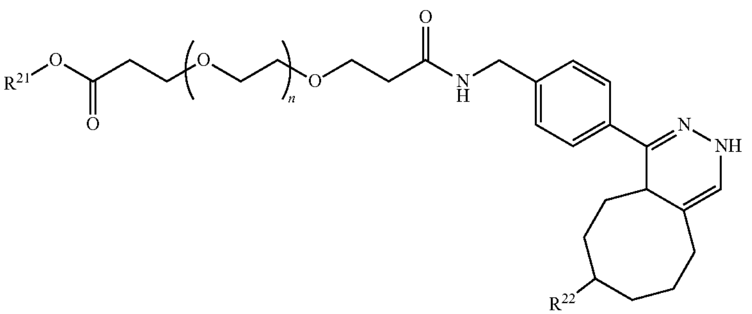 |
| 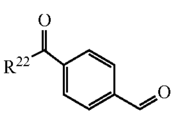 | 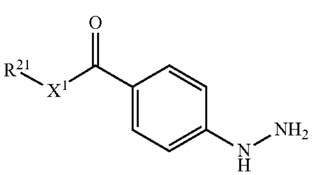 | NH | 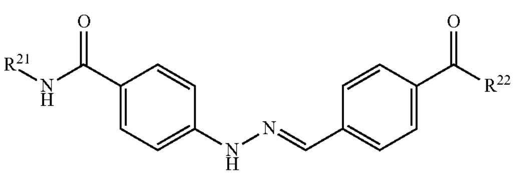 |

TABLE B-continued
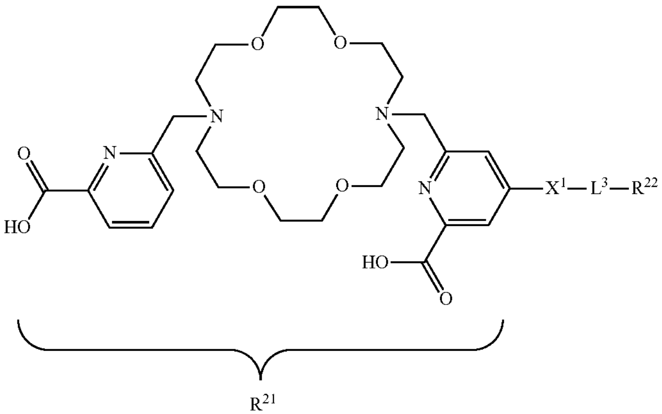
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 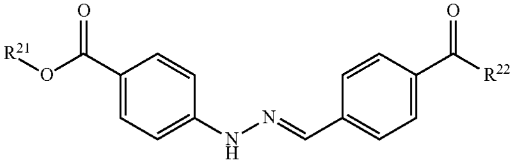 |
| $H_2N$ —$R^{22}$ | 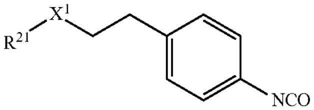 | NH | 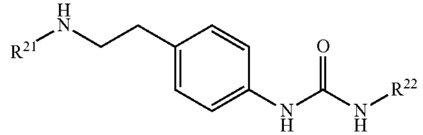 |
| | | O | 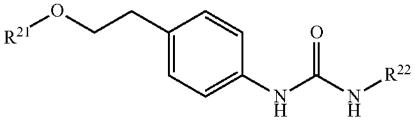 |
| | 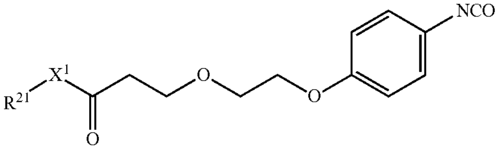 | NH | 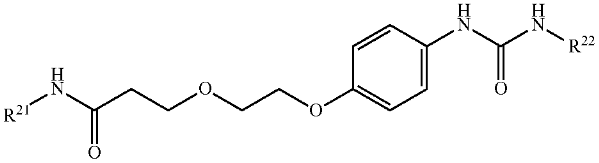 |

TABLE B-continued
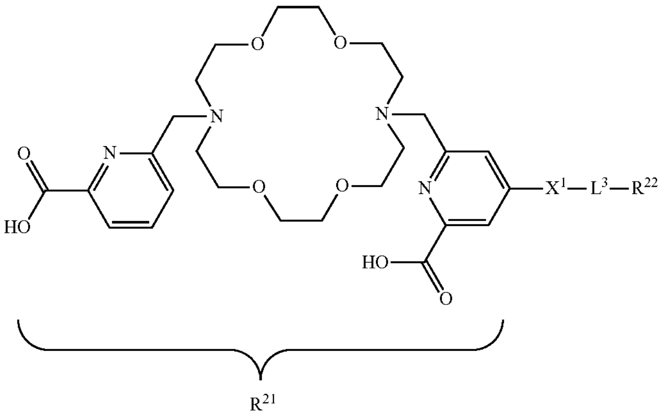
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 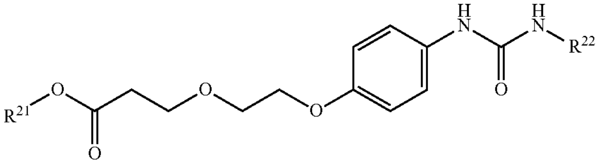 |
| | 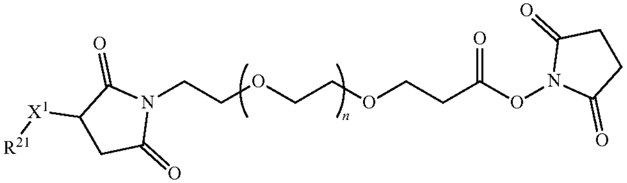 | S | 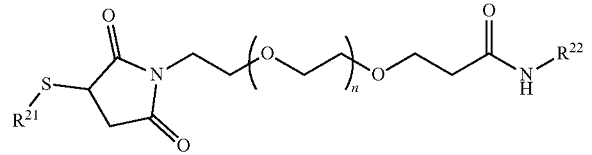 |
| | 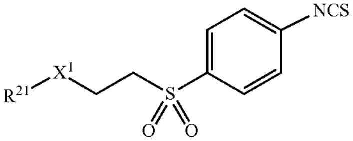 | | 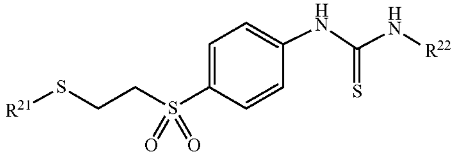 |

TABLE B-continued
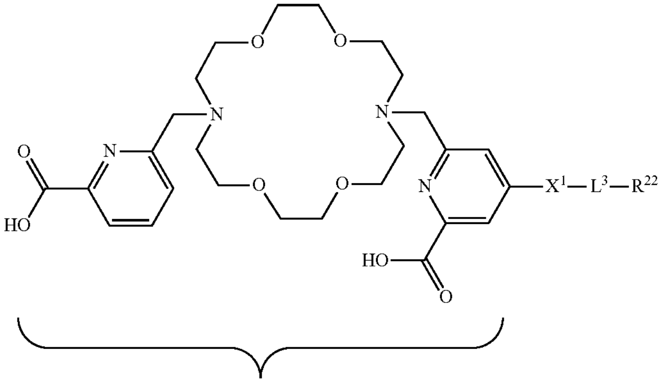
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
| --- | --- | --- | --- |
| 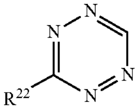 | 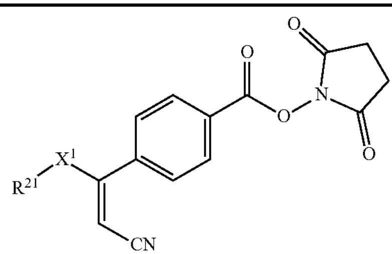 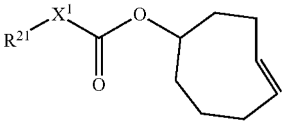 | NH | 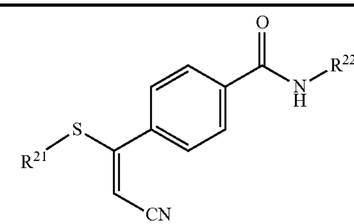 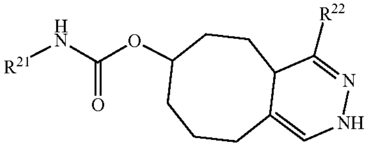 and/or |

TABLE B-continued
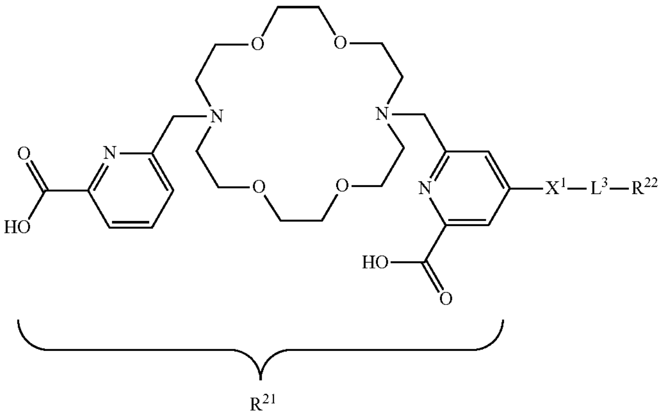
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | O | 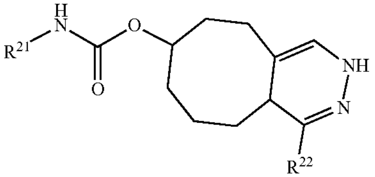 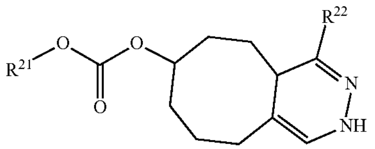 and/or 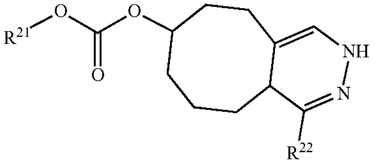 |

TABLE B-continued
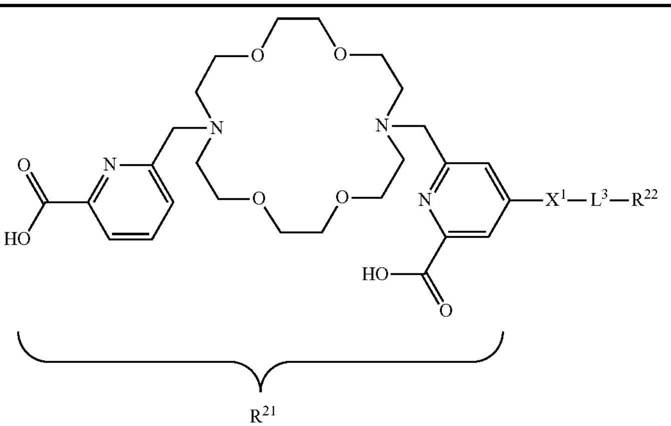
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | 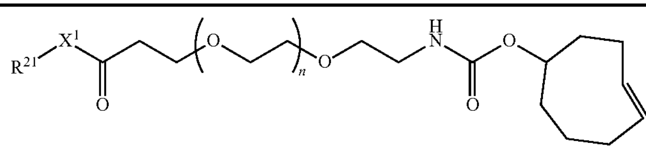 | NH | 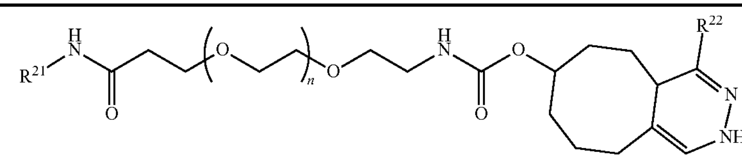 and/or 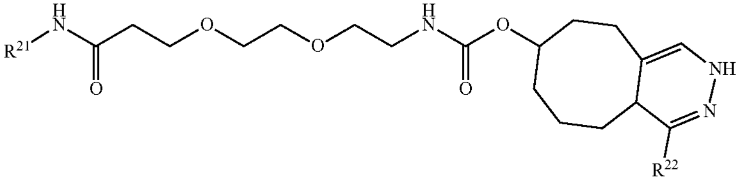 |
| | | O | 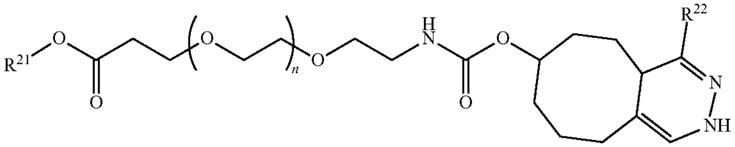 and/or |

TABLE B-continued
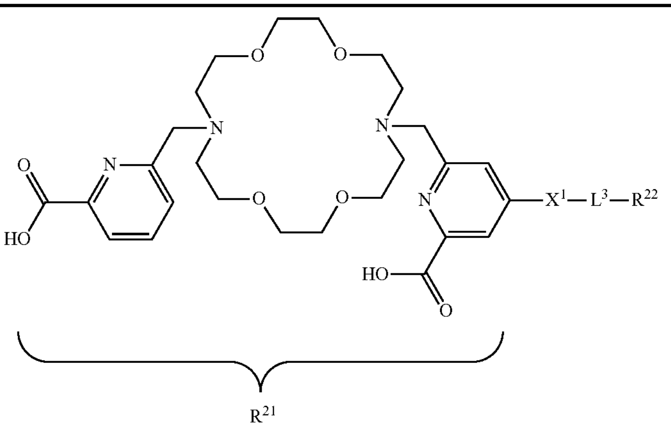
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| | | | 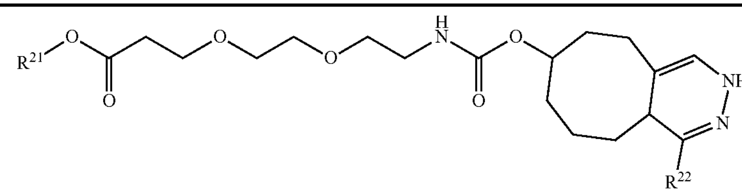 |
| | 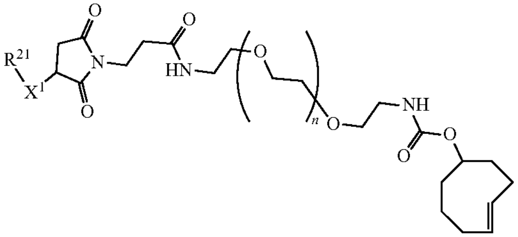 | S | 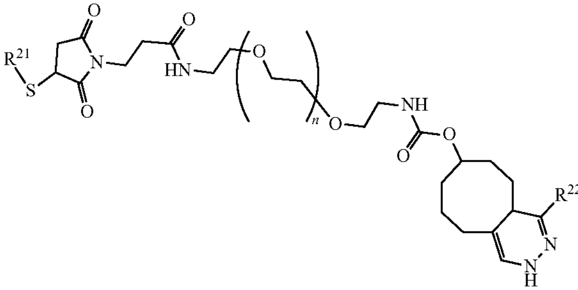 and/or |

TABLE B-continued
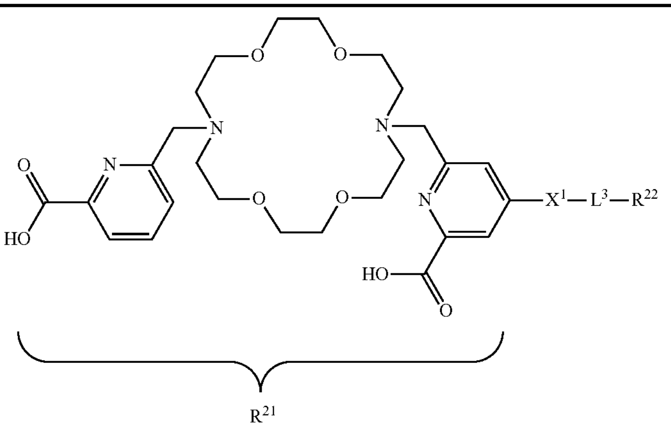
R[21]
| $W^1$-$R^{22}$ | $R^{21}$-$X^1$-$W^2$ | $X^1$ | Final Conjugation Product ($R^{21}$-$X^1$-$L^3$-$R^{22}$) |
| --- | --- | --- | --- |
| | | | 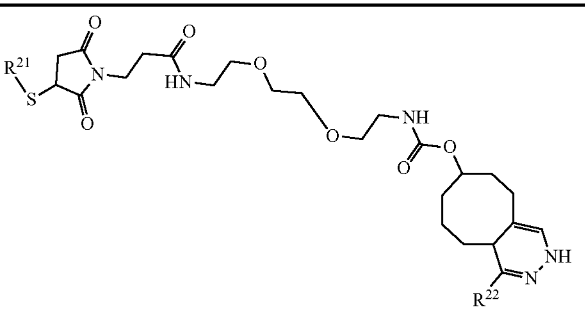 |
| 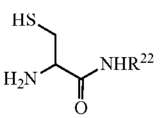 | 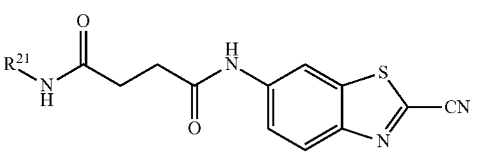 | NH | 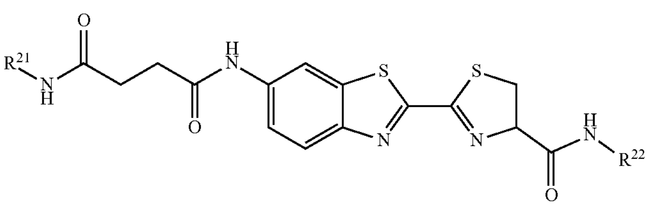 |

TABLE B-continued
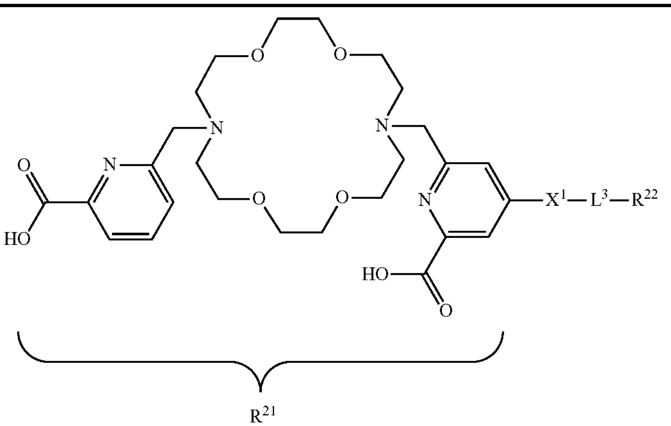
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
| --- | --- | --- | --- |
| | | O | 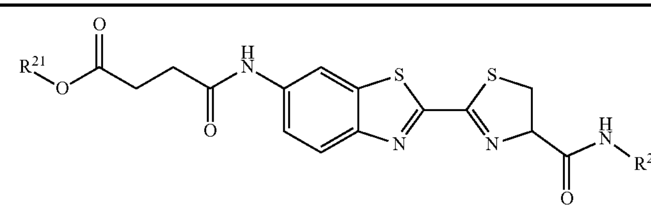 |
| | 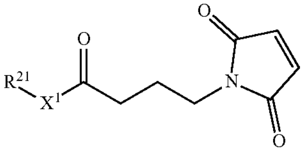 | NH | 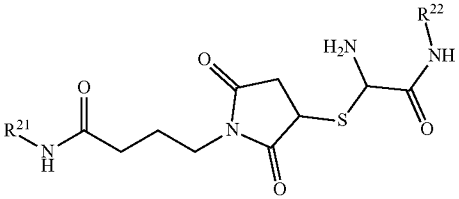 |
| | | O | 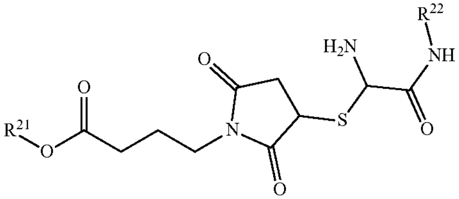 |

TABLE B-continued
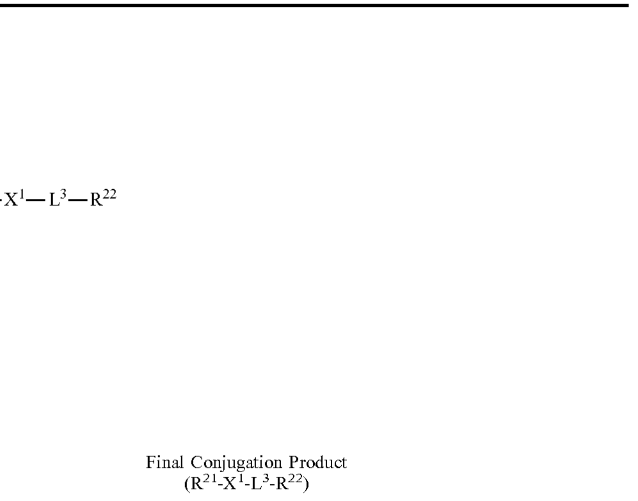
$R^{21}$
| $W^1$-$R^{22}$ | $R^{21}$-$X^1$-$W^2$ | $X^1$ | Final Conjugation Product ($R^{21}$-$X^1$-$L^3$-$R^{22}$) |
|---|---|---|---|
| 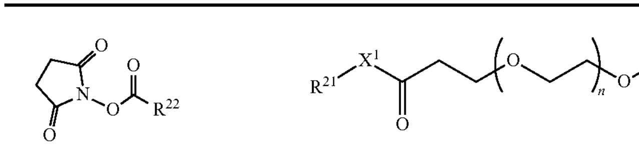 | | NH 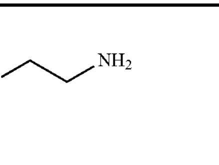 | 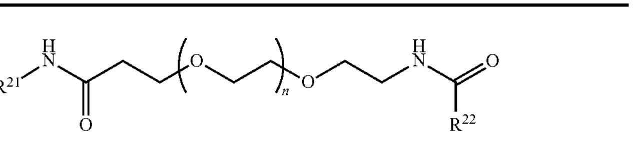 |
| 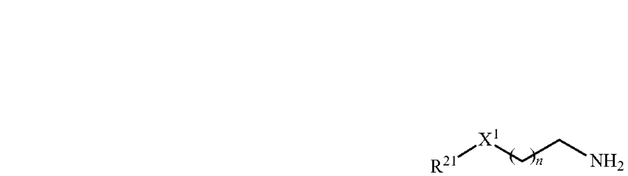 | | O 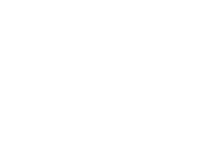 | 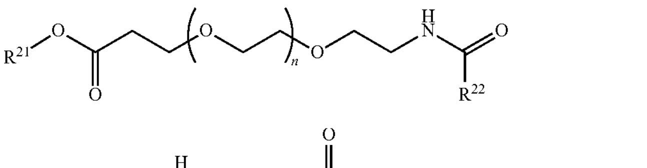 |
| 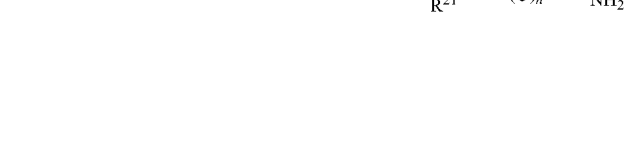 | | NH 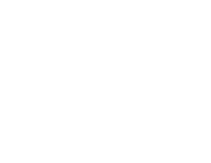 | 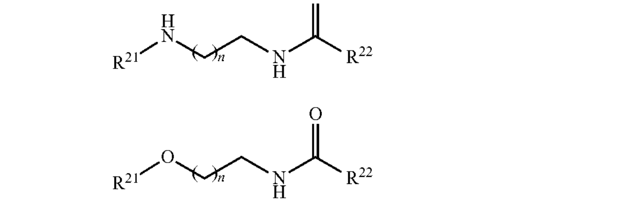 |
| 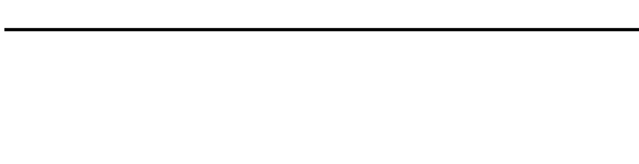 | | O 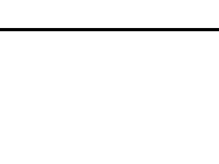 | 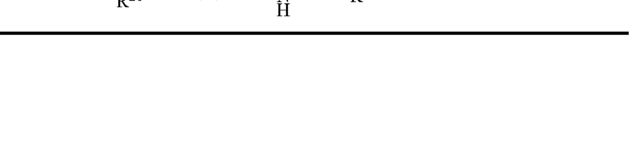 |

In any embodiment herein, it may be that the structures include compounds of Formula VI, a modified antibody, modified antibody fragment, or modified binding peptide comprising a linkage arising from conjugation of a compound of Formula VI or pharmaceutically acceptable salt thereof, with an antibody, antibody fragment, or binding peptide, compounds of Formula VII, a modified antibody, modified antibody fragment, or modified binding peptide comprising a linkage arising from conjugation of a compound of Formula VII or pharmaceutically acceptable salt thereof, with an antibody, antibody fragment, or binding peptide, and targeting compounds of Formula VIII (VI)

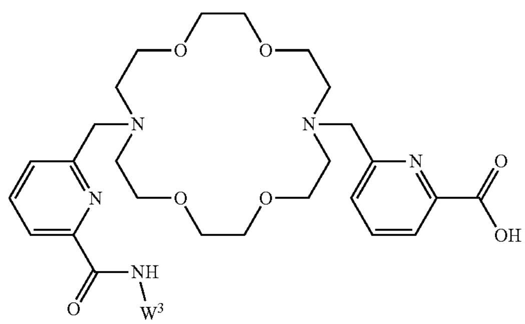

or a pharmaceutically acceptable salt thereof, (VII)

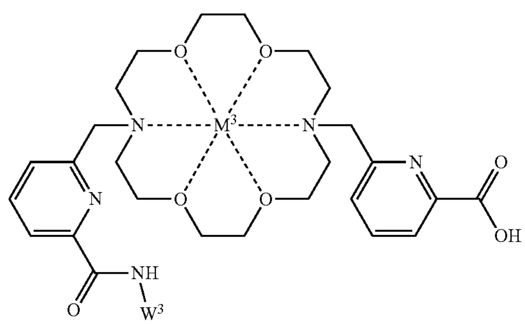

or a pharmaceutically acceptable salt thereof, (VIII)

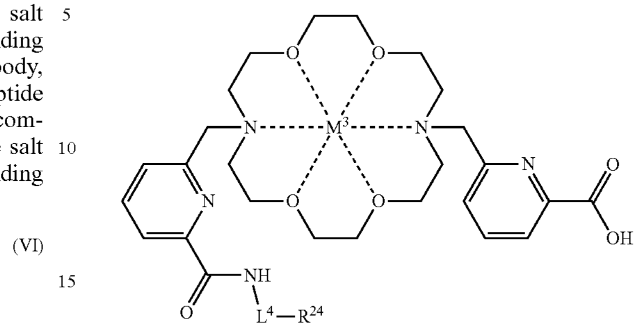

or a pharmaceutically acceptable salt thereof, wherein $M^3$ is independently at each occurrence an alpha-emitting radionuclide.

Targeting compounds of Formula VIII may be prepared by a process that includes reacting a compound of Formula VI or VII with $R^{24}$—$W^4$, where Table C provides representative examples (where n is independently at each occurrence 1, 2, 3, 4, 5, 6, 7, 8, 9, or 10). As such, $R^{24}$ may be conjugated to macrocycle $R^{23}$ by reaction of complementary chemical functional groups $W^3$ and $W^4$ to form linker $L^4$. For example, $R^{24}$—$W^4$ may include a modified target amino acid residue within a protein (e.g., one of the representative antibodies disclosed in Table A or an antigen-binding fragment thereof; a PSMA binding peptide, a somatostatin receptor agonist, a bombesin receptor agonist, a seprase binding compound, or a binding fragment of any one thereof). $W^4$ may include a reactive chemical functional moiety, non-limiting examples of which are disclosed in the Table C, where $W^3$ may be selected to selectively react with $W^4$ in order to provide $L^4$ of Formula VIII.

TABLE C

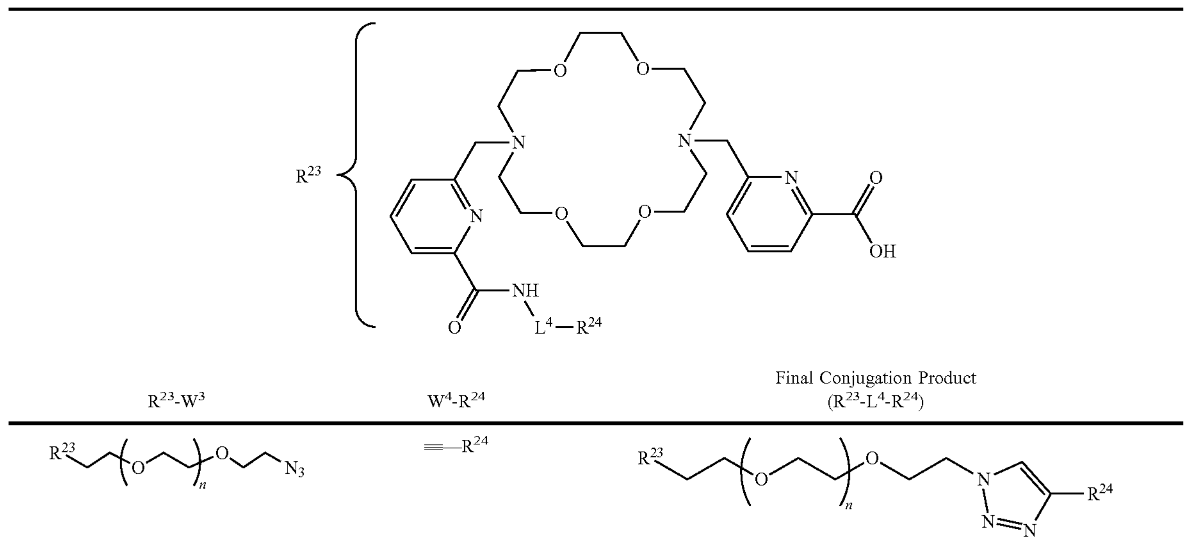

| $R^{23}$-$W^3$ | $W^4$-$R^{24}$ | Final Conjugation Product ($R^{23}$-$L^4$-$R^{24}$) |
| --- | --- | --- |
| | | |

TABLE C-continued
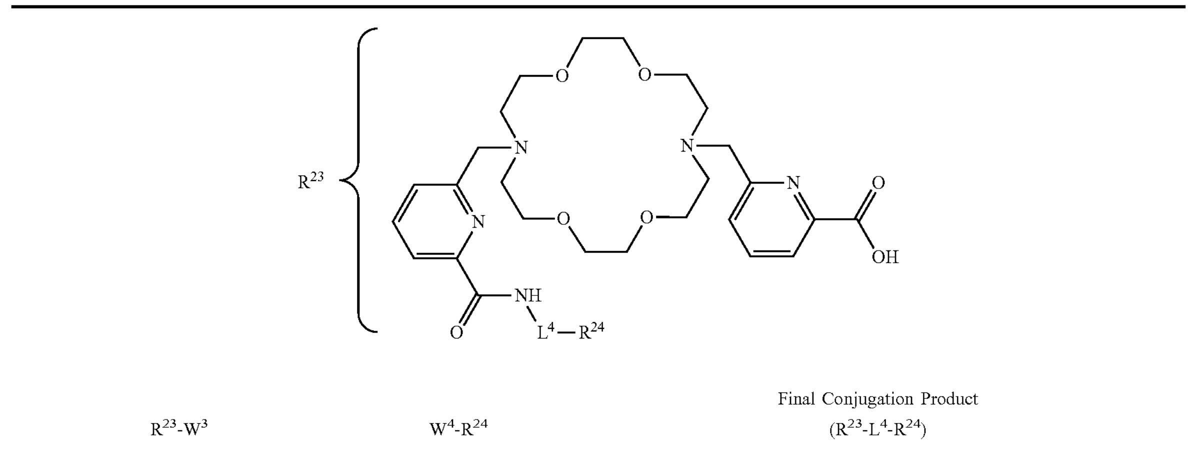
| $R^{23}$-$W^3$ | $W^4$-$R^{24}$ | Final Conjugation Product ($R^{23}$-$L^4$-$R^{24}$) |
|---|---|---|
| | | and/or<br>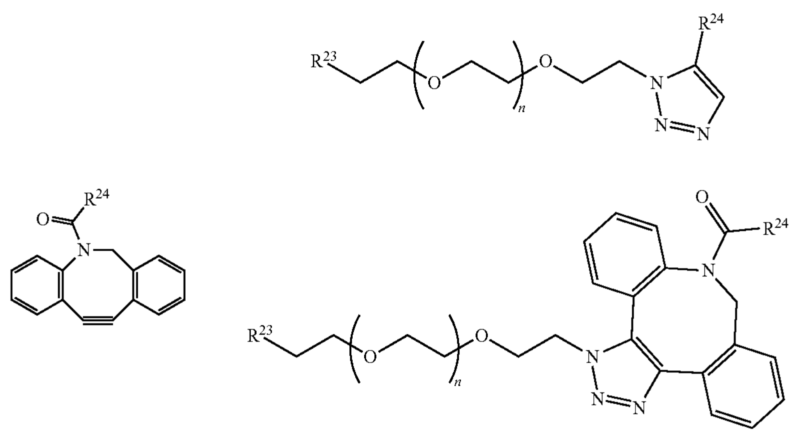<br>and/or<br>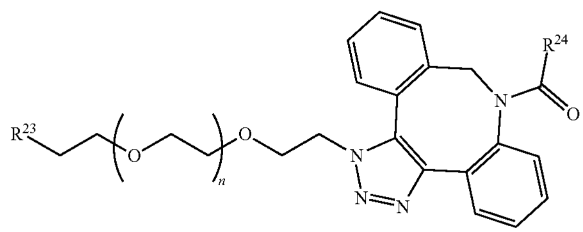 |
| 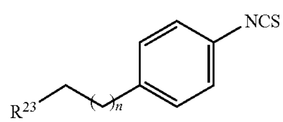 | 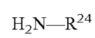 | 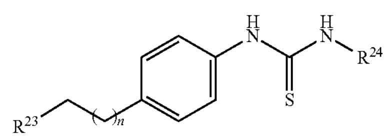 |

TABLE C-continued
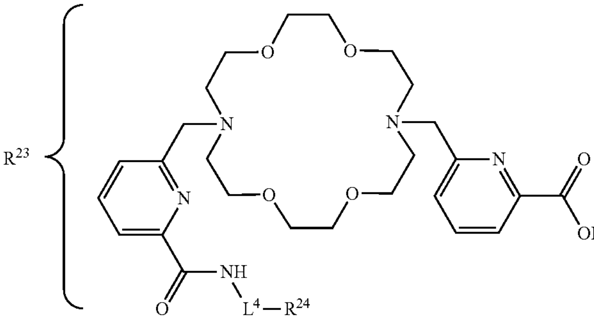
| $R^{23}$-$W^3$ | $W^4$-$R^{24}$ | Final Conjugation Product ($R^{23}$-$L^4$-$R^{24}$) |
|---|---|---|
| 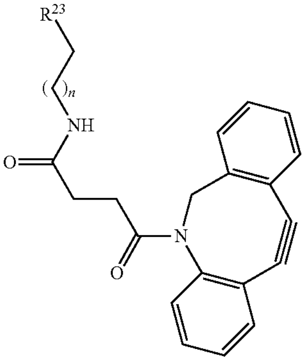 | $N_3$—$R^{24}$ | 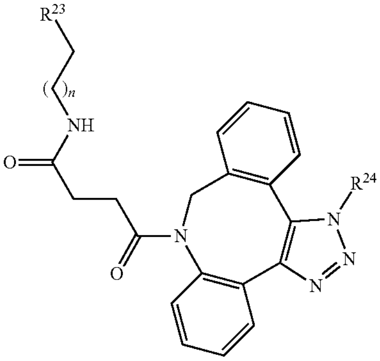 and/or 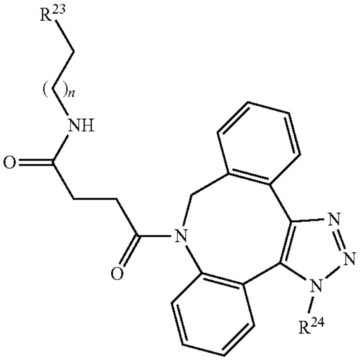 |
| 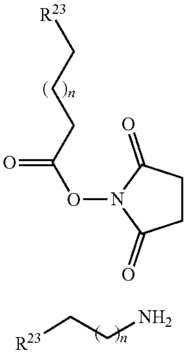 | $H_2N$—$R^{24}$ | 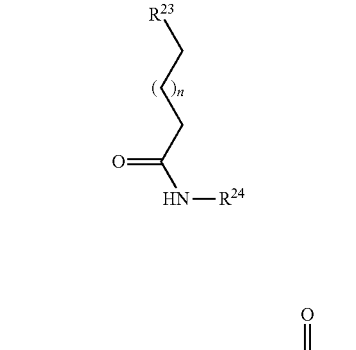 |
| 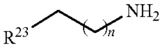 | 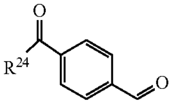 | 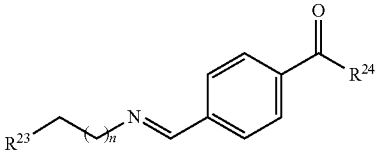 |

TABLE C-continued

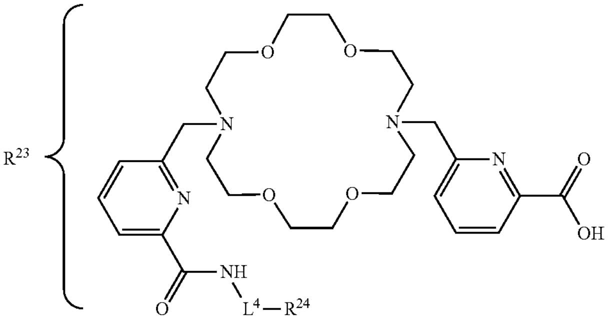

| $R^{23}$-$W^3$ | $W^4$-$R^{24}$ | Final Conjugation Product ($R^{23}$-$L^4$-$R^{24}$) |
|---|---|---|
| | 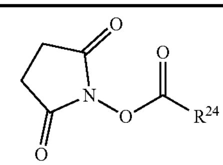 | 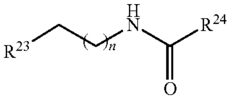 |
| 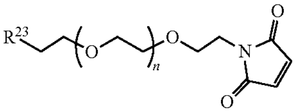 | 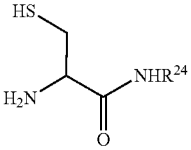 | 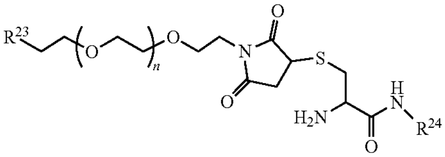 |

In any embodiment herein, it may be that the structures include compounds of Formula IX, a modified antibody, modified antibody fragment, or modified binding peptide comprising a linkage arising from conjugation of a compound of Formula IX or pharmaceutically acceptable salt thereof, with an antibody, antibody fragment, or binding peptide, compounds of Formula X, a modified antibody, modified antibody fragment, or modified binding peptide comprising a linkage arising from conjugation of a compound of Formula X or pharmaceutically acceptable salt thereof, with an antibody, antibody fragment, or binding peptide, and targeting compounds of Formula XI (IX)

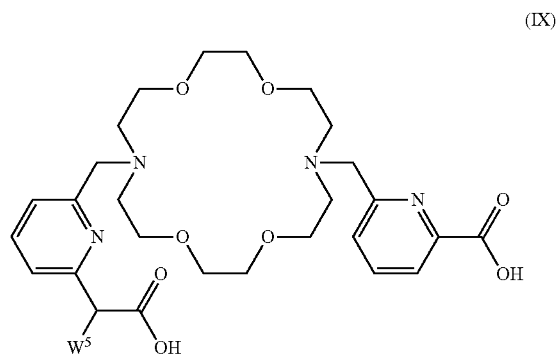

or a pharmaceutically acceptable salt thereof, (X)

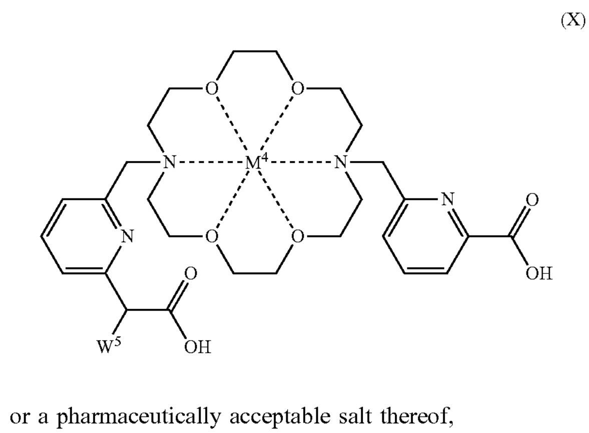

or a pharmaceutically acceptable salt thereof, (XI)

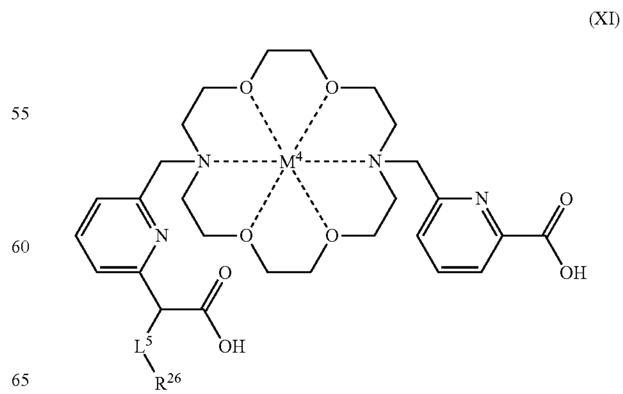

or a pharmaceutically acceptable salt thereof, wherein $M^4$ is independently at each occurrence an alpha-emitting radionuclide.

Targeting compounds of Formula XI may be prepared by a process that includes reacting a compound of Formula IX or X with $R^{26}$—$W^6$, where Table D provides representative examples (where n is independently at each occurrence 1, 2, 3, 4, 5, 6, 7, 8, 9, or 10). As such, $R^{26}$ may be conjugated to macrocycle $R^{25}$ by reaction of complementary chemical functional groups $W^5$ and $W^6$ to form linker $L^5$. For example, $R^{26}$—$W^6$ may include a modified target amino acid residue within a protein (e.g., one of the representative antibodies disclosed in Table A or an antigen-binding fragment thereof; a PSMA binding peptide, a somatostatin receptor agonist, a bombesin receptor agonist, a seprase binding compound, or a binding fragment of any one thereof). $W^6$ may include a reactive chemical functional moiety, non-limiting examples of which are disclosed in the Table D, where $W^5$ may be selected to selectively react with $W^6$ in order to provide $L^5$ of Formula IX.

TABLE D
$R^{25}$ 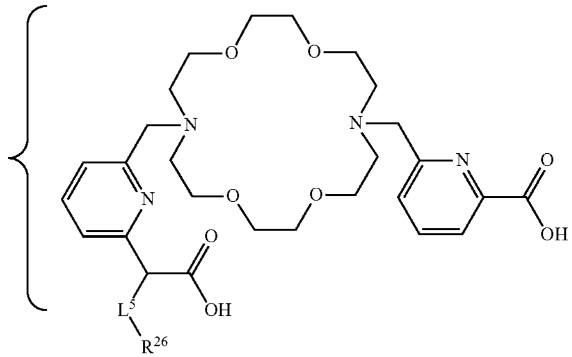
| $R^{25}$-$W^5$ | $W^6$-$R^{26}$ | Final Conjugation Product |
|---|---|---|
| 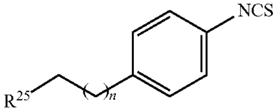 | $H_2N—R^{26}$ | 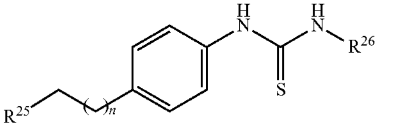 |
| 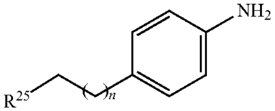 | 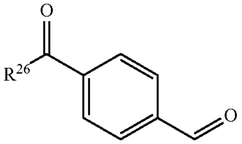 | 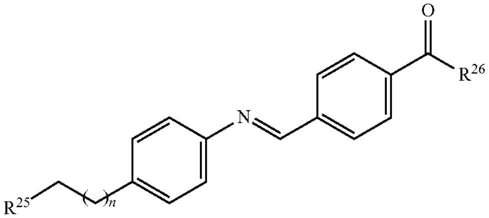 |
| | 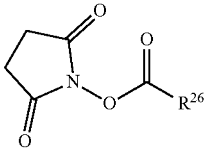 | 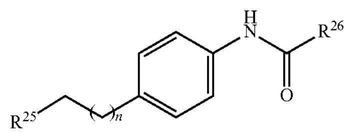 |

TABLE D-continued
| | | |
|---|---|---|
| | 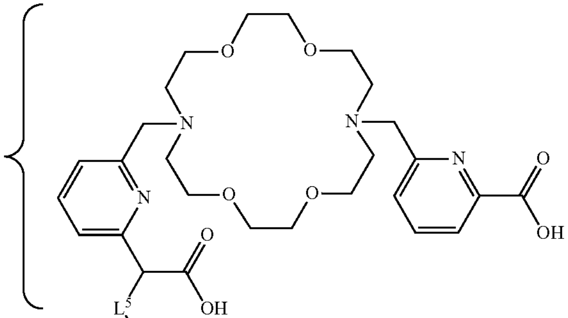 | |
| $R^{25}$-$W^5$ | $W^6$-$R^{26}$ | Final Conjugation Product |
|---|---|---|
| 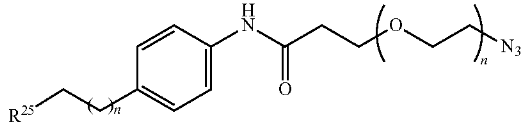 | 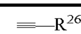 | 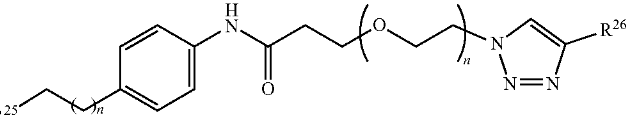 and/or 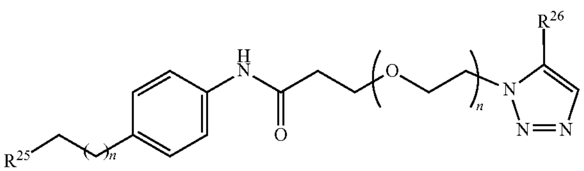 |
| | 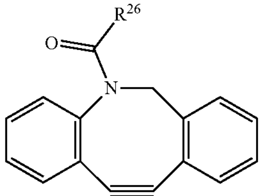 | 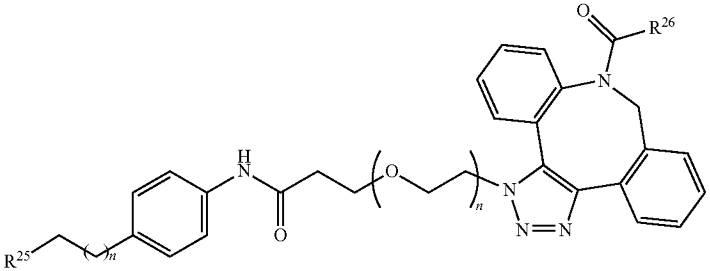 and/or |

TABLE D-continued
| | | |
|---|---|---|
| $R^{25}$ | 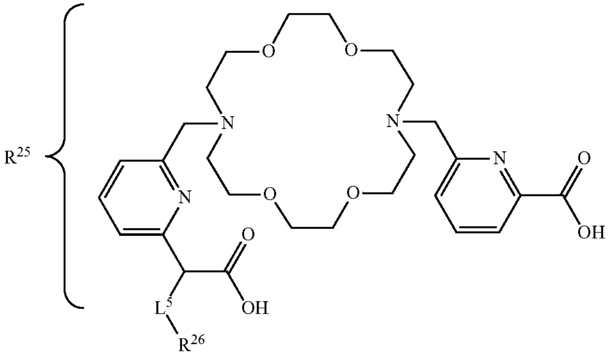 | |
| $R^{25}$-$W^5$ | $W^6$-$R^{26}$ | Final Conjugation Product |
| 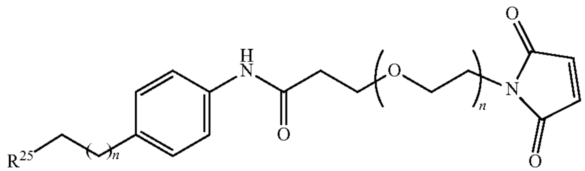 | 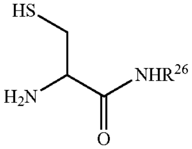 | 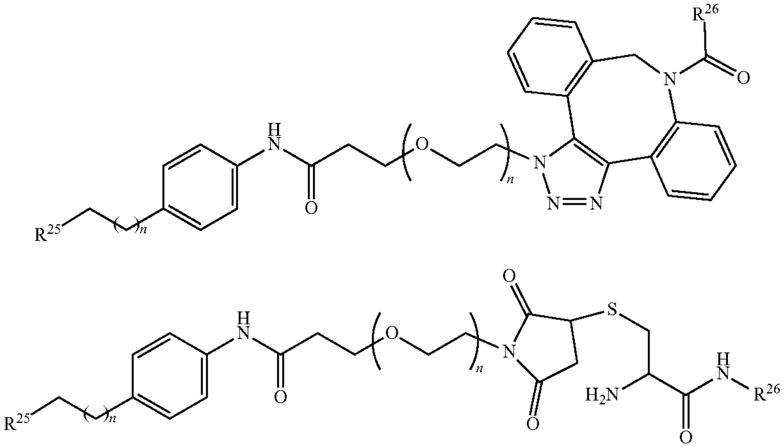 |

In any embodiment herein, it may be that the structures include compounds of Formula XII, a modified antibody, modified antibody fragment, or modified binding peptide comprising a linkage arising from conjugation of a compound of Formula XII or pharmaceutically acceptable salt thereof, with an antibody, antibody fragment, or binding peptide, compounds of Formula XIII, a modified antibody, modified antibody fragment, or modified binding peptide comprising a linkage arising from conjugation of a compound of Formula XIII or pharmaceutically acceptable salt thereof, with an antibody, antibody fragment, or binding peptide, and targeting compounds of Formula XIV (XII)

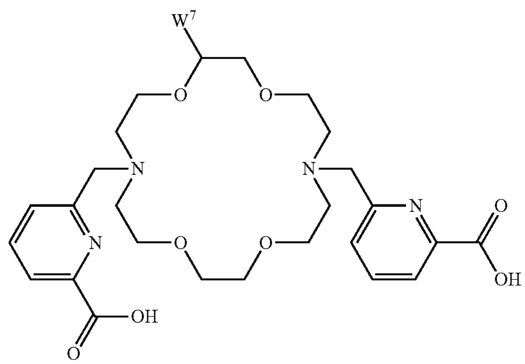

or a pharmaceutically acceptable salt thereof, (XIII)

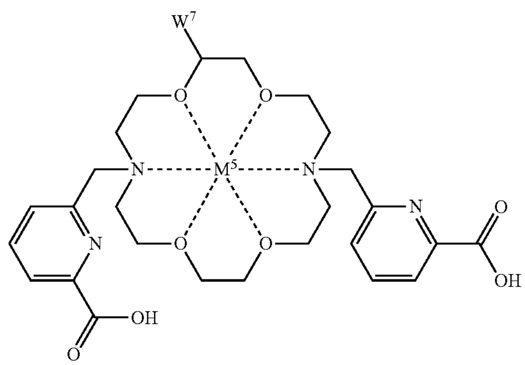

or a pharmaceutically acceptable salt thereof, (XIV)

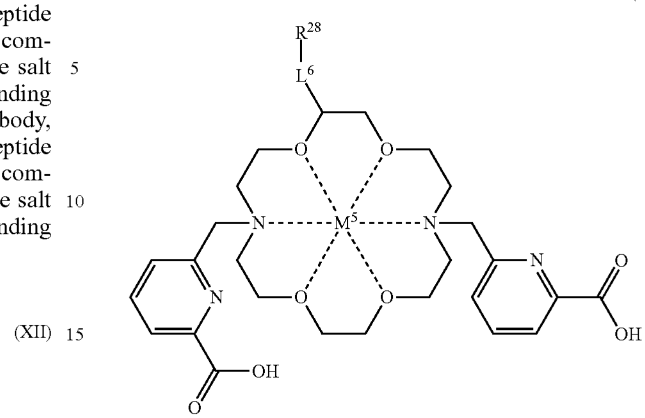

or a pharmaceutically acceptable salt thereof, wherein $M^5$ is independently at each occurrence an alpha-emitting radionuclide.

Targeting compounds of Formula XIV may be prepared by a process that includes reacting a compound of Formula XII or XIII with $R^{28}$—$W^8$, where Table E provides representative examples (where n is independently at each occurrence 1, 2, 3, 4, 5, 6, 7, 8, 9, or 10). As such, $R^{28}$ may be conjugated to macrocycle $R^{27}$ by reaction of complementary chemical functional groups $W^7$ and $W^8$ to form linker $L^4$. For example, $R^{28}$—$W^8$ may include a modified target amino acid residue within a protein (e.g., one of the representative antibodies disclosed in Table A or an antigen-binding fragment thereof; a PSMA binding peptide, a somatostatin receptor agonist, a bombesin receptor agonist, a seprase binding compound, or a binding fragment of any one thereof). $W^8$ may include a reactive chemical functional moiety, non-limiting examples of which are disclosed in the Table E, where $W^7$ may be selected to selectively react with $W^8$ in order to provide $L^6$ of Formula XIV.

TABLE E
R27 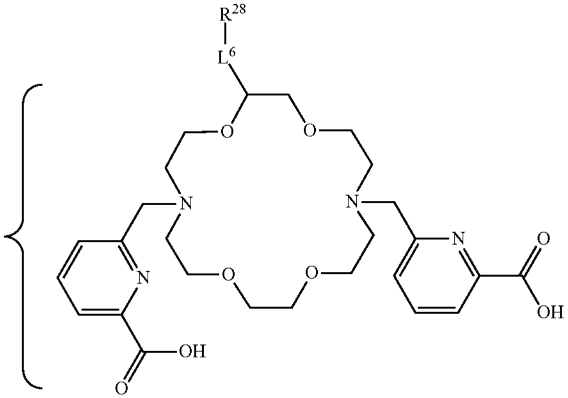
| $R^{27}$-$W^7$ | $W^8$-$R^{28}$ | Final Conjugation Product |
|---|---|---|
| 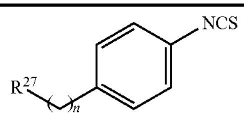 | $H_2N—R^{28}$ | 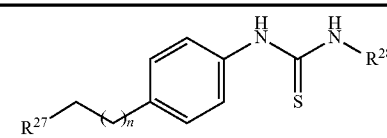 |
| 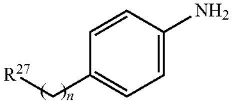 | 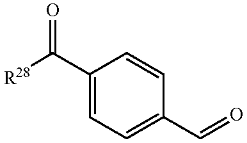 | 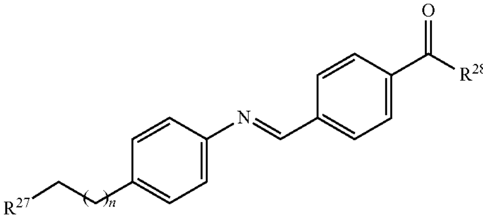 |
| | 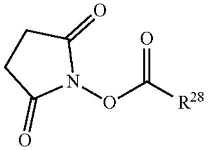 | 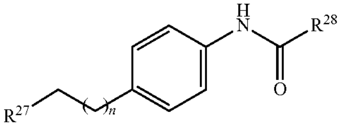 |

TABLE E-continued
| | | |
|---|---|---|
| $R^{27}$ 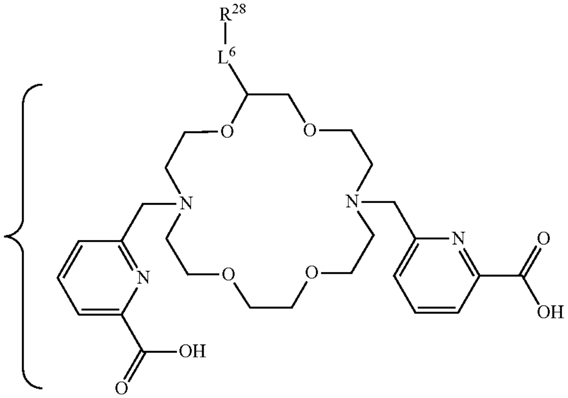 | | |
| $R^{27}$-$W^7$ | $W^8$-$R^{28}$ | Final Conjugation Product |
|---|---|---|
| 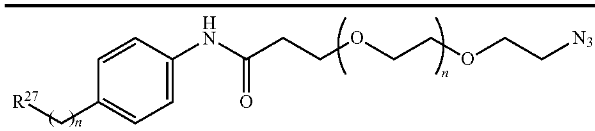 | 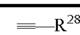 | 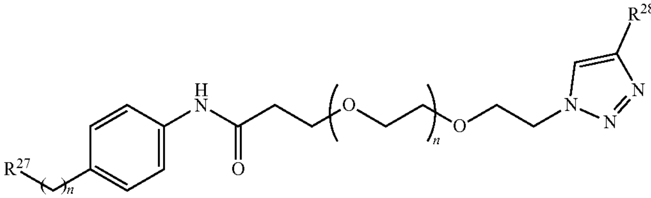 and/or 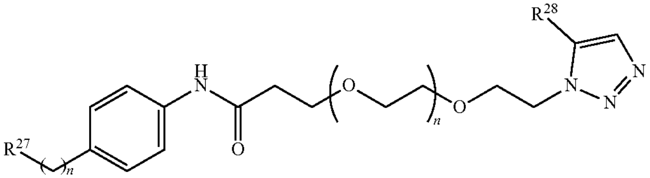 |

TABLE E-continued
$R^{27}$ 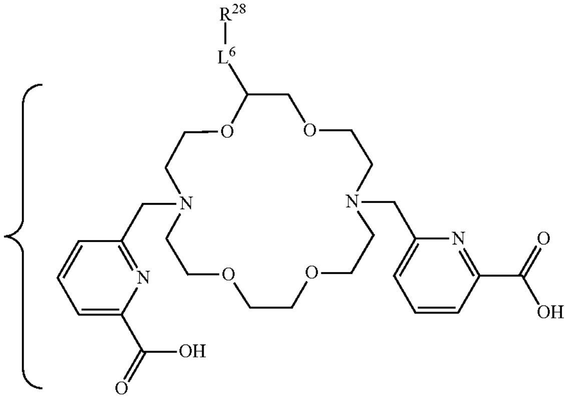
| $R^{27}$-$W^7$ | $W^8$-$R^{28}$ | Final Conjugation Product |
| --- | --- | --- |
| | 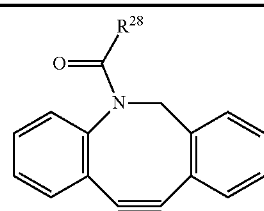 | 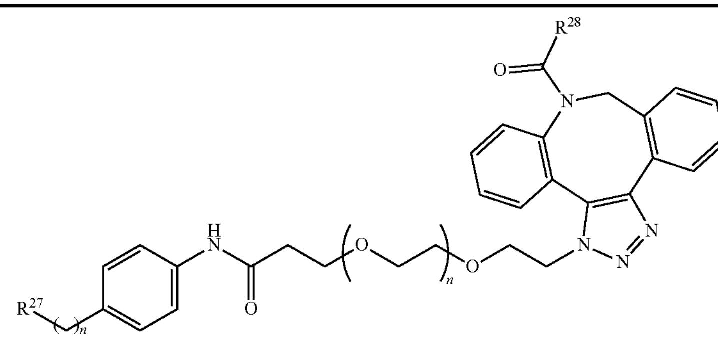 and/or |

TABLE E-continued
R27
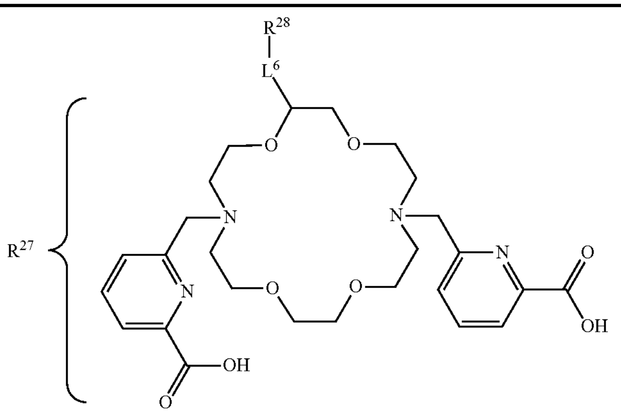
| $R^{27}$-$W^7$ | $W^8$-$R^{28}$ | Final Conjugation Product |
| --- | --- | --- |
| | | 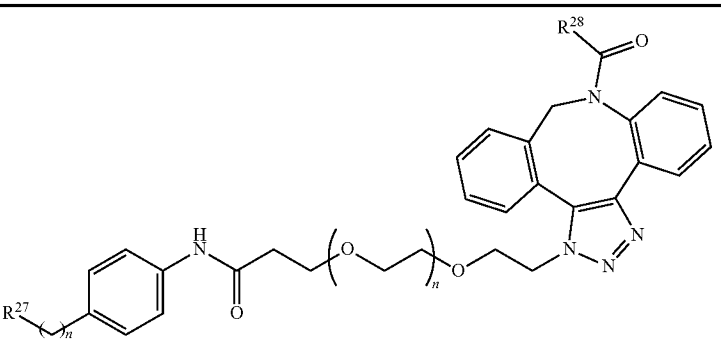 |

A person of ordinary skill in the art will recognize that numerous chemical conjugation strategies provide ready access to targeting compounds of the present technology, whereby exposed amino acid residues on a protein (e.g., an antibody) undergo well-known reactions with reactive moieties on a prosthetic molecule. For example, amide coupling is a well-known route, where—as an example—lysine residues on the antibody surface react with terminal activated carboxylic acid esters to generate stable amide bonds. Amide coupling is typically mediated by any of several coupling reagents (e.g., HATU, EDC, DCC, HOBT, PyBOP, etc.), which are detailed elsewhere. (See generally Eric Valeur & Mark Bradley, *Amide Bond Formation: Beyond the Myth of Coupling Reagents,* 38 CHEM. SOC. REV. 606 (2009).) These and other amide coupling strategies are described in a recent review by Tsuchikama. (Kyoji Tsuchikama & Zhiqiang An, *Antibody-Drug Conjugates: Recent Advances in Conjugation and Linker Chemistries,* 9 PROTEIN CELL 33, 36 (2018); see also, e.g., A. C. Lazar et al., *Analysis of the Composition of Immunoconjugates Using Size-Exclusion Chromatography Coupled to Mass Spectrometry,* 19 RAPID COMMUN. MASS SPECTROM. 1806 (2005).)

Additionally, a person of ordinary skill in the art will recognize that cysteine coupling reactions may be employed to conjugate prosthetic molecules with thiol-reactive termini to protein surfaces through exposed thiol side chains on cysteine residues on the protein (e.g., antibody) surface. (See generally Tsuchikama & An, supra, at 36-37; see also, e.g., Pierre Adumeau et al., *Thiol-Reactive Bifunctional Chelators for the Creation of Site-Selectively Modified Radioimmunoconjugates with Improved Stability,* 29 BIOCONJUGATE CHEM. 1364 (2018).) Because cysteine residues readily form disulfide linkages with nearby cysteine residues under physiological conditions, rather than existing as free thiols, some cysteine coupling strategies may rely upon selective reduction of disulfides to generate a higher number of reactive free thiols. (See id.) Cysteine coupling techniques known in the art include, but are not limited to, cys alkylation reactions, cysteine rebridging reactions, and cys-aryl coupling using organometallic palladium reagents. (See, e.g., C. R. Behrens et al., *Antibody-Drug Conjugates (ADCs) Derived from Interchain Cysteine Cross-Linking Demonstrates Improved Homogeneity and Other Pharmacological Properties Over Conventional Heterogeneous ADCs,* 12 MOL. PHARM. 3986 (2015); Vinogradova et al., *Organometallic Palladium Reagents for Cysteine Bioconjugation,* 526 NATURE 687 (2015); see also Tsuchikama, supra, at 37 (collecting examples).)

Protein conjugation strategies using non-natural amino acid side chains are also well-known in the art. For example, "click chemistries" provide access to conjugated proteins, by rapid and selective chemical transformations under a diverse range of reaction conditions. Click chemistries are known to yield peptide conjugates with limited by-product formation, despite the presence of unprotected functional groups, in aqueous conditions. One important non-limiting example of a click reaction in the formation of conjugated peptides is the copper(I)-catalyzed azide-alkyne 1,3-dipolar cycloaddition reaction (CuAAC). (See Liyuan Liang & Didier Astruc, *The Copper(I)-Catalysed Alkyne-Azide Cycloaddition (CuAAC) "Click" Reaction and Its Applications: An Overview,* 255 COORD. CHEM. REV. 2933 (2011); see also, e.g., Herman S. Gill & Jan Marik, *Preparation of $^{18}F$-labeled Peptides using the Copper(I)-Catalyzed Azide-Alkyne 1,3-Dipolar Cycloxddition,* 6 NATURE PROTOCOLS 1718 (2011).) The CuAAC click reaction may be carried out in the presence of ligands to enhance reaction rates. Such ligands may include, for example, polydentate nitrogen donors, including amines (e.g., tris(triazolyl)methyl amines) and pyridines. (See Liang & Astruc, supra, at 2934 (collecting examples); P. L. Golas et al., 39 MACROMOLECULES 6451 (2006).) Other widely-utilized click reactions include, but are not limited to, thiol-ene, oxime, Diels-Alder, Michael addition, and pyridyl sulfide reactions.

Copper-free (Cu-free) click methods are also known in the art for delivery of therapeutic and/or diagnostic agents, such as radionuclides (e.g., $^{18}F$), chemotherapeutic agents, dyes, contrast agents, fluorescent labels, chemiluminescent labels, or other labels, to protein surfaces. Cu-free click methods may permit stable covalent linkage between target molecules and prosthetic groups. Cu-free click chemistry may include reacting an antibody or antigen-binding fragment, which has been modified with a non-natural amino acid side chain that includes an activating moiety such as a cyclooctyne (e.g., dibenzocyclooctyne (DBCO)), a nitrone or an azide group, with a prosthetic group that presents a corresponding or complementary reactive moiety, such as an azide, nitrone or cyclooctyne (e.g., DBCO). (See, e.g., David. J. Donnelly et al., *Synthesis aid Biologic Evaluation of a Novel $^{18}F$-Labeled Adnectin as a PET Radioligand for Imaging PD-L1 Expression,* 59 J. NUCL. MED. 529 (2018).) For example, where the targeting molecule comprises a cyclooctyne, the prosthetic group may include an azide, nitrone, or similar reactive moiety. Where the targeting molecule includes an azide or nitrone, the prosthetic group may present a complementary cyclooctyne, alkyne, or similar reactive moiety. Cu-free click reactions may be carried out at room temperature, in aqueous solution, in the presence of phosphate-buffered saline (PBS). The prosthetic group may be radiolabeled (e.g., with $^{18}F$) or may be conjugated to any alternative diagnostic and/or therapeutic agent (e.g., a chelating agent). (See id. at 531.)

The compounds of any embodiment and aspect herein of the present technology may be a tripartite compound. However, such tripartite compounds are not restricted to compositions including Formulas I, IA, or II. Thus, in an aspect, a tripartite compound is provided that includes a first domain that has relatively low but still specific affinity for serum albumin (e.g., 0.5 to $50\times10^{-6}$M), a second domain including a chelating moiety such as but not limited to those described herein, and a third domain that includes tumor targeting moiety (TTT) having relatively high affinity for a tumor antigen (e.g., 0.5 to $50\times10^{9}$M). The following exemplary peptide receptors, enzymes, cell adhesion molecules, tumor associated antigens, growth factor receptors and cluster of differentiation antigens are useful targets for constructing the TTT domain: somatostatin peptide receptor-2 (SSTR2), gastrin-releasing peptide receptor, seprase (FAP-alpha), incretin receptors, glucose-dependent insulinotropic polypeptide receptors, VIP-1, NPY, folate receptor, LHRH, and $\alpha v\beta 3$, an overexpressed peptide receptor, a neuronal transporter (e.g., noradrenaline transporter (NET)), or other tumor associated proteins such as EGFR, HER-2, VGFR, MUC-1, CEA, MUC-4, ED2, TF-antigen, endothelial specific markers, neuropeptide Y, uPAR, TAG-72, CCK analogs, VIP, bombesin, VEGFR, tumor-specific cell surface proteins, GLP-1, CXCR4, Hepsin, TMPRSS2, caspases, Alpha V beta six, cMET. Other such targets will be apparent to those of skill in the art, and compounds that bind these can be incorporated in the TTT to produce a tripartite radiotherapeutic compound.

The following Formulas L-LIV provide exemplary general structures for tripartite compounds of the present technology.

(L)

(LI)

(LII)

(LIII)

(LIV)

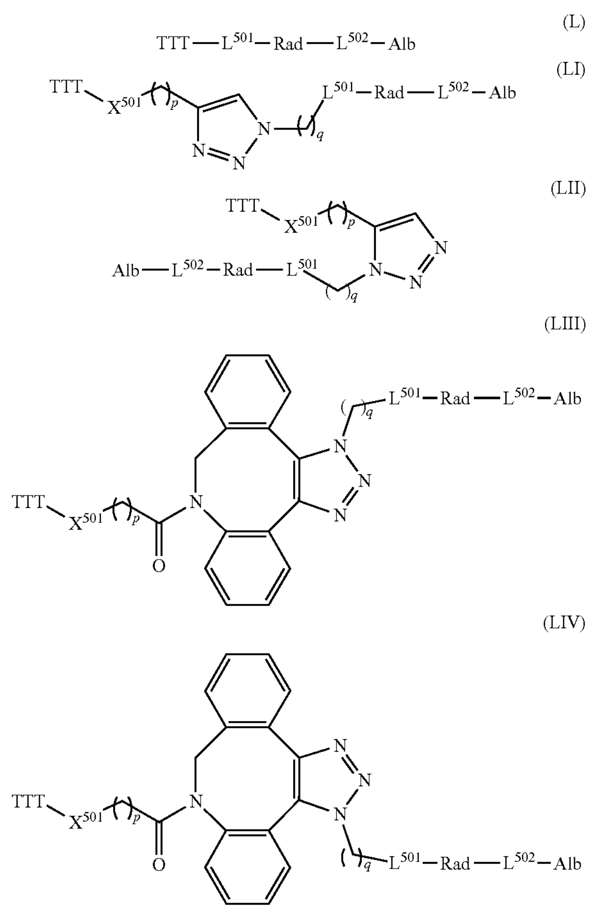

where

TTT is independently at each occurrence a binding domain for a somatostatin peptide receptor-2 (SSTR2), a gastrin-releasing peptide receptor, a seprase (FAP-alpha), an incretin receptor, a glucose-dependent insulinotropic polypeptide receptor, VIP-1, NPY, a folate receptor, LHRH, αvβ3, an overexpressed peptide receptor, a neuronal transporter (e.g., noradrenaline transporter (NET)), a receptor for a tumor associated protein (such as EGFR, HER-2, VGFR, MUC-1, CEA, MUC-4, ED2,TF-antigen, endothelial specific markers, neuropeptide Y, uPAR, TAG-72, CCK analogs, VIP, bombesin, VEGFR, tumor-specific cell surface proteins, GLP-1, CXCR4, Hepsin, TMPRSS2, caspases, Alpha V beta six, cMET, or combination of any two or more thereof), or a combination of any two or more thereof;

$X^{501}$ is independently at each occurrence absent, O, S, or NH;

$L^{501}$ is independently at each occurrence absent, —C(O)—, —C(O)—$NR^4$—, —C(O)—$NR^5$—$C_1$-$C_{12}$ alkylene-, —$C_1$-$C_{12}$ alkylene-C(O)—, —C(O)—$NR^6$—$C_1$-$C_{12}$ alkylene-C(O)—, -arylene-, —$O(CH_2CH_2O)_r$—$CH_2CH_2C(O)$—, —$O(CH_2CH_2O)_{rr}$—$CH_2CH_2C(O)$—NH—, —$O(CH_2CH_2O)_{rrr}$—$CH_2CH_2$—, an amino acid, a peptide of 2, 3, 4, 5, 6, 7, 8, 9, or 10 amino acids, or a combination of any two or more thereof, where r is 0, 1, 2, 3, 4, 5, 6, 7, 8, or 9, rr is 0, 1, 2, 3, 4, 5, 6, 7, 8, or 9, rrr is 0, 1, 2, 3, 4, 5, 6, 7, 8, or 9, and where $R^4$, $R^5$, and $R^6$ are each independently H, alkyl, or aryl;

Rad is independently at each occurrence a moiety capable of including a radionuclide, optionally further including a radionuclide;

$L^{502}$ is independently at each occurrence absent, —C(O)—, —$(CH_2CH_2O)_s$—$CH_2CH_2C(O)$—, —$(CH_2CH_2O)_{ss}$—$CH_2CH_2C(O)$—NH—, —$(CH_2CH_2O)_{sss}$—$CH_2CH_2$—, an amino acid, —$CH(CO_2H)$—$(CH_2)_4$—, —$CH(CO_2H)$—$(CH_2)_4$—NH—, a peptide of 2, 3, 4, 5, 6, 7, 8, 9, 10, 11, 12, 13, 14, 15, 16, 17, 18, 19, or 20 amino acids, or a combination of any two or more thereof, where s is 0, 1, 2, 3, 4, 5, 6, 7, 8, 9, 10, 11, 12, 13, 14, 15, 16, 17, 18, or 19, ss is 0, 1, 2, 3, 4, 5, 6, 7, 8, 9, 10, 11, 12, 13, 14, 15, 16, 17, 18, or 19, and sss is 0, 1, 2, 3, 4, 5, 6, 7, 8, 9, 10, 11, 12, 13, 14, 15, 16, 17, 18, or 19;

Alb is independently at each occurrence an albumin-binding moiety;

p is independently at each occurrence 0, 1, 2, or 3; and q is independently at each occurrence 1 or 2.

In any embodiment disclosed herein, the radionuclide may be $^{177}Lu^{3+}$, $^{175}Lu^{3+}$, $^{45}Sc^{3+}$, $^{66}Ga^{3+}$, $^{67}Ga^{3+}$, $^{68}Ga^{3+}$, $^{69}Ga^{3+}$, $^{71}Ga^{3+}$, $^{89}Yy^{3+}$, $^{86}Y^{3+}$, $^{89}Zr^{4+}$, $^{90}Y^{3+}$, $^{99m}Tc^{+1}$, $^{111}In^{3+}$, $^{113}In^{3+}$, $^{115}In^{3+}$, $^{139}La^{3+}$, $^{136}Ce^{3+}$, $^{138}Ce^{3+}$, $^{140}Ce^{3+}$, $^{142}Ce^{3+}$, $^{151}Eu^{3+}$, $^{153}Eu^{3+}$, $^{152}Dy^{3+}$, $^{149}Tb^{3+}$, $^{159}Tb^{3+}$, $^{154}Gd^{3+}$, $^{155}Gd^{3+}$, $^{156}Gd^{3+}$, $^{157}Gd^{3+}$, $^{158}Gd^{3+}$, $^{160}Gd^{3+}$, $^{186}Re^{+1}$, $^{213}Re^{+1}$, $^{213}Bi^{3+}$, $^{211}At^{+}$, $^{217}At^{+}$, $^{227}Th^{4+}$, $^{226}Th^{4+}$, $^{225}Ac^{3+}$, $^{233}Ra^{2+}$, $^{152}Dy^{3+}$, $^{213}Bi^{3+}$, $^{212}Bi^{3+}$, $^{211}Bi^{3+}$, $^{212}Pb^{2+}$, $^{212}Pb^{4+}$, $^{255}Fm^{3+}$, or uranium-230. For example, the the radionuclide may be an alpha-emitting radionuclide such as $^{213}Bi^{3+}$, $^{213}At^{+}$, $^{225}Ac^{3+}$, $^{152}Dy^{3+}$, $^{212}Bi^{3+}$, $^{211}Bi^{3+}$, $^{217}At^{+}$, $^{227}Tb^{4+}$, $^{226}Th^{4+}$, $^{233}Ra^{2+}$, $^{212}Pb^{2+}$, or $^{212}Pb^{4+}$.

In any embodiment disclosed herein, it may be the tripartite compounds of Formulas L-LIV are of Formulas LV-LIX (LV)

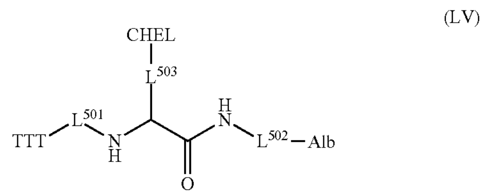

(LVI)

(LVII)

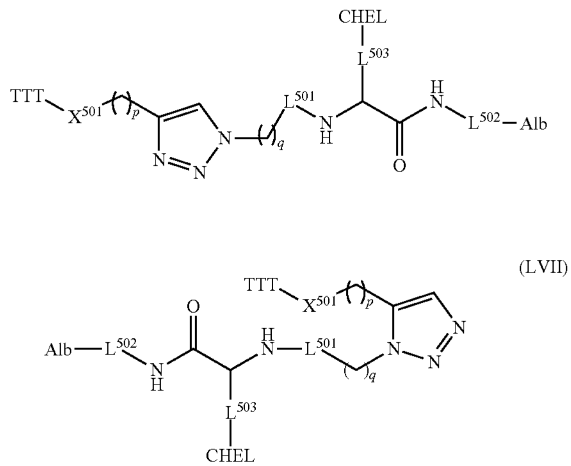

-continued (LVIII)

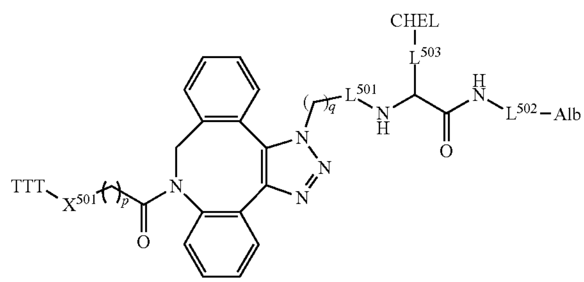

(LIX)

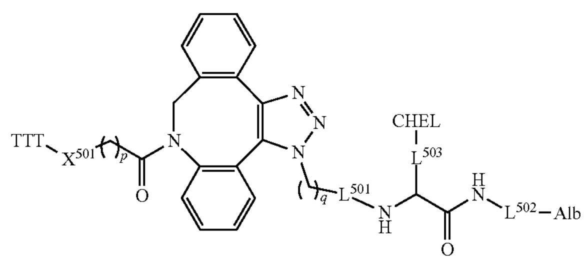

where $L^{503}$ is independently at each occurrence absent, —C(O)—, —$C_1$-$C_{12}$ alkylene-, —$C_1$-$C_{12}$ alkylene-C(O)—, —$C_1$-$C_{12}$ alkylene-$NR^{10}$—, -arylene-, —$(CH_2CH_2O)_z$—$CH_2CH_2C(O)$—, —$(CH_2CH_2O)_{zz}$—$CH_2CH_2C(O)$—NH—, —$(CH_2CH_2O)_{zzz}$—$CH_2CH_2$—, an amino acid, —CH$(CO_2H)$—$(CH_2)_4$—, —CH$(CO_2H)$—$(CH_2)_4$—NH—, a peptide of 2, 3, 4, 5, 6, 7, 8, 9, 10, 11, 12, 13, 14, 15, 16, 17, 18, 19, or 20 amino acids, or a combination of any two or more thereof, where z is 0, 1, 2, 3, 4, 5, 6, 7, 8, 9, 10, 11, 12, 13, 14, 15, 16, 17, 18, or 19, zz is 0, 1, 2, 3, 4, 5, 6, 7, 8, 9, 10, 11, 12, 13, 14, 15, 16, 17, 18, or 19, and zzz is 0, 1, 2, 3, 4, 5, 6, 7, 8, 9, 10, 11, 12, 13, 14, 15, 16, 17, 18, or 19; and CHEL is independently at each occurrence a covalently conjugated chelator that optionally includes a chelated radionuclide.

The albumin-binding moiety plays a role in modulating the rate of blood plasma clearance of the compounds in a subject, thereby increasing circulation time and compartmentalizing the cytotoxic action of cytotoxin-containing domain and/or imaging capability of the imaging agent-containing domain in the plasma space instead of normal organs and tissues that may express antigen. Without being bound by theory, this component of the structure is believed to interact reversibly with serum proteins, such as albumin and/or cellular elements. The affinity of this albumin-binding moiety for plasma or cellular components of the blood may be configured to affect the residence time of the compounds in the blood pool of a subject. In any embodiment herein, the albumin binding-moiety may be configured so that it binds reversibly or non-reversibly with albumin when in blood plasma. In any embodiment herein, the albumin binding-moiety may be selected such that the binding affinity of the compound with human serum albumin is about 5 μM to about 15 μM.

By way of example, the albumin-binding moiety of any embodiment herein may include a short-chain fatty acid, medium-chain chain fatty acid, a long-chain fatty acid, myristic acid, a substituted or unsubstituted indole-2-carboxylic acid, a substituted or unsubstituted 4-oxo-4-(5,6,7,8-tetrahydronaphthalen-2-yl)butanoic acid, a substituted or unsubstituted naphthalene acylsulfonamide, a substituted or unsubstituted diphenylcyclohexanol phosphate ester, a substituted or unsubstituted 2-(4-iodophenyl)acetic acid, a substituted or unsubstituted 3-(4-iodophenyl)propionic acid, or a substituted or unsubstituted 4-(4-iodophenyl)butanoic acid. Certain representative examples of albumin-binding moieties that may be included in any embodiment herein include one or more of the following:

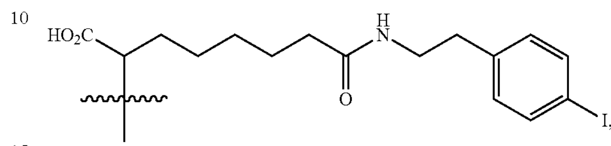

,

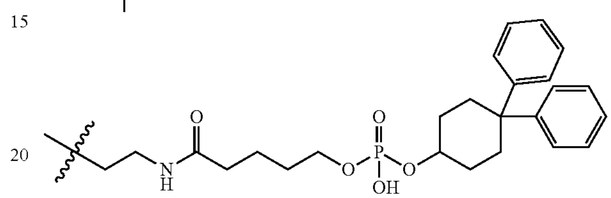

,

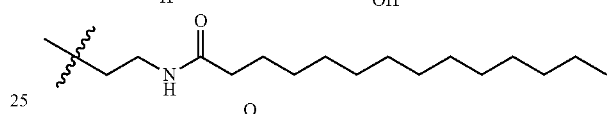

,

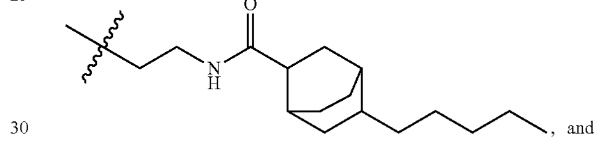

, and

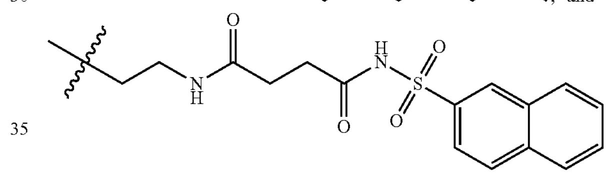

.

In any embodiment herein, the tripartite compounds may include an albumin-binding moiety that is

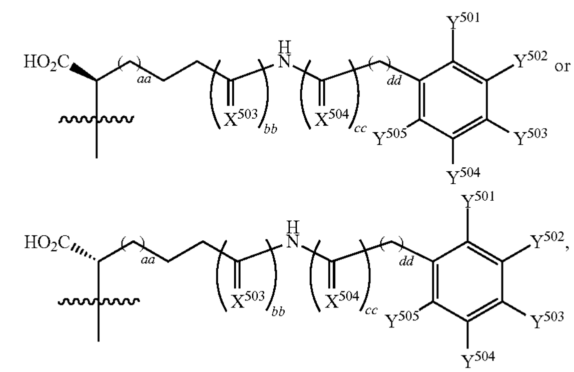

or , where $Y^{501}$, $Y^{502}$, $Y^{503}$, $Y^{504}$, and $Y^{505}$ are independently H, halo, or alkyl, $X^{503}$, $X^{504}$, $X^{505}$, and $X^{506}$ are each independently O or S, aa is independently at each occurrence 0, 1, or 2, bb is independently at each occurrence 0 or 1, cc is independently at each occurrence 0 or 1, and dd is independently at each occurrence 0, 1, 2, 3, or 4. In any embodiment herein, it may be that bb and cc cannot be the same value. In any embodiment herein, it may be that $Y^{503}$ is I and each of $Y^{501}$, $Y^{502}$, $Y^{503}$, $Y^{504}$, and $Y^{505}$ are each independently H.

Representative chelators useful in any embodiment of the present technology include, but are not limited to, a covalently conjugated substituted or unsubstituted chelator of the following group:

1,4,7-triazacyclononane-1,4,7-triacetic acid (NOTA),
1,4,7,10-tetraazacyclododecane-1,4,7,10-tetraacetic acid (DOTA),
p-SCN-Bn-DOTA (also known as 2B-DOTA-NCS),
PIP-DOTA,
diethylenetriaminepentaacetic acid (DTPA),
PIP-DTPA,
AZEP-DTPA,
ethylenediamine tetraacetic acid (EDTA),
triethylenetetraamine-N,N,N',N",N'",N""-hexa-acetic acid (TTHA),
7-[2-(bis-carboxymethylamino)-ethyl]-4,10-bis-carboxymethyl-1,4,7,10-tetraaza-cyclododec-1-yl-acetic acid (DEPA),
2,2',2"-(10-(2-(bis(carboxymethyl)amino)-5-(4-isothiocyanatophenyl) pentyl)-1,4,7,10-tetraazacyclododecane-1,4,7-triyl)triacetic acid (3p-C-DEPA-NCS),
NETA,
{4-carboxymethyl-7-[2-(carboxymethylamino)-ethyl]-perhydro-1,4,7-triazonin-1-yl}-acetic acid (NPTA),
diacetylpyridinebis(benzoylhydrazone),
1,4,7,10,13,16-hexaazacyclooctadecane-N,N',N",N'",N"",N'""-hexaaceticacid (HEHA),
octadentate terephthalamide ligands,
siderophores,
2,2'-(4-(2-(bis(carboxymethyl)amino)-5-(4-isothiocyanatophenyl)pentyl)-10-(2-(bis(carboxymethyl)amino) ethyl)-1,4,7,10-tetraazacyclododecane-1,7-diyl)diacetic acid,
N,N'-bis[(6-carboxy-2-pyridil)methyl]-4,13-diaza-18-crown-6 ($H_2$macropa),
6-((16-((6-carboxypyridin-2-yl)methyl)-1,4,10,13-tetraoxa-7,16-diazacyclooctadecan-7-yl)methyl)-4-isothiocyanatopicolinic acid (macropa-NCS),
1,4,7,10-tetraaza-1,4,7,10-tetra(2-carbamonyl methyl)cyclododecane (TCMC),
S-2-(4-Isothiocyanatobenzyl)-1,4,7,10-tetraaza-1,4,7,10-tetra(2-carbamoylmethyl)cyclododecane (S-p-SCN-Bn-TCMC),
R-2-(4-Isothiocyanatobenzyl)-1,4,7,10-tetraaza-1,4,7,10-tetra(2-carbamoylmethyl)cyclododecane (R-p-SCN-Bn-TCMC), and
3,9-carboxymethyl-6-(2-methoxy-5-isothiocyanatophenyl)carboxymethyl-3,6,9,15-tetraazabicyclo-[9.3.1] pentadeca-1(15),11,13-triene.

Certain members of this exemplary group are illustrated below.

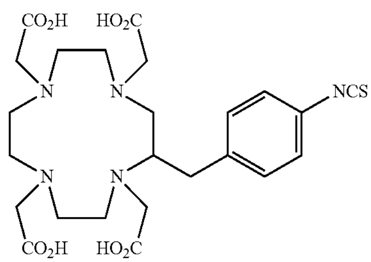

-continued

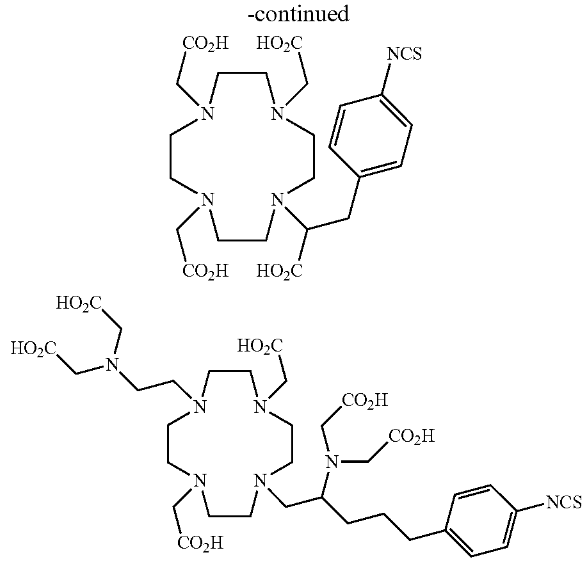

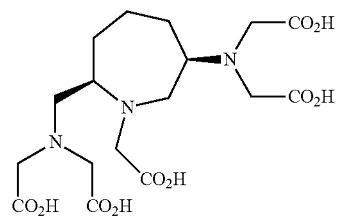

AZEP-DTPA

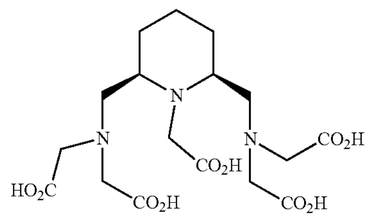

PIP-DTPA

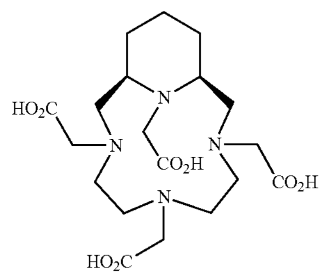

PIP-DOTA

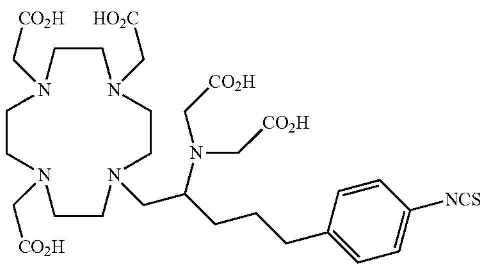

3p-C-DEPA-NCS

-continued

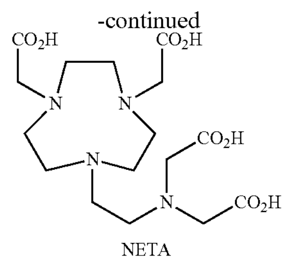

NETA

It is to be understood that a "covalently conjugated" chelator means a chelator (such as those listed above) wherein one or more bonds to a hydrogen atom contained therein are replaced by a bond to an atom of the remainder of the Rad and/or CHEL moiety, to $L^{501}$, and/or to $L^{502}$, or a pi bond between two atoms is replaced by a bond from one of the two atoms to an atom of the remainder of the Rad and/or CHEL moiety, to $L^{501}$, and/or to $L^{502}$, and the other of the two atoms includes a new bond, e.g. to a hydrogen (such as reaction of an —NCS group in the chelator to provide the covalently conjugated chelator).

In any embodiment disclosed herein, it may be that the CHEL of the tripartite compounds is a chelator as provided in the compounds of Formula I, IA, or II. For example, tripartite compound may be a targeting compound of Formula II where $R^{22}$, $R^{24}$, $R^{26}$, and $R^{28}$ are each independently

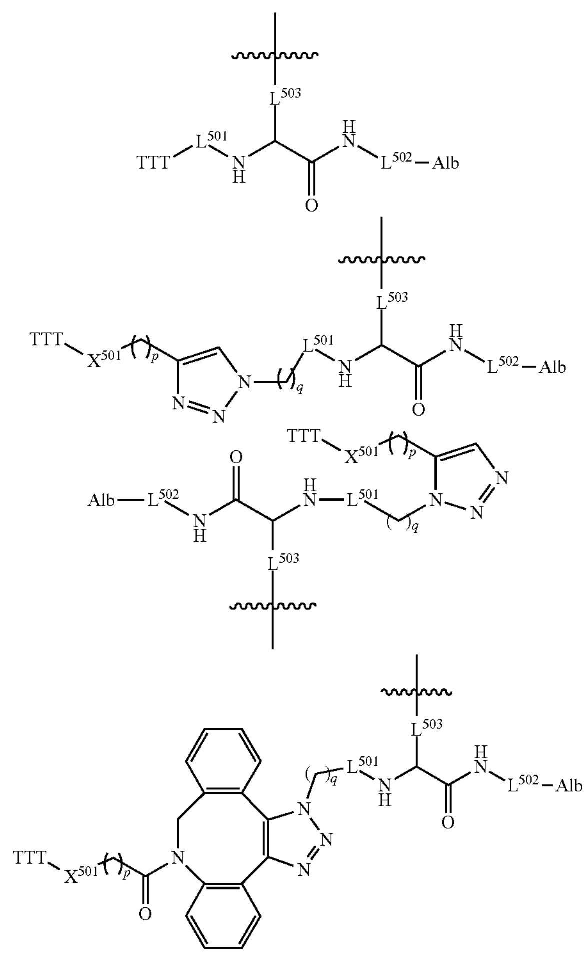

-continued

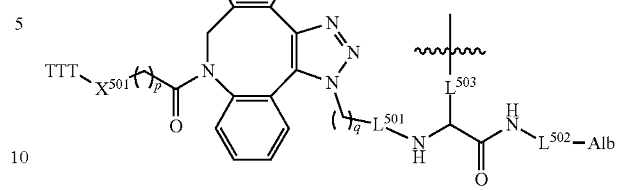

In an embodiment disclosed herein TTT may be

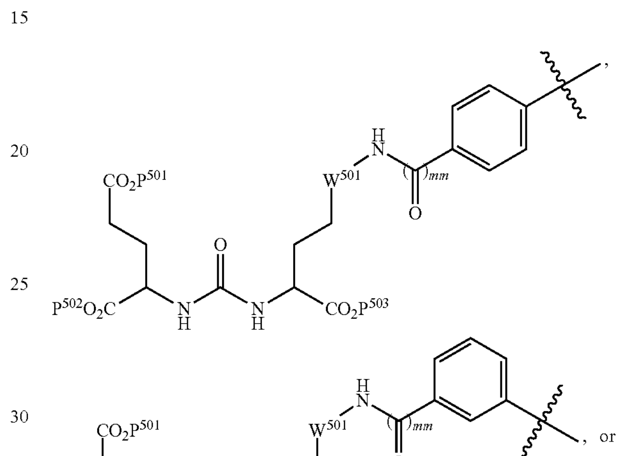

or

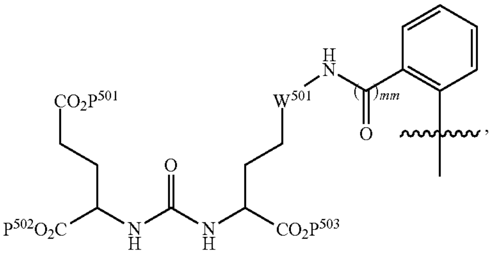

$W^{501}$ is —C(O)—, $—(CH_2)_{ww}—$, or $—(CH_2)_{oo}—NH—C(O)—$;

mm is 0 or 1;

ww is 1 or 2;

oo is 1 or 2; and $P^{501}$, $P^{502}$, and $P^{503}$ are each independently H, methyl, benzyl, 4-methoxybenzyl, or tert-butyl.

In any embodiment herein, it may be that each of $P^{501}$, $P^{502}$, and $P^{503}$ are H.

The tripartite compounds of the present technology include variations on any of the three domains: e.g., the domain including the chelator, the domain including the albumin-binding group, or the domain including the tumor targeting moiety. The following are exemplary.

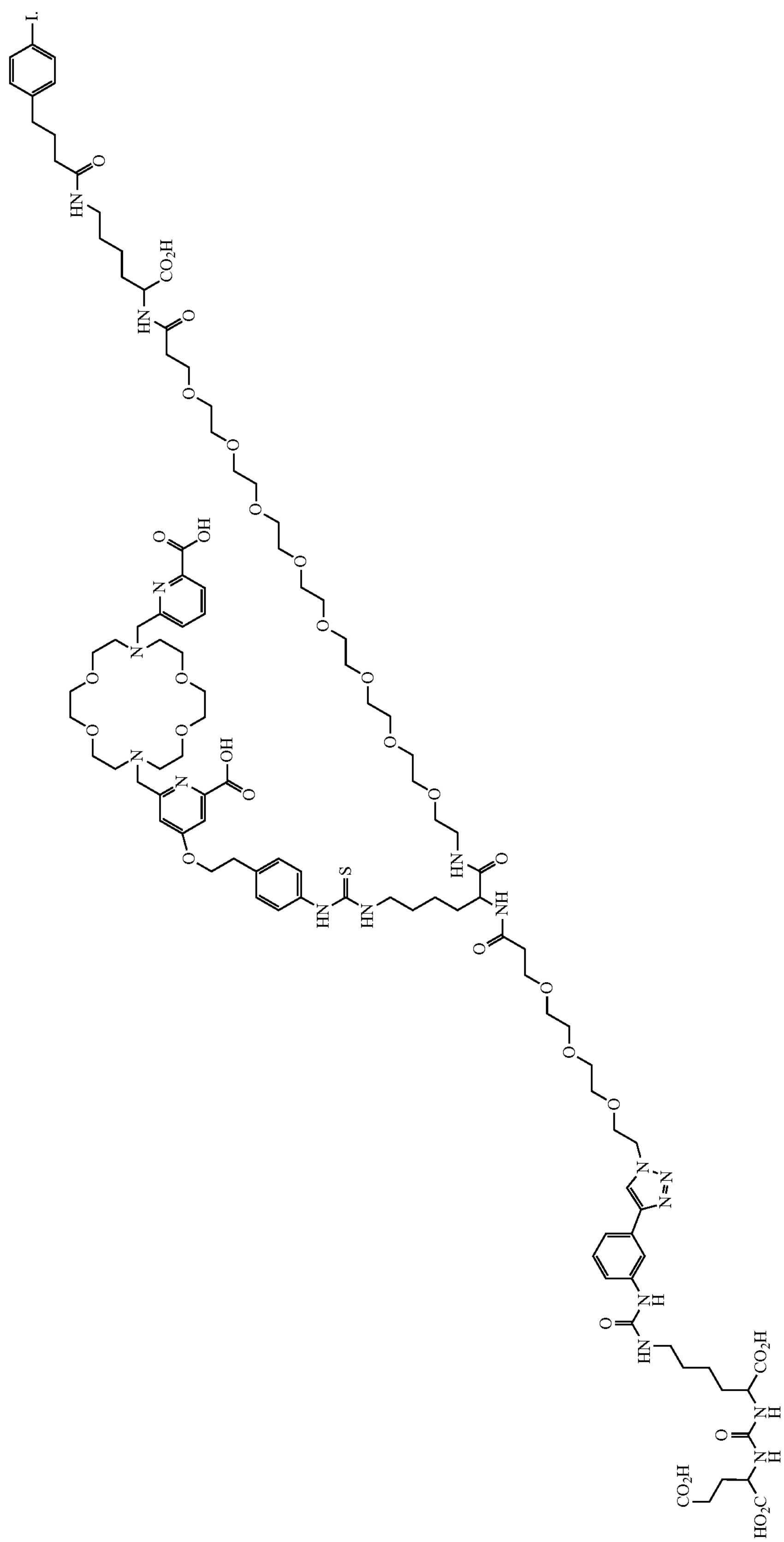
RPS-092

In any embodiment disclosed herein, RPS-92 may optionally chelate $^{213}Bi^{3+}$, $^{211}At^{+}$, $^{225}Ac^{3+}$, $^{152}Dy^{3+}$, $^{212}Bi^{3+}$, $^{211}Bi^{3+}$, $^{217}At^{+}$, $^{227}Th^{4+}$, $^{226}Th^{4+}$, $^{233}Ra^{2+}$, $^{212}Pb^{2+}$, or $^{212}Pb^{4+}$.

NTI-093 is an analog of NTI-063, where TCMC is used as the chelator.

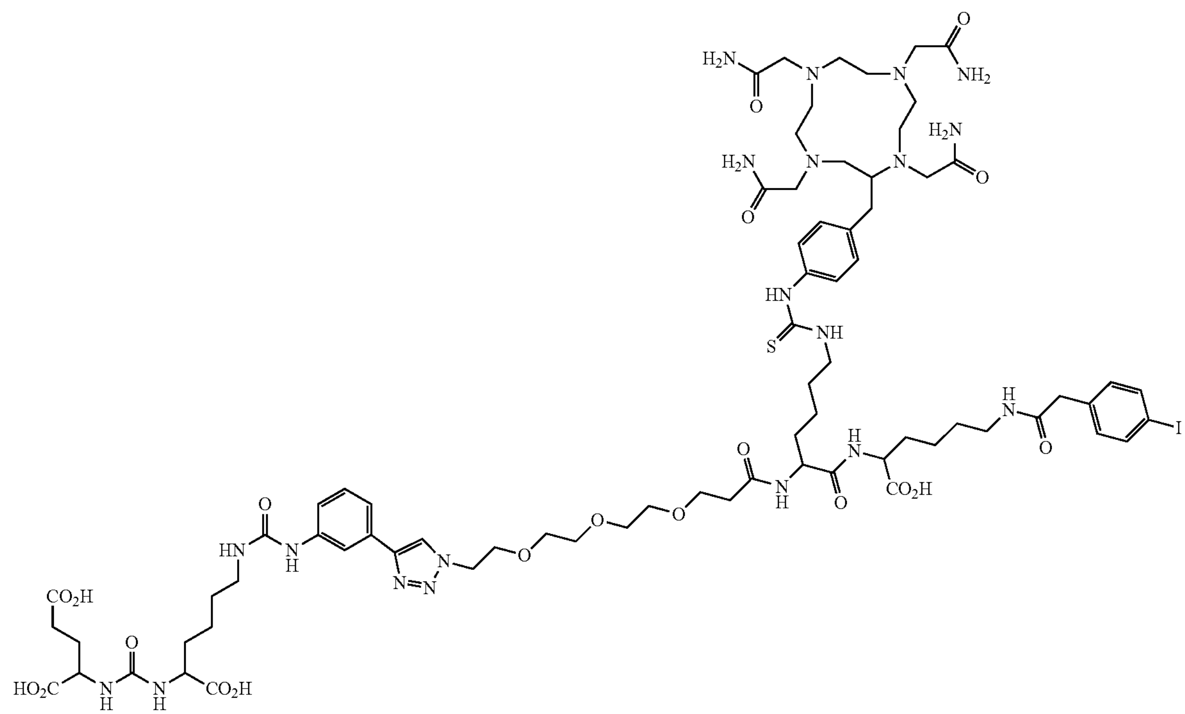 [SMILES: NC(=O)CN1CCN(CC(N)=O)CCN(CC(N)=O)C(Cc2ccc(NC(=S)NCCCCC(NC(=O)CCOCCOCCOCCn3cc(-c4cccc(NC(=O)NCCCCC(NC(=O)NC(CCC(=O)O)C(=O)O)C(=O)O)c4)nn3)C(=O)NC(CCCCNC(=O)Cc3ccc(I)cc3)C(=O)O)cc2)CN(CC(N)=O)CC1]

In any embodiment disclosed herein, NTI-93 may optionally chelate $^{112}Pb^{2+}$ or $^{21}Pb^{4+}$.

NTI-094 is an analog of NTI-072, where TCMC is used as the chelator.

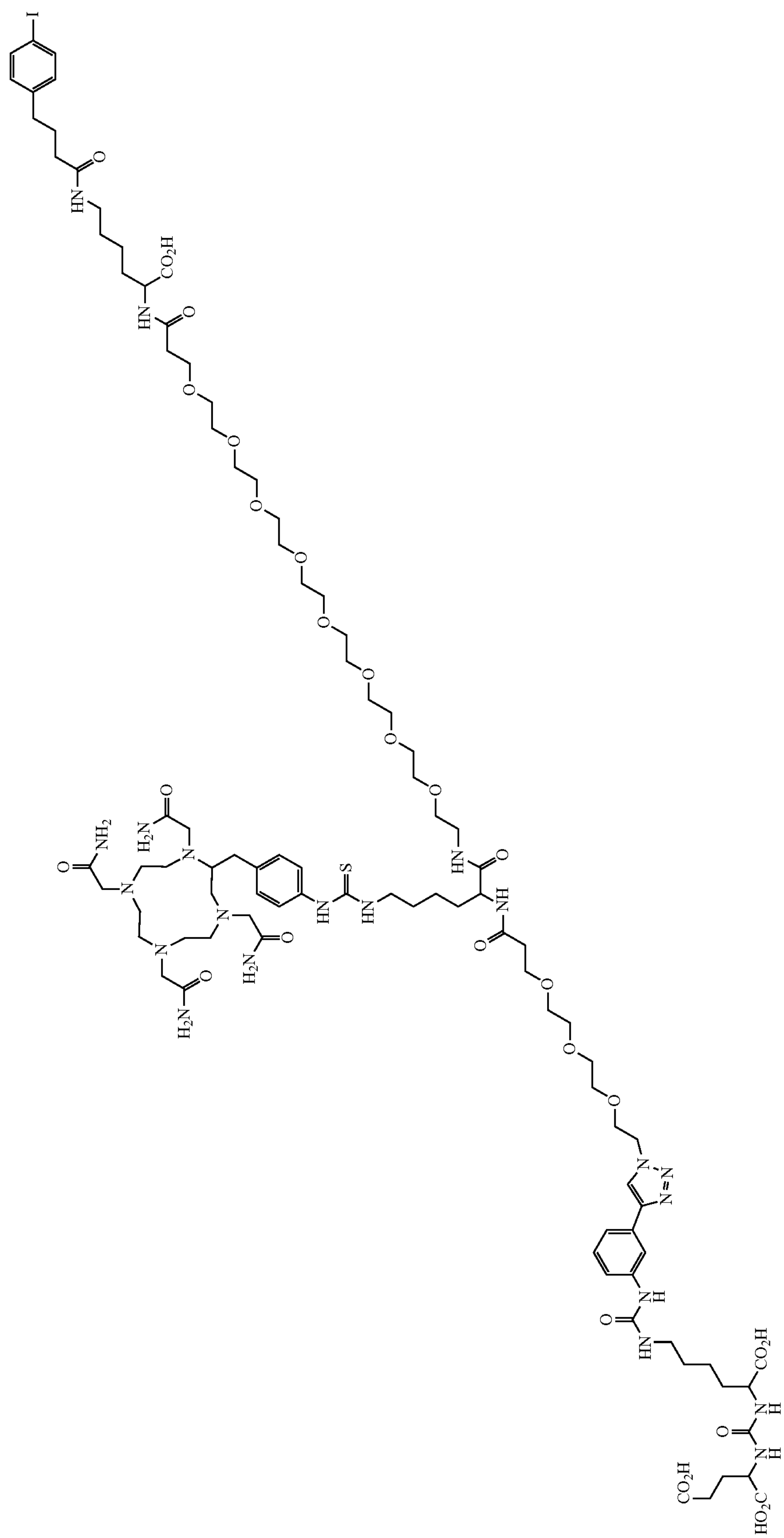

In any embodiment disclosed herein, NTI-94 may optionally chelate $^{212}Pb^{2+}$ or $^{212}Pb^{4+}$.
The following is a Bromo analog of NTI-063, with modification to the albumin binding domain.
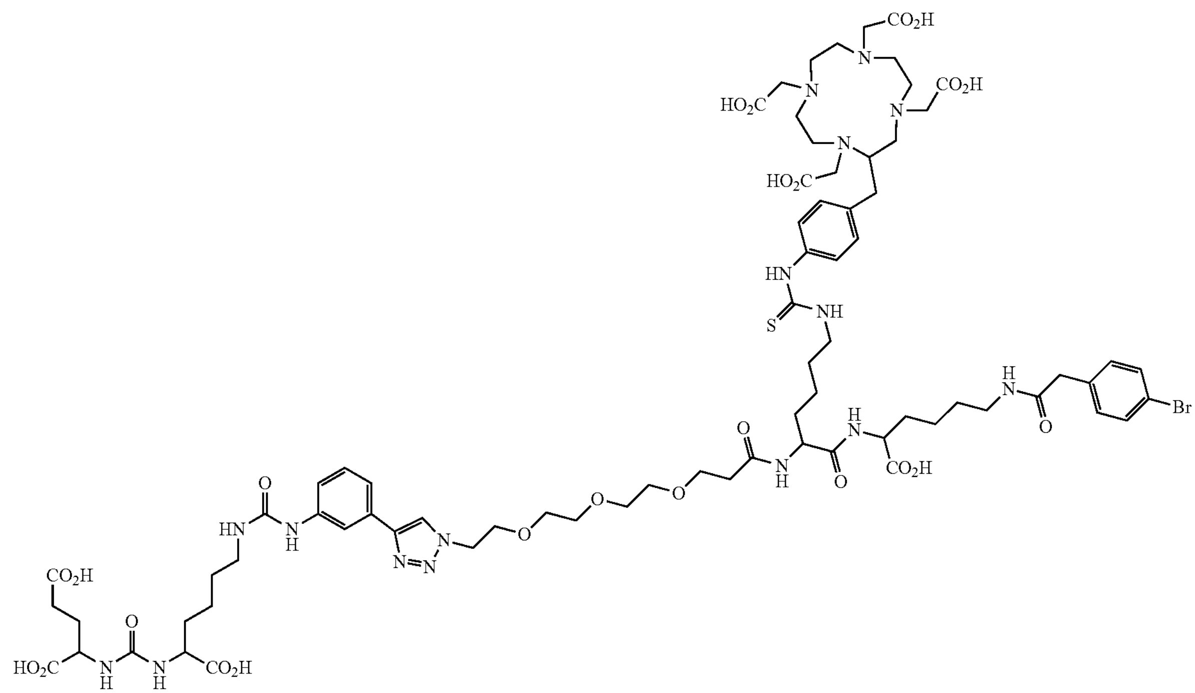 [SMILES: O=C(O)CCC(NC(=O)NC(CCCCNC(=O)Nc1cccc(-c2cn(CCOCCOCCOCCC(=O)NC(CCCCNC(=S)Nc3ccc(CC4CN(CC(=O)O)CCN(CC(=O)O)CCN(CC(=O)O)CCN4CC(=O)O)cc3)C(=O)NC(CCCCNC(=O)Cc3ccc(Br)cc3)C(=O)O)nn2)c1)C(=O)O)C(=O)O]
The following is a Chloro analog of NTI-063, with modification to the albumin binding domain.
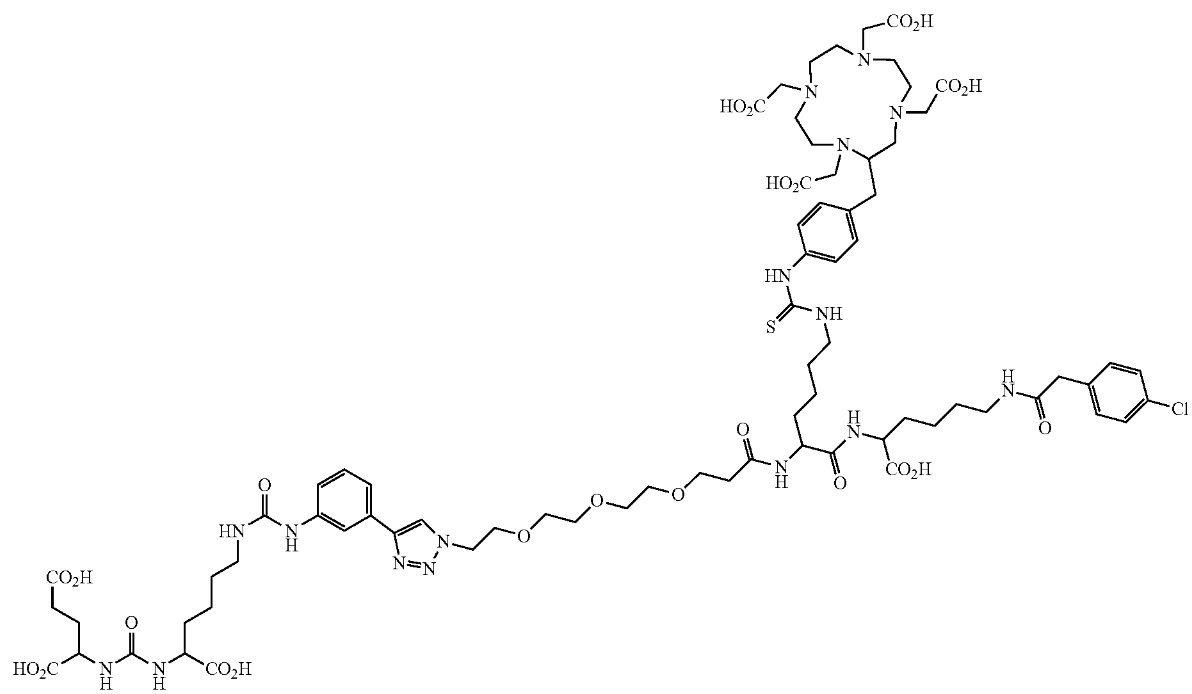 [SMILES: O=C(O)CCC(NC(=O)NC(CCCCNC(=O)Nc1cccc(-c2cn(CCOCCOCCOCCC(=O)NC(CCCCNC(=S)Nc3ccc(CC4CN(CC(=O)O)CCN(CC(=O)O)CCN(CC(=O)O)CCN4CC(=O)O)cc3)C(=O)NC(CCCCNC(=O)Cc3ccc(Cl)cc3)C(=O)O)nn2)c1)C(=O)O)C(=O)O]

NTI-309 modifies the tumor targeting domain, to target seprase (Fibroblast Activation Protein/FAP).
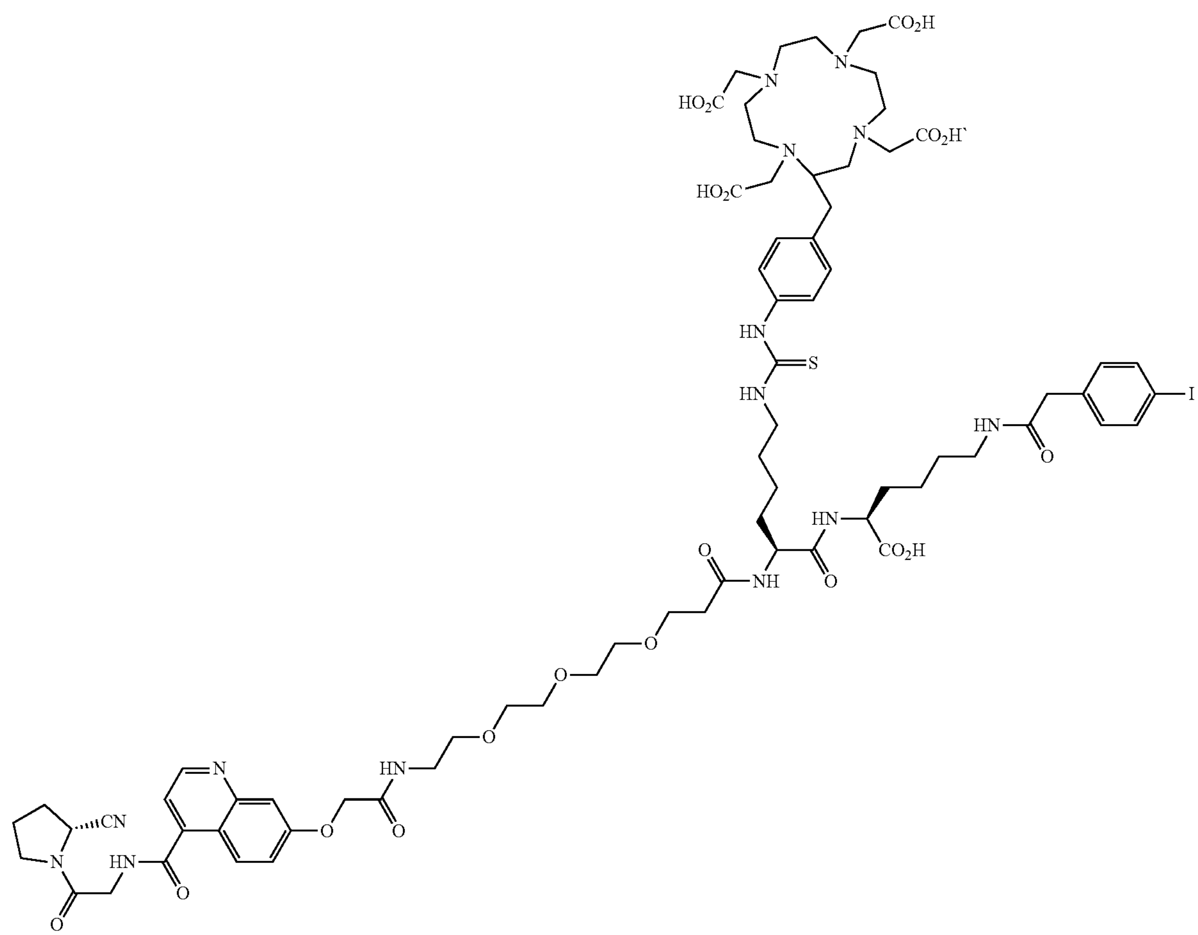
The NTI-309 compound can be include TCMC as the chelator.

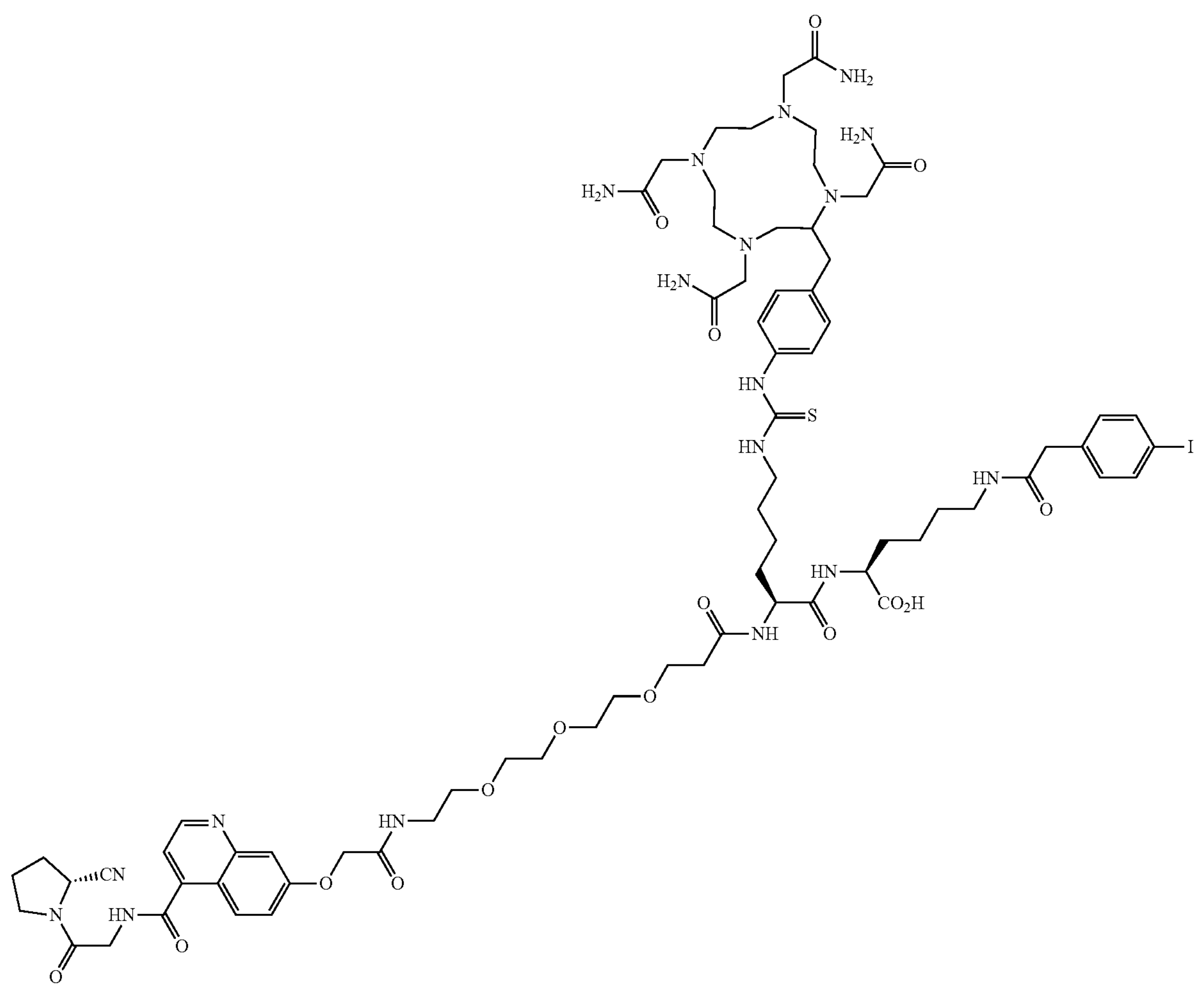 [SMILES: N#C[C@H]1CCCN1C(=O)CNC(=O)c1ccnc2cc(OCC(=O)NCCOCCOCCOCCC(=O)N[C@@H](CCCCNC(=S)Nc3ccc(CC4CN(CC(N)=O)CCN(CC(N)=O)CCN(CC(N)=O)CCN4CC(N)=O)cc3)C(=O)N[C@@H](CCCCNC(=O)Cc3ccc(I)cc3)C(=O)O)ccc12]
In any embodiment disclosed herein, NTI-309 may optionally chelate $^{212}Pb^{2+}$ or $^{212}Pb^{4+}$.

The following is a Boronic acid analog of NTI-309.
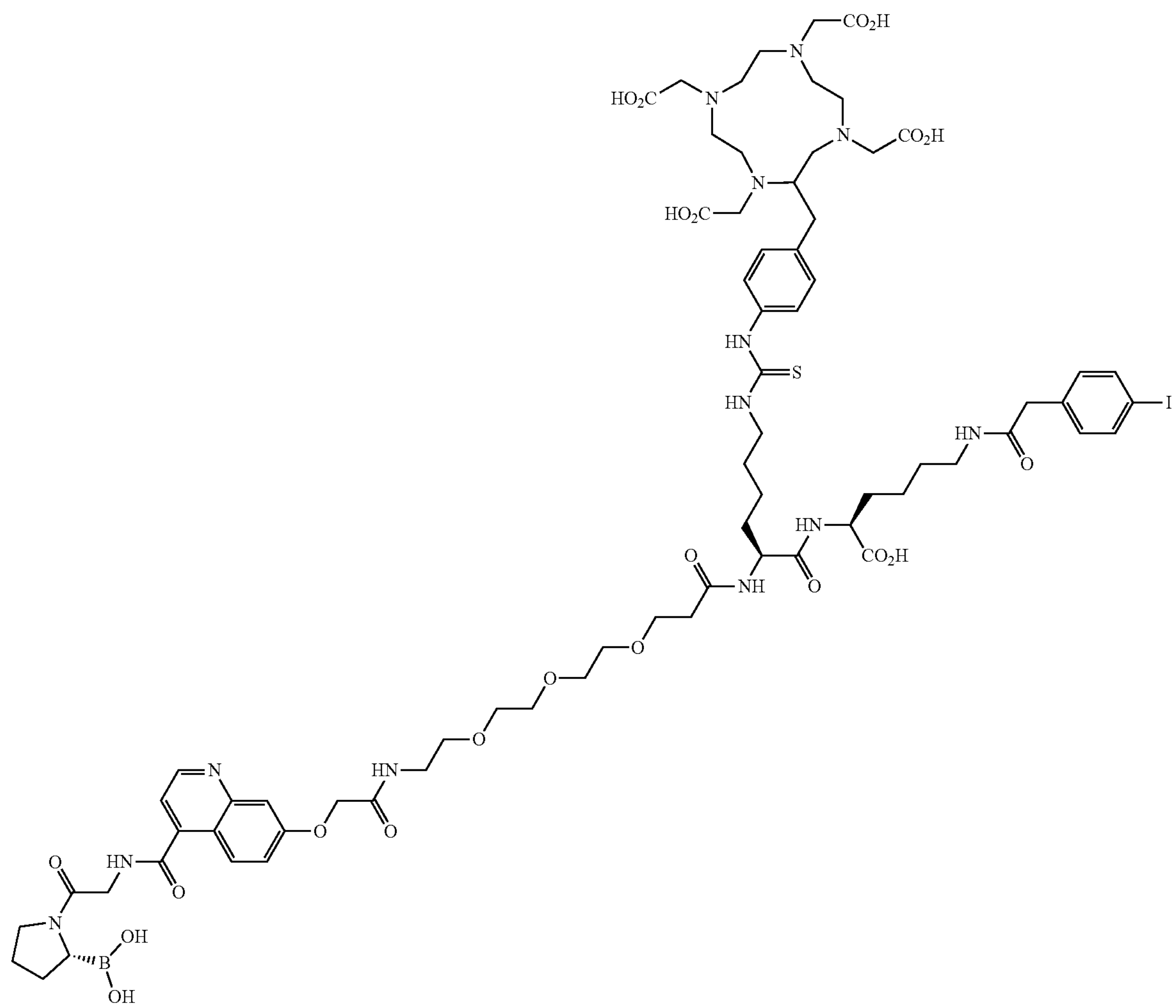 [SMILES: O=C(O)CN1CCN(CC(=O)O)CCN(CC(=O)O)C(Cc2ccc(NC(=S)NCCCC[C@H](NC(=O)CCOCCOCCOCCNC(=O)COc3ccc4c(C(=O)NCC(=O)N5CCC[C@H]5B(O)O)ccnc4c3)C(=O)N[C@@H](CCCCNC(=O)Cc3ccc(I)cc3)C(=O)O)cc2)CN(CC(=O)O)CC1]
The following is a Boronic acid analog of NTI-309, using TCMC as a chelator.

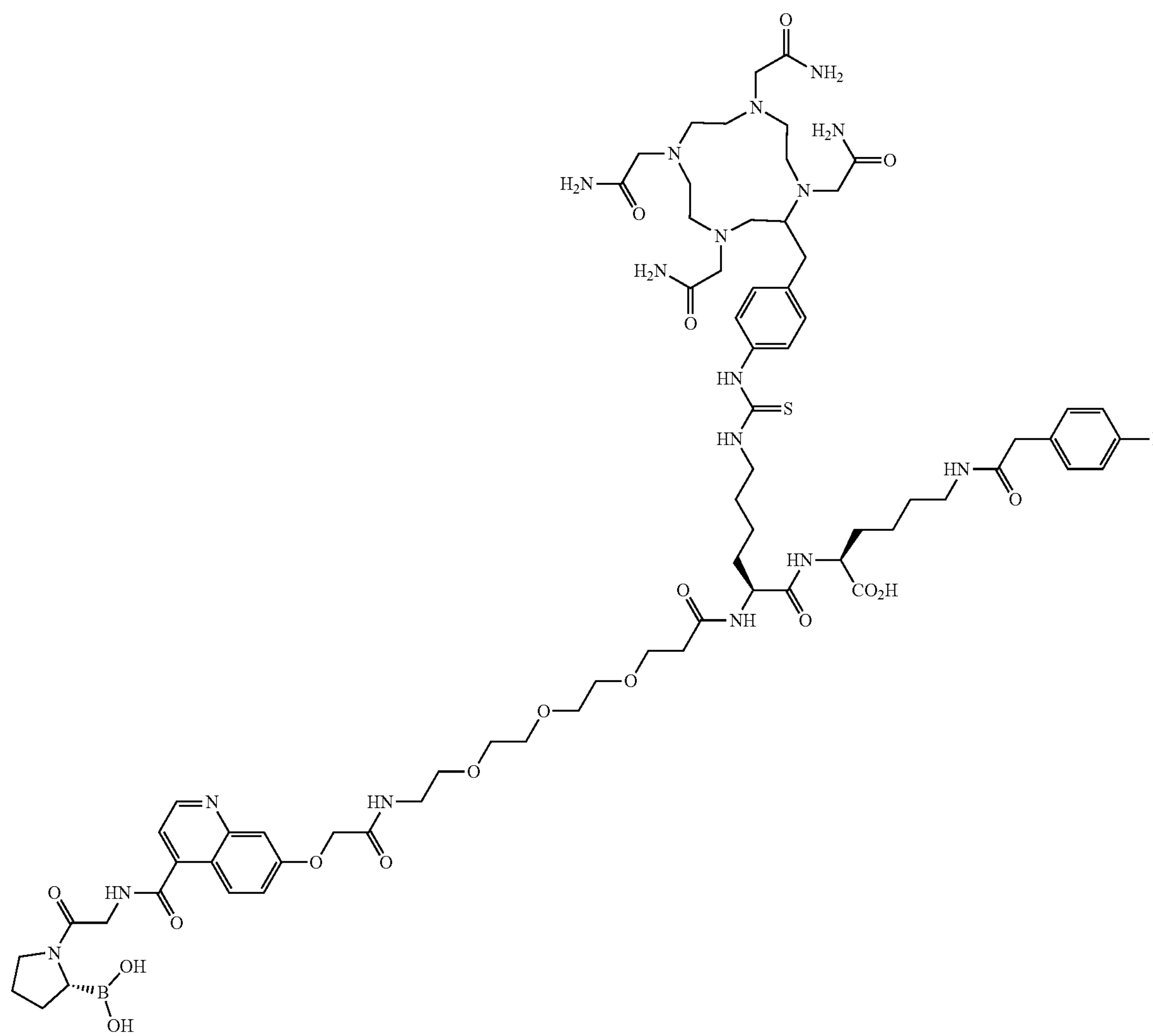 [SMILES: NC(=O)CN1CCN(CC(N)=O)CCN(CC(N)=O)C(Cc2ccc(NC(=S)NCCCC[C@H](NC(=O)CCOCCOCCOCCNC(=O)COc3ccc4c(C(=O)NCC(=O)N5CCC[C@H]5B(O)O)ccnc4c3)C(=O)N[C@@H](CCCCNC(=O)Cc3ccc(I)cc3)C(=O)O)cc2)CN(CC(N)=O)CC1]

In any embodiment disclosed herein, this analog may optionally chelate $^{212}Pb^{2+}$ or $^{212}Pb^{4+}$.

Further by way of specific examples, a derivative of RPS-072 (which itself targets PSMA), can be constructed, where TTT has affinity for the SSTR2 receptor, using a derivative of lanreotide where this compound (A) has a molecular weight of 3537.93 and a formula of $C_{165}H_{235}IN_{28}O_{44}S_3$. Similarly, a derivative of RPS-072 can be prepared, that targets GRP/bombesin receptor, where this compound (B) has a molecular weight of 3537.93 and a formula of $C_{167}H_{248}IN_{31}O_{44}S$.

(A)
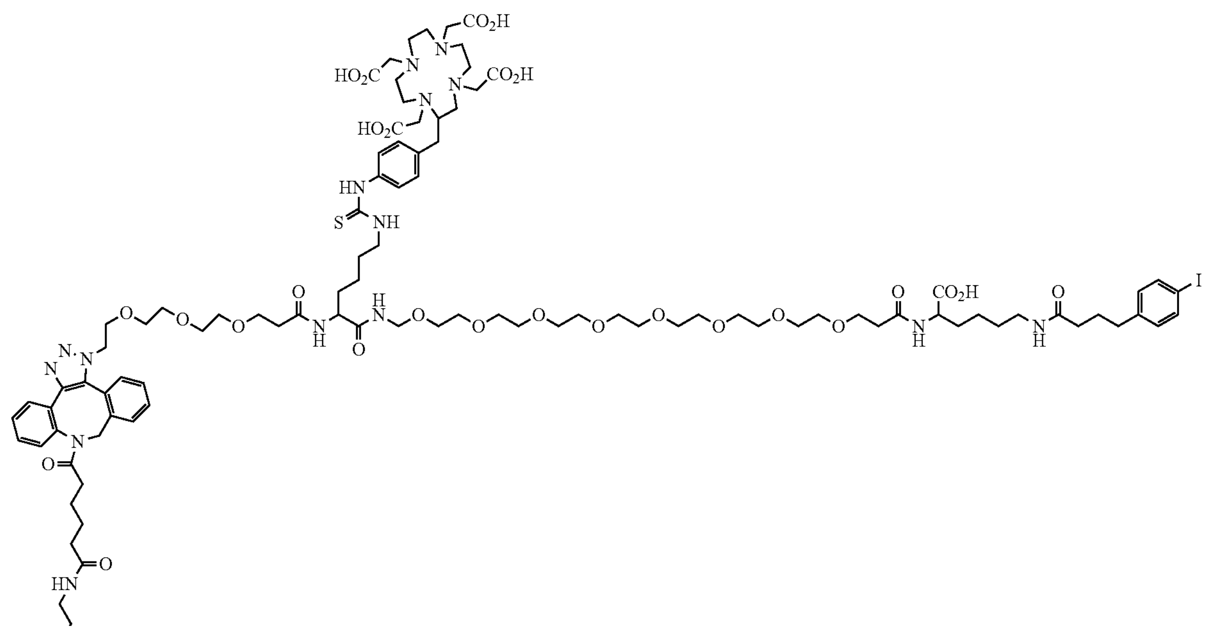
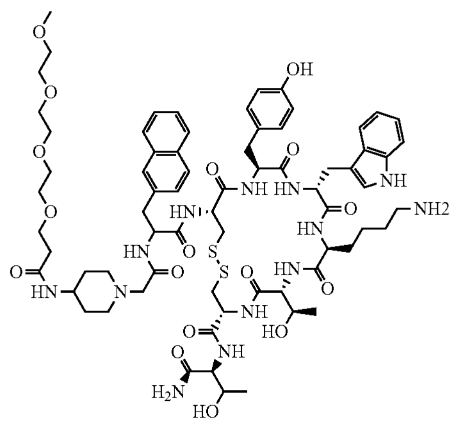

-continued (B)

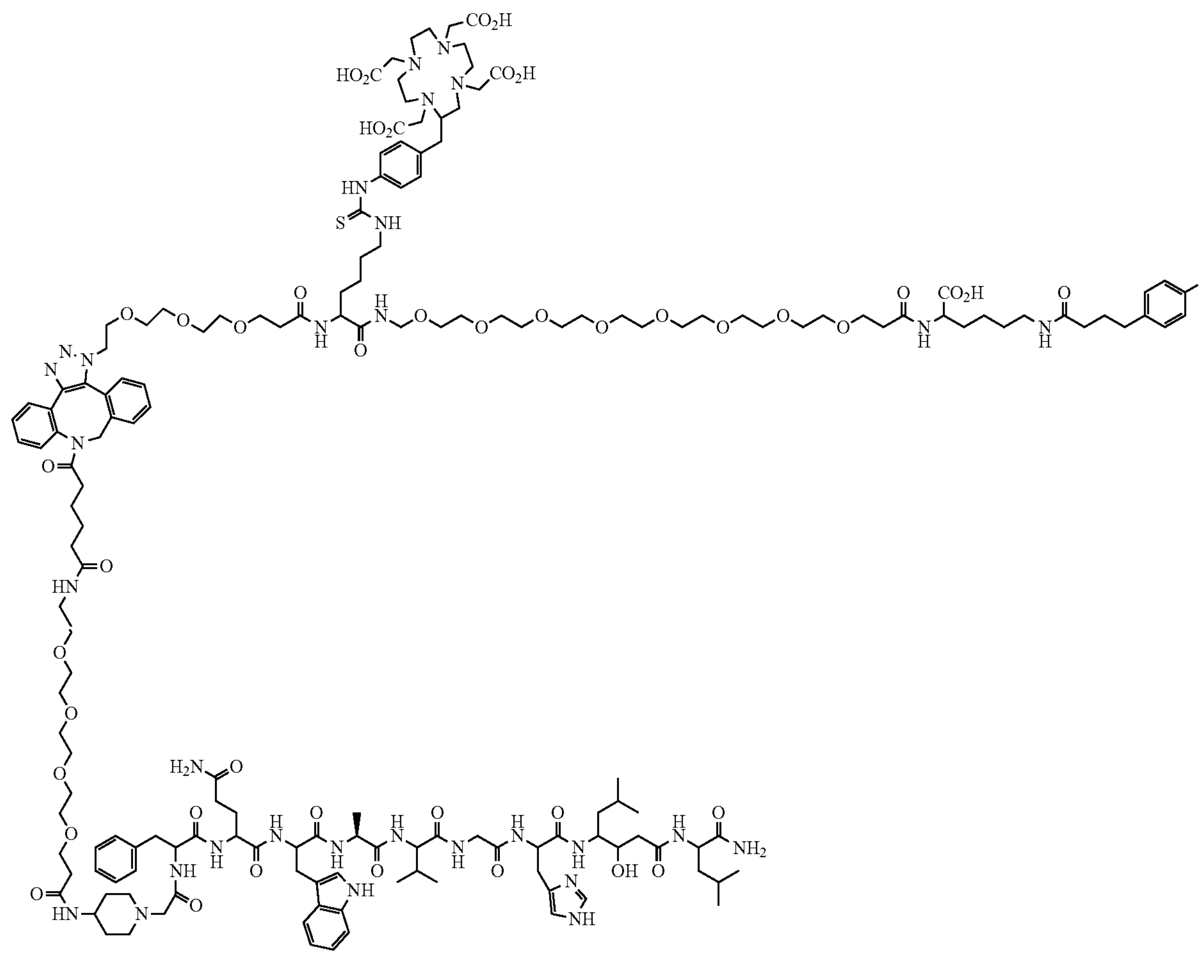

The present technology also provides compositions (e.g., pharmaceutical compositions) and medicaments comprising any of one of the embodiments of the compounds of Formulas I, IA, II, any one of the modified antibodies, modified antibody fragments, or modified binding peptides of the present technology disclosed herein, or any one of the embodiments of the tripartite compounds disclosed herein and a pharmaceutically acceptable carrier or one or more excipients or fillers (collectively referred to as "pharmaceutically acceptable carrier" unless otherwise specified). The compositions may be used in the methods and treatments described herein. The pharmaceutical composition may include an effective amount of any embodiment of the compounds of the present technology for treating the cancer and/or mammalian tissue overexpressing PSMA or an effective amount of any embodiment of the modified antibody, modified antibody fragment, or modified binding peptide of the present technology for treating the cancer and/or mammalian tissue overexpressing PSMA or an effective amount of any embodiment of the tripartite compound of the present technology for treating the cancer and/or mammalian tissue overexpressing PSMA. In an related aspect, a method of treating a subject is provided, wherein the method includes administering a targeting compound of the present technology to the subject or administering a modified antibody, modified antibody fragment, or modified binding peptide of the present technology to the subject. In any embodiment disclosed herein, it may be that the subject suffers from cancer and/or mammalian tissue overexpressing prostate specific membrane antigen ("PSMA"). In any embodiment herein, it may be the administering includes administering an effective amount of any embodiment of the compounds of the present technology for treating the cancer and/or mammalian tissue overexpressing PSMA of the compound or an effective amount of any embodiment of the modified antibody, modified antibody fragment, or modified binding peptide of the present technology for treating the cancer and/or mammalian tissue overexpressing PSMA or an effective amount of any embodiment of the tripartite compound of the present technology for treating the cancer and/or mammalian tissue overexpressing PSMA. The subject may suffer from a mammalian tissue expressing a somatostatin receptor, a bombesin receptor, seprase, or a combination of any two or more thereof and/or mammalian tissue overexpressing PSMA. The mammalian tissue of any embodiment disclosed herein may include one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer. In any embodiment disclosed herein, the subject may suffer from one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer. In any embodiment disclosed herein, the composition (e.g., pharmaceutical composition) and/or medicament may be formulated for parenteral administration. In any embodiment disclosed herein, the composition (e.g., pharmaceutical composition) and/or medicament may be formulated for intraveneous administration. In any embodiment disclosed herein, the administering step of the method may include parenteral administration. In any embodiment disclosed herein, the administering step of the method may include intraveneous administration.

In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of e.g., one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer. Another example of an effective amount includes amounts or dosages that are capable of reducing symptoms associated with e.g., one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer, such as, for example, reduction in proliferation and/or metastasis of prostate cancer, breast cancer, or bladder cancer. The effective amount may be from about 0.01 μg to about 1 mg of the compound per gram of the composition, and preferably from about 0.1 μg to about 500 μg of the compound per gram of the composition. As used herein, a "subject" or "patient" is a mammal, such as a cat, dog, rodent or primate. Typically the subject is a human, and, preferably, a human suffering from or suspected of suffering from one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer (such as colon adenocarcinoma), a primary gastric adenocarcinoma, a primary colorectal adenocarcinoma, a renal cell carcinoma, and a prostate cancer. The term "subject" and "patient" can be used interchangeably.

In any of the embodiments of the present technology described herein, the pharmaceutical composition may be packaged in unit dosage form. The unit dosage form is effective in treating one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer (such as colon adenocarcinoma), a primary gastric adenocarcinoma, a primary colorectal adenocarcinoma, a renal cell carcinoma, and a prostate cancer. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\text{-}10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges, suppositories, patches, nasal sprays, injectables, implantable sustained-release formulations, mucoadherent films, topical varnishes, lipid complexes, etc.

The pharmaceutical compositions may be prepared by mixing one or more of the compounds of Formulas I, IA, II, or any one of the modified antibodies, modified antibody fragments, or modified binding peptides of the present technology, or any embodiment of the tripartite compound of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with cancer and/or a mammalian tissue overexpressing PSMA. The compounds and compositions described herein may be used to prepare formulations and medicaments that treat e.g., prostate cancer, breast cancer, or bladder cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. The instant compositions may also include, for example, micelles or liposomes, or some other encapsulated form.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For the indicated condition, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In another aspect, the present technology provides a method of treating cancer by administering an effective amount of the targeting composition according to Formula II to a subject having cancer. Since a cancer cell targeting agent can be selected to target any of a wide variety of cancers, the cancer considered herein for treatment is not limited. The cancer can be essentially any type of cancer. For example, antibodies or peptide vectors can be produced to target any of a wide variety of cancers. The targeting compositions described herein are typically administered by injection into the bloodstream, but other modes of administration, such as oral or topical administration, are also considered. In some embodiments, the targeting composition may be administered locally, at the site where the target cells are present, i.e., in a specific tissue, organ, or fluid (e.g., blood, cerebrospinal fluid, etc.). Any cancer that can be targeted through the bloodstream is of particular consideration herein. Some examples of applicable body parts containing cancer cells include the breasts, lungs, stomach, intestines, prostate, ovaries, cervix, pancreas, kidney, liver, skin, lymphs, bones, bladder, uterus, colon, rectum, and brain. The cancer can also include the presence of one or more carcinomas, sarcomas, lymphomas, blastomas, or teratomas (germ cell tumors). The cancer may also be a form of leukemia. In some embodiments, the cancer is a triple negative breast cancer.

As is well known in the art, the dosage of the active ingredient(s) generally depends on the disorder or condition being treated, the extent of the disorder or condition, the method of administration, size of the patient, and potential side effects. In different embodiments, depending on these and other factors, a suitable dosage of the targeting composition may be precisely, at least, above, up to, or less than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

The examples herein are provided to illustrate advantages of the present technology and to further assist a person of ordinary skill in the art with preparing or using the compounds of the present technology or salts, pharmaceutical compositions, derivatives, prodrugs, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

Exemplary Synthetic Procedures and Characterization

Materials and Instrumentation. All solvents and reagents, unless otherwise noted, were purchased from commercial sources and used as received without further purification. Solvents noted as "dry" were obtained following storage over 3 Å molecular sieves. Metal salts were purchased from Strem Chemicals (Newburyport, Mass.) and were of the highest purity available; $Lu(ClO_4)_3$ was provided as an aqueous solution containing 15.1 wt % Lu. The bifunctional ligand p-SCN-Bn-DOTA was purchased from Macrocyclics (Piano, Tex.). $NMe_4OH$ was purchased as a 25 wt % solution in $H_2O$ (trace metals basis, Beantown Chemical, Hudson, N.H.). Hydrochloric acid (BDH Aristar Plus, VWR, Radnor, Pa.) and nitric acid (Optima, ThermoFisher Scientific, Waltham, Mass.) were of trace metals grade. Both Chelex 100 (sodium form, 50-100 mesh) and human serum used for $^{225}$Ac-complex challenge assays were purchased from Sigma Aldrich (St. Louis, Mo.). Deionized water (≥18 MΩ cm) was prepared on site using either Millipore Direct-Q® 3UV or Elga Purelab Flex 2 water purification systems.

Reactions were monitored by thin-layer chromatography (TLC, Whatman UV254 aluminum-backed silica gel). The HPLC system used for analysis and purification of compounds consisted of a CBM-20A communications bus module, an LC-20AP (preparative) or LC-20AT (analytical) pump, and an SPD-20AV UV/Vis detector monitoring at 270 nm (Shimadzu, Japan). Analytical chromatography was carried out using an Ultra Aqueous C18 column, 100 Å, 5 μm, 250 mm×4.6 mm (Restek, Bellefonte, Pa.) at a flow rate of 1.0 mL/min, unless otherwise noted. Purification was performed with an Epic Polar preparative column, 120 Å, 10 μm, 25 cm×20 mm (ES Industries, West Berlin, N.J.) at a flow rate of 14 mL/min, unless otherwise noted. Gradient HPLC methods were employed using a binary mobile phase that contained $H_2O$ (A) and either MeOH (B) or ACN (C). HPLC Method A: 10% B (0-5 min), 10-100% B (5-25 min). Method B: 10% C (0-5 min), 10-100% C (5-25 min). Method C: 10% C (0-5 min), 10-100% C (5-40 min). Method D: 10% C (0-5 min), 10-100% C (5-20 min). The solvent systems contained 0.1% trifluoroacetic acid (TFA), except for Method C, in which 0.2% TFA was used. NMR spectra were recorded at ambient temperature on Varian Inova 300 MHz, 400 MHz, 500 MHz or 600 MHz spectrometers, or on a Bruker AV III HD 500 MHz spectrometer equipped with a broadband Prodigy cryoprobe. Chemical shifts are reported in ppm. $^1$H and $^{13}$C NMR spectra were referenced to the TMS internal standard (0 ppm), to the residual solvent peak, or to an acetonitrile internal standard (2.06 ppm in $D_2O$ spectra). $^{19}$F NMR spectra were referenced to a monofluorobenzene internal standard (−113.15 ppm). The splitting of proton resonances in the reported $^1$H spectra is defined as: s=singlet, d=doublet, t=triplet, q=quartet, m=multiplet, dt=doublet of triplets, td=triplet of doublets, and br=broad. IR spectroscopy was performed on a KBr pellet of sample using a Nicolet Avatar 370 DTGS (ThermoFisher Scientific, Waltham, Mass.). High-resolution mass spectra (HRMS) were recorded on an Exactive Orbitrap mass spectrometer in positive ESI mode (ThermoFisher Scientific, Waltham, Mass.). UV/visible spectra were recorded on a Cary 8454 UV-Vis (Agilent Technologies, Santa Clara, Calif.) using 1-cm quartz cuvettes, unless otherwise noted. Elemental analysis (EA) was performed by Atlantic Microlab, Inc. (Norcross, Ga.).

Synthesis and Characterization of Macropa Complexes, Macropa-NCS, and Macropa-NHC(S)$NHCH_3$. N,N'-bis[(6-carboxy-2-pyridil)methyl]-4,13-diaza-18-crown-6 ($H_2$macropa·2HCl·4$H_2O$)[102,103] was prepared using 1,7,10,16-tetraoxa-4,13-diazacyclooctadecane (7) that was either purchased from EMD Millipore (Darmstadt, Germany) or synthesized via literature protocols.[104] Chelidamic acid monohydrate (1) was purchased from TCI America (Portland, Oreg.). Dimethyl 4-chloropyridine-2,6-dicarboxylate (2),[105] dimethyl 4-azidopyridine-2,6-dicarboxylate (3),[106] and 6-chloromethylpyridine-2-carboxylic acid methyl ester (8),[102] were prepared via the indicated literature protocols.

Preparation of $[La(macropa)]^{2+}$

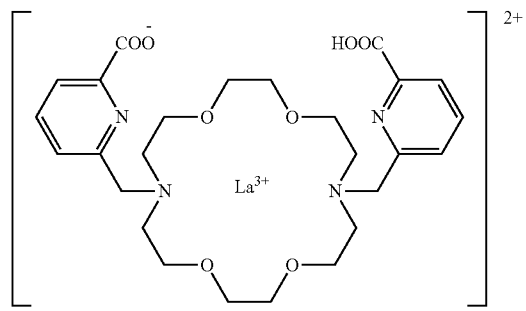

To a suspension of $H_2$macropa·2HCl·4$H_2O$ (0.0233 g, 0.034 mmol) in 2-propanol (0.6 mL) was added triethylamine (20 μL, 0.143 mmol). The pale-gold solution was heated at reflux for 25 min before a solution of $La(ClO_4)_3·6H_2O$ (0.0209 g, 0.038 mmol) in 2-propanol (0.5 mL) was added dropwise. A precipitate formed immediately. The cream suspension was stirred at reflux for an additional 1.5 h before it was cooled and centrifuged. The supernatant was removed, and the pellet was washed with 2-propanol (2-1 mL) and then air-dried on filter paper to give the title complex as a pale-tan solid (0.0177 g) containing 0.64 equiv of 2-propanol. $^1$H NMR (500 MHz, $D_2O$, pD≈9) S=7.87 (t, J=7.8 Hz, 2H), 7.54 (d, J=7.8 Hz, 2H), 7.39 (d, J=7.6 Hz, 2H), 5.21 (d, J=15.7 Hz, 2H), 4.44 (t, J=11.6 Hz, 2H), 4.09 (t, J=11.2 Hz, 4H), 4.01 (t, J=10.4 Hz, 2H), 3.74 (d, J=9.9 Hz, 2H), 3.65-3.60 (m, 4H), 3.58-3.47 (m, 4H), 3.44 (d, J=10.8 Hz, 2H), 2.75 (td, J=13.1, 2.7 Hz, 2H), 2.56 (d, J=13.9 Hz, 2H), 2.38 (d, J=14.0 Hz, 2H). $^{13}$C{$^1$H} APT NMR (126 MHz, $D_2O$, pD≈9) δ=172.62, 158.70, 150.19, 140.94, 126.89, 122.32, 71.88, 70.12, 69.20, 68.05, 60.14, 56.08, 54.01. EA Found: C, 35.16; H, 4.73; N, 5.91. Calc. for $C_{26}H_{35}LaN_4O_8·2ClO_4·2H_2O·0.64iPrOH$: C, 35.53; H, 4.71; N, 5.94. IR ($cm^{-1}$): 3443, 2913, 1630, 1596, 1461, 1370, 1265, 1083, 948, 839, 770, 678, 617, 513. HPLC $t_R$=18.104 min (Method A). HRMS (m/z): 669.14289, 335.07519; Calc for $[C_{26}H_{34}LaN_4O_8]^+$ and $[C_{26}H_{34}LaN_4O_8]^{2+}$, respectively: 669.14346, 335.07537.

Preparation of $[Lu(macropa)]^+$

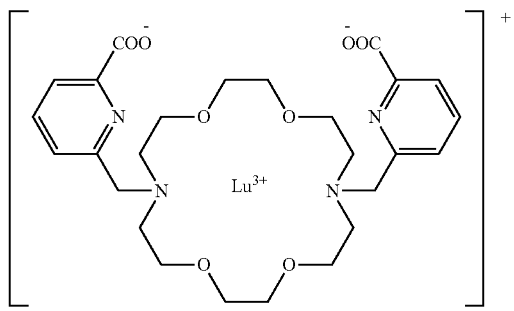

To a suspension $H_2$macropa·2HCl·4$H_2O$ (0.0730 g, 0.108 mmol) in 2-propanol (2 mL) was added triethylamine (61.5 μL, 0.441 mmol). The pale-gold solution was heated at reflux for 25 min before a solution of aq. $Lu(ClO_4)_3$ (0.1372 g, 0.118 mmol Lu) in 2-propanol (1.8 mL) was added dropwise. A precipitate formed immediately. After stirring at reflux or an additional 1 h, the cream suspension was triturated at RT for 20 h and then centrifuged. The supernatant was removed, and the pellet was washed with 2-propanol (2×2 mL) and then air-dried on filter paper to give the title complex as a pale-tan solid (0.0605 g) containing residual 2-propanol and triethylamine salt. $^1$H NMR (600 MHz, $D_2O$, pD≈7-8) δ=7.85 (t, J=7.7 Hz, 2H), 7.52 (d, J=7.8 Hz, 2H), 7.37 (d, J=7.6 Hz, 2H), 4.68 (d, J=16.3 Hz, 2H), 4.56 (td, J=11.2, 1.7 Hz, 2H), 4.42-4.38 (m, 2H), 4.23-4.19 (m, 6H), 4.07 (d, J=16.3 Hz, 2H), 3.96-3.87 (m, 2H), 3.71-3.63 (m, 4H), 3.38 (td, J=10.0, 4.7 Hz, 2H), 3.00 (m, 2H), 2.93 (d, J=13.1 Hz, 2H), 2.52 (dt, J=14.8, 4.5 Hz, 2H). $^{13}C\{^1H\}$ APT NMR (126 MHz, $D_2O$, pD≈7-8) δ=172.13, 158.67, 148.98, 141.81, 127.38, 122.83, 75.33, 73.12, 71.97, 71.70, 64.65, 57.37, 55.08. IR ($cm^{-1}$): 3400, 1639, 1396, 1274, 1091, 913, 770, 678, 622. HPLC $t_R$=not stable (Method A). HRMS (m/z): 705.17772; Calc for $[C_{26}H_{34}LuN_4O_8]^+$: 705.17788.

Preparation of dimethyl 4-aminopyridine-2,6-dicarboxylate (4)

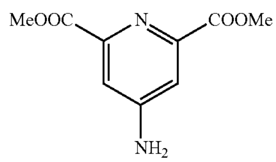

4

Dimethyl 4-azidopyridine-2,6-dicarboxylate (3, 0.9445 g, 4.0 mmol), 10% Pd/C (0.1419 g), and DCM:MeOH (1:1, 18 mL) were combined in a round-bottom flask. After purging the flask with a balloon of $H_2$, the reaction was stirred vigorously at room temperature under an $H_2$ atmosphere for 46 h. The gray mixture was diluted with DMF (450 mL) and filtered through a bed of Celite. Following a subsequent filtration through a 0.22 μm nylon membrane, the filtrate was concentrated at 60° C. under reduced pressure and further dried in vacuo to obtain 4 as a pale-tan solid (0.824 g, 98% yield). $^1$H NMR (500 MHz, DMSO-$d_6$): δ=7.36 (s, 2H), 6.72 (s, 2H), 3.84 (s, 6H). $^{13}C\{^1H\}$ APT NMR (126 MHz, DMSO-$d_6$): δ=165.51, 156.24, 148.05, 111.99, 52.29. IR ($cm^{-1}$): 3409, 3339, 3230, 1726, 1639, 1591, 1443, 1265, 996, 939, 787, 630, 543. HPLC $t_R$=9.369 min (Method B). HRMS (m/z): 211.07213 $[M+H]^+$; Calc: 211.07133.

Preparation of Ethyl 4-amino-6-(hydroxymethyl)picolinate (5)

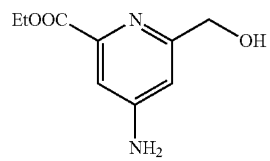

5

To a refluxing suspension of 4 (0.677 g, 3.22 mmol) in absolute EtOH (27 mL) was added $NaBH_4$ (0.1745 g, 4.61 mmol) portionwise over 1 h to give a pale-yellow suspension. The reaction was then quenched with acetone (32 mL) and concentrated at 60° C. under reduced pressure to a tan solid. The crude product was dissolved in $H_2O$ (60 mL) and washed with ethyl acetate (4×150 mL). The combined organics were dried over sodium sulfate and concentrated at 40° C. under reduced pressure. Further drying in vacuo yielded 5 as a pale-yellow solid (0.310 g, 49% yield). $^1$H NMR (300 MHz, DMSO-$d_6$): δ=7.07 (d, J=2.1 Hz, 1H), 6.78 (m, 1H), 6.32 (s, 2H), 5.30 (t, J=5.8 Hz, 1H), 4.39 (d, J=5.6 Hz, 2H), 4.26 (q, J=7.1 Hz, 2H), 1.28 (t, J=7.1 Hz, 3H). $^{13}$C APT NMR (126 MHz, DMSO-$d_6$) δ=165.57, 162.38, 155.68, 147.25, 108.50, 107.01, 63.95, 60.61, 14.24. IR ($cm^{-1}$): 3439, 3217, 2974, 2917, 1717, 1643, 1600, 1465, 1396, 1378, 1239, 1135, 1022, 974, 865, 783. HPLC $t_R$=8.461 min (Method B). HRMS (m/z): 197.09288 $[M+H]^+$; Calc: 197.09207.

Preparation of Ethyl 4-amino-6-(chloromethyl)picolinate (6)

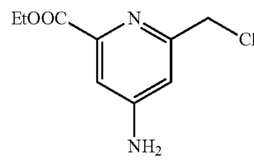

6

A mixture of thionyl chloride (2.5 mL) and 5 (0.301 g, 1.53 mmol) was stirred in an ice bath for 1 h, and then at RT for 30 min. The yellow-orange emulsion was concentrated at 40° C. under reduced pressure to an oily residue. The residue was neutralized with sat. aq. $NaHCO_3$(12 mL) and then extracted with ethyl acetate (75 mL). The organic extract was washed with $H_2O$ (2 mL), dried over sodium sulfate, and concentrated at 40° C. under reduced pressure. Further drying in vacuo gave 6 as an amber wax (0.287 g, 80% yield, corrected for residual ethyl acetate). $^1$H NMR (500 MHz, DMSO-$d_6$) δ=7.18 (d, J=2.1 Hz, 1H), 6.78 (d, J=2.1 Hz, 1H), 6.62 (br s, 2H), 4.62 (s, 2H), 4.29 (q, J=7.1 Hz, 2H), 1.30 (t, J=7.1 Hz, 3H). $^{13}C\{^1H\}$ APT NMR (126 MHz, DMSO-$d_6$) δ=164.75, 156.42, 156.19, 147.17, 109.79, 109.50, 60.97, 46.47, 14.15. IR ($cm^{-1}$): 3452, 3322, 3209, 2978, 2922, 1726, 1639, 1604, 1513, 1465, 1378, 1248, 1126, 1026, 983, 861, 783, 752, 700. HPLC $t_R$=12.364 min (Method B). HRMS (m/z): 215.05903 $[M+H]^+$; Calc: 215.05818.

Preparation of Methyl 6-((1,4,10,13-tetraoxa-7,16-diazacyclooctadecan-7-yl)methyl)picolinate ($9 \cdot 2TFA \cdot 1H_2O$)

9

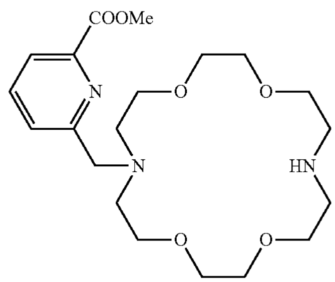

To a clear and colorless solution of 1,7,10,16-tetraoxa-4,13-diazacyclooctadecane (7, 1.9688 g, 7.5 mmol) and diisopropylethylamine (0.8354 g, 6.5 mmol) in dry ACN (1.075 L) at 75° C. was added dropwise a solution of 6 (0.9255 g, 5.0 mmol) in dry ACN (125 mL) over 2 h 40 min. The flask was then equipped with a condenser and drying tube, and the slightly-yellow solution was heated at reflux for 42 h. Subsequently, the dark-gold solution containing fine, white precipitate was concentrated at 60° C. under reduced pressure to an amber oil. To the crude oil was added 10% $MeOH/H_2O$ containing 0.1% TFA (10 mL). The slight suspension was filtered, and the filtrate was purified by preparative HPLC (Method A). Pure fractions were combined, concentrated at 60° C. under reduced pressure, and then lyophilized to give 9 (1.6350 g, 50% yield) as a pale-orange solid. $^1H$ NMR (500 MHz, DMSO-$d_6$) δ=8.75 (br s, 2H), 8.17-8.06 (m, 2H), 7.83 (dd, J=7.4, 1.5 Hz, 1H), 4.68 (br s, 2H), 3.91 (s, 3H), 3.85 (br t, J=5.1 Hz, 4H), 3.69 (t, J=5.1 Hz, 4H), 3.59 (br s, 8H), 3.50 (br s, 4H), 3.23 (br t, J=5.1 Hz, 4H). $^{13}C\{^1H\}$ APT NMR (126 MHz, DMSO-$d_6$) δ 164.68, 158.78-157.98 (q, TFA), 151.44, 147.13, 139.01, 128.63, 124.87, 120.08-113.01 (q, TFA), 69.33, 69.00, 65.31, 64.60, 56.43, 53.29, 52.67, 46.32. $^{19}F$ NMR (470 MHz, DMSO-$d_6$) δ=−73.84. EA Found: C, 43.88; H, 5.29; N, 6.28. Calc. for $C_{20}H_{33}N_3O_6 \cdot 2CF_3COOH \cdot 1H_2O$: C, 43.84; H, 5.67; N, 6.39. HPLC $t_R$=12.372 min (Method B). HRMS (m/z): 412.24568 $[M+H]^+$; Calc: 412.24421.

Preparation of Ethyl 4-amino-6-((16-((6-(methoxycarbonyl)pyridin-2-yl)methyl)-1,4,10,13-tetraoxa-7,16-diazacyclooctadecan-7-yl)methyl)picolinate (10)

10

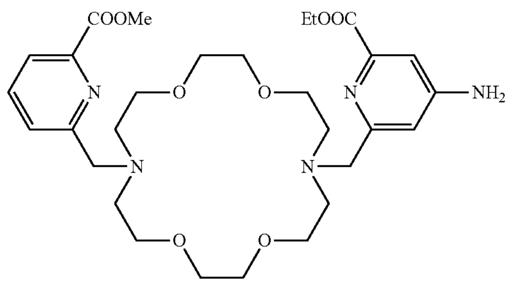

Into a round-bottom flask equipped with a condenser and drying tube were added 9 (0.4210 g, 0.64 mmol), $Na_2CO_3$ (0.3400 g, 3.2 mmol), and dry ACN (10 mL). The pale-yellow suspension was heated to reflux over 15 min, after which 6 (0.1508 g, 0.70 mmol, corrected for residual ethyl acetate) was added as a slight suspension in dry ACN (3.5 mL). The mixture was heated at reflux for 44 h and then filtered. The orange filtrate was concentrated at 60° C. under reduced pressure to an orange-brown oil (0.612 g), which was used in the next step without further purification. HRMS (m/z): 590.32021 $[M+H]^+$; Calc: 590.31844.

Preparation of 4-Amino-6-((16-((6-carboxypyridin-2-yl)methyl)-1,4,10,13-tetraoxa-7,16-diazacyclooctadecan-7-yl)methyl)picolinic acid (11.4TFA)

11

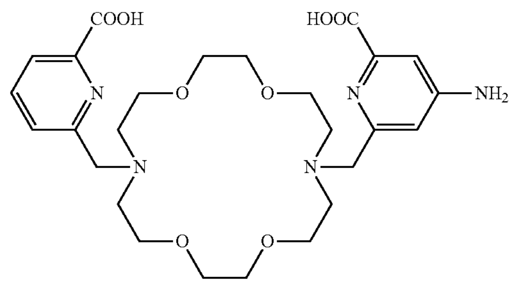

Compound 10 (0.612 g) was dissolved in 6 M HCl (7 mL) and heated at 90° C. for 17 h. The orange-brown solution containing slight precipitate was concentrated at 60° C. under reduced pressure to a pale-tan solid. To this solid was added 10% $MeOH/H_2O$ containing 0.1% TFA (3 mL). The slight suspension was filtered and the filtrate was purified by preparative HPLC using Method A. Pure fractions were combined, concentrated at 60° C. under reduced pressure, and then lyophilized to give 11 as an off-white solid (0.2974 g, 46% yield over 2 steps). $^1H$ NMR (500 MHz, DMSO-$d_6$) δ=8.13-8.08 (m, 2H), 7.80 (dd, J=7.3, 1.6 Hz, 1H), 7.64 (br s), 7.24 (d, J=2.3 Hz, 1H), 6.76 (d, J=2.3 Hz, 1H), 4.74 (s, 2H), 4.15 (s, 2H), 3.85 (t, J=5.0 Hz, 4H), 3.63 (t, J=5.1 Hz, 4H), 3.57-3.50 (m, 12H), 3.09 (br t, J=5.2 Hz, 4H). $^{13}C\{^1H\}$ NMR (126 MHz, DMSO-$d_6$) δ 165.96, 163.37, 159.47, 158.78-157.98 (q, TFA), 151.93, 151.64, 148.25, 144.68, 139.59, 128.43, 124.96, 120.79-113.68 (q, TFA), 109.40, 108.96, 70.03, 69.89, 67.09, 65.16, 57.28, 55.85, 54.47, 53.81. $^{19}F$ NMR (470 MHz, DMSO-$d_6$) δ=−74.03. EA Found: C, 40.60; H, 4.29; N, 7.04. Calc. for $C_{26}H_{37}N_5O_8 \cdot 4CF_3COOH$: C, 40.69; H, 4.12; N, 6.98. IR ($cm^{-1}$): 3387, 3161, 1735, 1670, 1204, 1130, 791, 722. HPLC $t_R$=11.974 min (Method B); 11.546 min (Method D). HRMS (m/z): 548.26883 $[M+H]^+$; Calc: 548.27149.

Preparation of 6-((16-((6-carboxypyridin-2-yl)methyl)-1,4,10,13-tetraoxa-7,16-diazacyclooctadecan-7-yl)methyl)-4-isothiocyanatopicolinic acid (12, macropa-NCS)

12

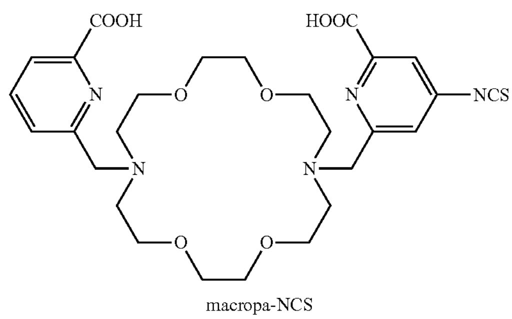

macropa-NCS

A white suspension of 11 (0.1598 g, 0.16 mmol) and $Na_2CO_3$ (0.2540 g, 2.4 mmol) was heated at reflux in acetone (10 mL) for 30 min before the slow addition of $CSCl_2$ (305 μL of $CSCl_2$, 85%, Acros Organics). The resulting orange suspension was heated at reflux for 3 h and then concentrated at 30° C. under reduced pressure to a pale-orange solid. The solid was dissolved portionwise in 10% ACN/$H_2O$ containing 0.2% TFA (8 mL total), filtered, and immediately purified by preparative HPLC using Method C.[108] Pure fractions were combined, concentrated at RT under reduced pressure to remove the organic solvent, and then lyophilized. Fractions that were not able to be concentrated immediately were frozen at −80° C. Isothiocyanate 12 was obtained as a mixture of white and pale-yellow solid (0.0547 g) and was stored at −80° C. in ajar of Drierite. Calculations from $^1$H NMR and $^{19}$F NMR spectra of a sample of 12 spiked with a known concentration of fluorobenzene estimated that 12 was isolated as a tetra-TFA salt. $^1$H NMR (400 MHz, DMSO-$d_6$) δ=8.17-8.06 (m, 2H), 8.00 (s w/fine splitting, 1H), 7.84 (d, J=1.5 Hz, 1H), 7.81-7.75 (d w/fine splitting, J=7.16 Hz, 1H), 4.71 (s, 2H), 4.64 (s, 2H), 3.89-3.79 (m, 8H), 3.62-3.46 (m, 16H). $^{19}$F NMR (470 MHz, DMSO-$d_6$) δ=−74.17. IR ($cm^{-1}$): −3500-2800, 2083, 2026, 1735, 1670, 1591, 1448, 1183, 1130, 796, 717. HPLC $t_R$=15.053 min (Method B); 13.885 min (Method D). HRMS (m/z): 590.22600 [M+H]$^+$; Calc: 590.22791.

Preparation of 6-((16-((6-carboxypyridin-2-yl)methyl)-1,4,10,13-tetraoxa-7,16-diazacyclooctadecan-7-yl)methyl)-4-(3-methylthioureido)picolinic acid (13, macropa-NHC(S)NHCH$_3$)

13

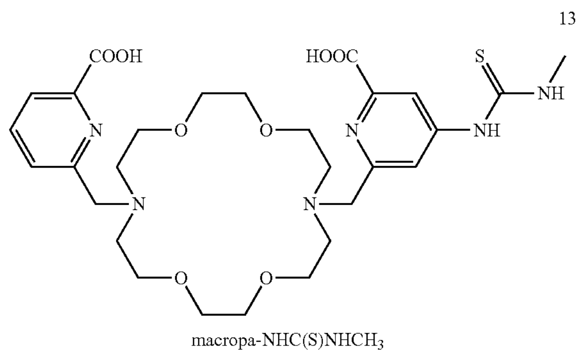 [SMILES: CNC(=S)Nc1cc(CN2CCOCCOCCN(Cc3cccc(C(=O)O)n3)CCOCCOCC2)nc(C(=O)O)c1]

macropa-NHC(S)NHCH$_3$

Compound 12 was prepared as described above using 0.0873 g (0.087 mmol) of 11, except the purification step was omitted. Instead, directly to the crude solid was added 2 M methylamine in THF (4 mL). The tan-orange suspension was stirred at RT for 2 h and then concentrated at RT under reduced pressure to a pale-peach solid. The solid was dissolved in 10% ACN/$H_2O$ containing 0.2% TFA (2 mL), filtered, and purified by preparative HPLC using Method C. Pure fractions were combined, concentrated at 50° C. under reduced pressure to remove the organic solvent, and then lyophilized. The dark-gold, slightly sticky solid was then recrystallized from ACN with $Et_2O$. The suspension was centrifuged, and the pellet was washed with $Et_2O$ (2×1.5 mL) and dried in vacuo to give 13 as a tan powder (0.0166 g, 22% unoptimized yield from 11). $^1$H NMR (600 MHz, DMSO-$d_6$) δ=10.56 (s, 1H), 8.64 (br s, 1H), 8.26 (s, 1H), 8.16 (s, 1H), 8.13-8.02 (m, 2H), 7.81-7.73 (d, J=7.40 Hz, 1H), 4.74-4.48 (m, 4H), 3.82 (br s, 8H), 3.57 (br s, 8H), 3.54-3.25 (m, 8H), 2.97 (d, J=4.4 Hz, 4H). $^{13}C\{^1H\}$ NMR (126 MHz, DMSO-$d_6$) δ 180.71, 165.44, 165.39, 158.77-157.95 (q, TFA), 151.04, 150.96, 149.79, 147.95, 147.71, 139.22, 127.76, 124.55, 119.68-112.66 (q, TFA), 116.45, 114.85, 69.36, 64.52, 64.50, 57.00, 56.75, 53.42, 53.37, 31.02. $^{19}$F NMR (470 MHz, DMSO-$d_6$) δ=−74.49. EA Found: C, 44.66; H, 5.36; N, 9.83. Calc. for $C_{28}H_{40}N_6O_8S·2CF_3COOH·1H_2O$: C, 44.34, H, 5.12; N, 9.70. HPLC $t_R$=14.067 min (Method B). HRMS (m/z): 621.26799 [M+H]$^+$; Calc: 621.27011.

Preparation of Macropa-($OCH_2CH_2$)-Ph-NCS

Figure 3:
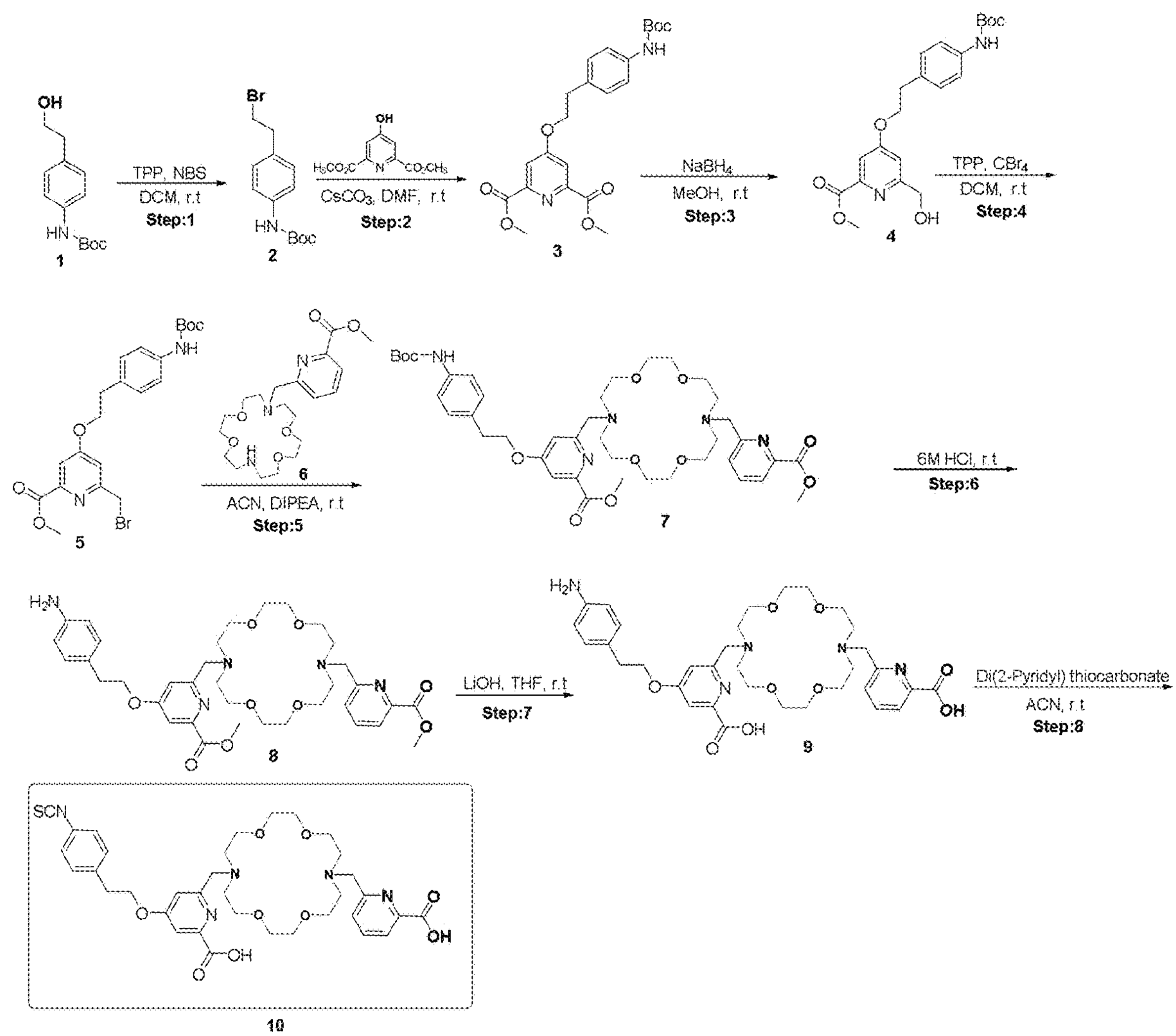
FIG. 3 provides a schematic overview of the synthesis of Macropa-($OCH_2CH_2$)-Ph-NCS (an embodiment of the present technology).

A schematic overview of the synthesis of an alternative embodiment of Macropa-NCS, having improved stability is provided in FIG. 3. This compound is evaluated as described below, and useful in the chelation of radionuclides for their conjunction to antibodies, antibody fragments (e.g., antigen-binding fragments), and peptides, and their consequent use in the manufacture of therapeutic compounds and targeted delivery of therapeutic radiation. The detailed synthesis information is provided below.

1

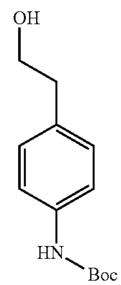

A solution of compound 1 (0.725 g, 3 mmol), $Ph_3P$ (0.802 g, 3.1 mmol) in $CH_2Cl_2$ (15 mL) was cooled to 0° C. under $N_2$. NBS (2.180.545 g, 3.3 mmol) was added portion wise for 5 min. The resulting solution was stirred for 2 hrs at 0° C. and concentrated. Resulting crude product was concentrated and purified by combi-flash (5-10% EtOAc in hexane) to give compound 2 (yield=76%).

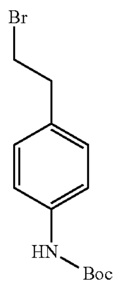

2

To a solution of dimethyl 4-hydroxypyridine-2,6-dicarboxylate (0.253 g, 1.2 mmol) and $Cs_2CO_3$ (0.650 g, 2 mmol) in DMF (6 mL) was added drop-wise compound 2 (0.299 g, 1 mmol) in DMF (2 mL) under a $N_2$ condition. The resulting solution was stirred for 24 hrs at room temperature. The DMF was removed under reduced pressure and water was added, extracted with DCM. Resulting crude product was concentrated and purified by combi-flash (5-10% EtOAc in hexane) to give compound 3 (yield=21%).

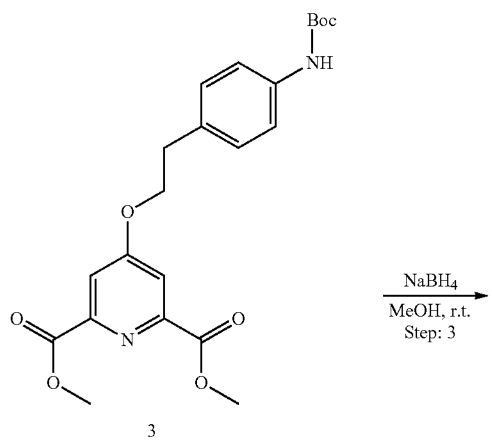

3

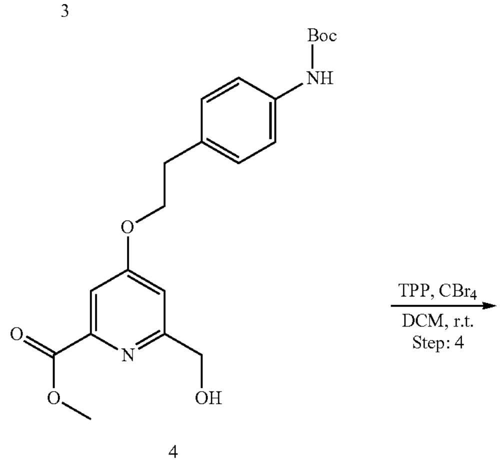

4

Compound 3 (0.215 g, 0.5 mmol) was dissolved in DCM: MeOH (2:1, 15 mL) and $NaBH_4$ (0.020 g, 0.6 mmol) was added in one portion at room temperature (under a $N_2$ condition). The resulting solution was stirred at same temperature for 3 hrs. The solvents were removed and water was added to the resulting residue and extracted into EtOAc. The organic layer was removed under reduced pressure and resulting crude product was purified by combi-flash (50-

100% EtOAc in hexane) to give compound 4 (yield=37%). A solution of compound 4 (0.201 g, 0.5 mmol), $CBr_4$ (0.198 g, 0.6 mmol) and $K_2CO_3$ (0.103 g, 0.75 mmol) in $CH_2Cl_2$ (25 mL) was cooled to 0° C. (under $N_2$) was added drop-wise a solution of $PPh_3$ (0.157 g, 0.6 mmol) in (DCM, 5 mL) for 10 min. The resulting reaction mixture was stirred for 12 hrs at room temperature. Solvent was removed to result in a crude reaction mixture, which was purified by combi-flash (EtOAc in hexane) to give compound 5 (yield=70%).

5

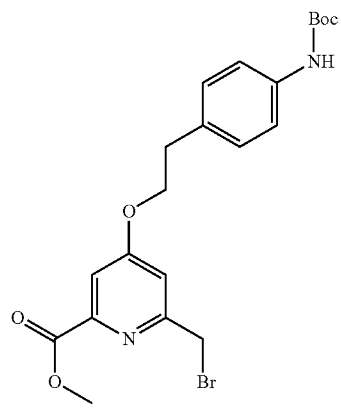

To a clear and colorless solution of 1,7,10,16-tetraoxa-4,13-diazacyclooctadecane (1.9688 g, 7.5 mmol) and diisopropylethylamine (0.8354 g, 6.5 mmol) in dry ACN (1.075 L) at 75° C. was added dropwise a solution of methyl 6-(chloromethyl)picolinate (0.9255 g, 5.0 mmol) in dry ACN (125 mL) over 2 h 40 min. The flask was then equipped with a condenser and drying tube, and the slightly-yellow solution was heated at reflux for 42 h. Subsequently, the dark-gold solution containing fine, white precipitate was concentrated at 60° C. under reduced pressure to an amber gummy solid, compound 6, which was used in the next step of the synthesis without any further purification.

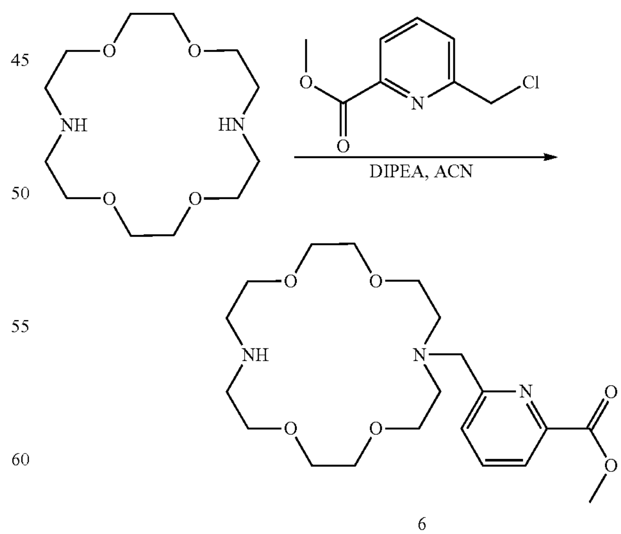

6

To a stirred solution of compound 6 (0.205 g, 0.5 mmol) and diisopropylethylamine (0.129 g, 1 mmol) in dry ACN (10 mL) was added compound 5 (0.233 g, 0.5 mmol) in dry ACN (2 mL). The resulting ion solution was stirred at r.t for 12 h. Solvent was removed and the crude compound was purified by combi-flash using MeOH in DCM to yield compound 7.

7

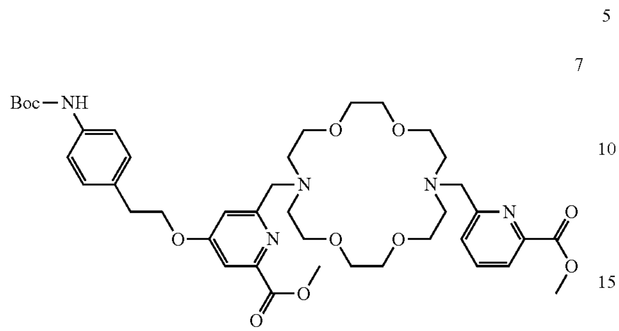

Compound 7 (0.08 g, 0.1 mmol) was dissolved in aq 6M HCl (5 mL) and stirred at room temperature for 2 h-3 h. After completion of the starting material (evidenced by LCMS), aq HCl was removed under reduced pressure and the crude reaction mixture, containing compound 8 was used in the next step of the synthesis without any further purification.

8

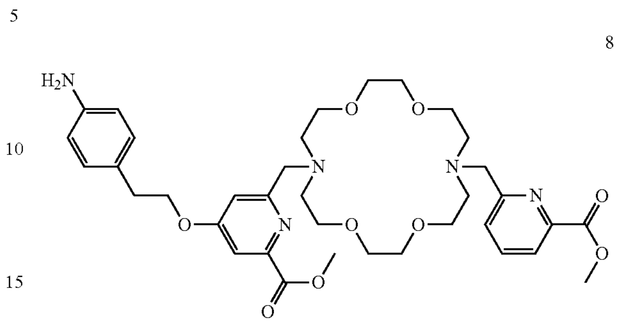

The crude deboc product was dissolved in THF:1M LiOH (1:1, 5 mL) and stirred until completion of the reaction. The resulting crude product was purified by prep-HPLC giving compound 9.

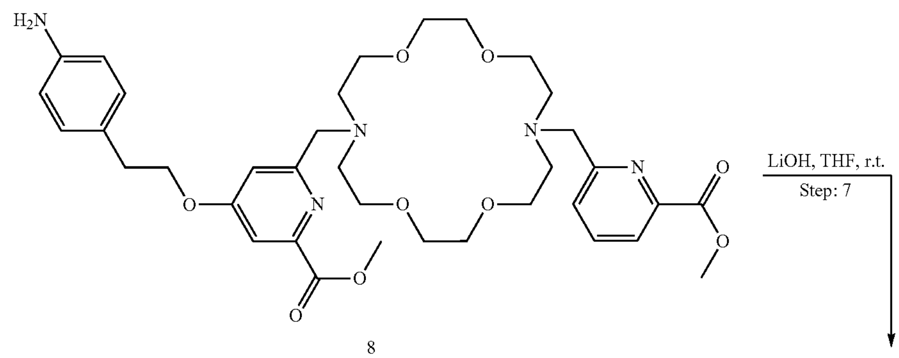

8

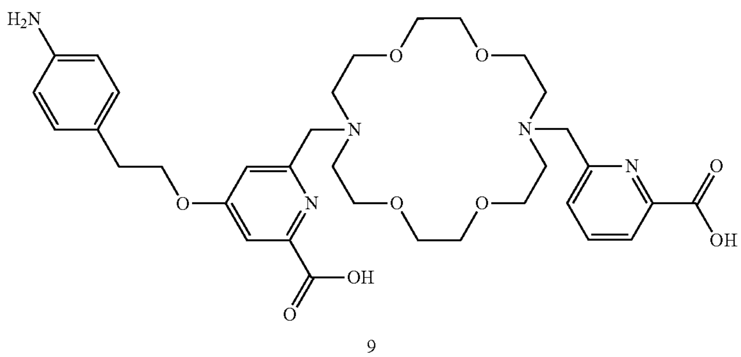

9

NEt3 (7.6 mg, 0.076 mmol) was added to a solution of compound 9 (26 mg, 0.038 mmol) in (8:2) acetonitrile and water (1 mL). Next, di-2-pyridyl thionocarbonate (18 m g, 0.076 mmol) was added at room temperature and stirred vigorously for 1 h. The crude reaction solution was directly purified by HPLC giving compound 10 (macropa-($OCH_2CH_2$)-Ph-NCS).

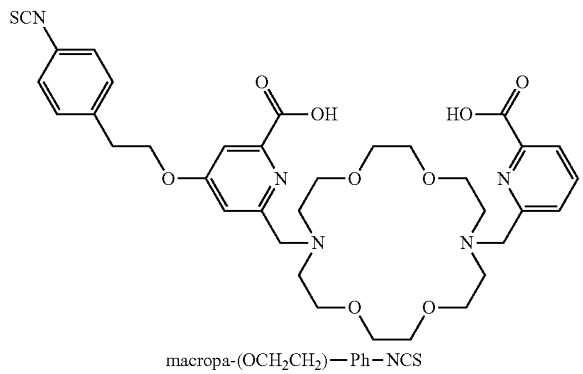

macropa-($OCH_2CH_2$)—Ph—NCS

X-Ray Diffraction Studies. Single crystals of $H_2$macropa·2HCl·4$H_2O$ suitable for x-ray diffraction were grown from a saturated $H_2O$:acetone (1:5) solution upon standing at room temperature. Single crystals of [La(Hmacropa)($H_2O$)]·($ClO_4$)$_2$ were grown via vapor diffusion of THF into an aqueous solution made acidic (pH ~2) upon addition of the complex. Single crystals of [Lu(macropa)]·$ClO_4$·DMF were grown via vapor diffusion of $Et_2O$ into a DMF solution of the complex.

X-ray diffraction data for $H_2$macropa·2HCl·4$H_2O$, [La (Hmacropa)($H_2O$)]·($ClO_4$)$_2$, and [Lu(macropa)]·$ClO_4$·DMF were collected on a Bruker APEX 2 CCD Kappa diffractometer (Mo Kα, λ=0.71073 Å) at 223 K. The structures were solved through intrinsic phasing using SHELXT[109] and refined against $F^2$ on all data by full-matrix least squares with SHELXL[110] following established refinement strategies.[111] All non-hydrogen atoms were refined anisotropically. Hydrogen atoms were included in the model at geometrically calculated positions and refined using a riding model. Hydrogen atoms bound to nitrogen and oxygen were located in the difference Fourier synthesis and subsequently refined semi-freely with the help of distance restraints. The isotropic displacement parameters of all hydrogen atoms were fixed to 1.2 times the U value of the atoms they are linked to (1.5 times for methyl groups). For [La(Hmacropa) ($H_2O$)]·($ClO_4$)$_2$, a partially occupied solvent molecule of water was included in the unit cell but could not be satisfactorily modeled. Therefore, that solvent was treated as a diffuse contribution to the overall scattering without using specific atom positions by the solvent masking function in Olex2.[112]

$La^{3+}$ and $Lu^{3+}$ Titrations with Macropa. The pH of a 10 mM 3-(N-morpholino)propanesulfonic acid (MOPS) buffer was adjusted to 7.4 using aqueous $NMe_4OH$. The ionic strength was set at 100 mM using $NMe_4Cl$. Stock solutions of $LaCl_3$·6.8$H_2O$ (40 mM) and $LuCl_3$·6$H_2O$ (21 mM) were prepared in 1 mM HCl. A stock solution of $H_2$macropa·2HCl·4$H_2O$ (8.8 mM) was prepared in MOPS buffer. From these stock solutions, titration solutions containing macropa (100 μM) and either $LaCl_3$ or $LuCl_3$ were prepared in MOPS. Each metal ion titration was carried out at RT by adding 5-10 μL aliquots of titrant to a cuvette containing 3000 μL of macropa (100 μM) in MOPS. Each sample was allowed to equilibrate for 5 min following every addition before a spectrum was acquired. Complexation of the metal ion was monitored by the decrease in absorbance at 268 nm, the $\lambda_{max}$ of macropa. Titrant was added until no further spectral changes were detected.

Kinetic Inertness of $La^{3+}$ and $Lu^{3+}$ Complexes of Macropa: Transchelation Challenge. A stock solution of ethylenediaminetetraacetic acid (EDTA, 100 mM) was made in MOPS buffer (prepared as described above) by adjusting the pH of the initial suspension to 6.6 using aqueous $NMe_4OH$. A stock solution of diethylenetriaminepentaacetic acid (DTPA, 125 mM) was prepared in $H_2O$ by adjusting the pH to 7.4 as described for EDTA. This solution was serially diluted with $H_2O$ to yield 12.5 mM and 1.25 mM solutions of DTPA.

The preformed $La^{3+}$ and $Lu^{3+}$ complexes of macropa were challenged with EDTA. Challenges were initiated by adding an aliquot of solution containing EDTA (98.7 mM) and macropa (100 μM) in MOPS buffer to each solution of complex. The final ratios of M:macropa:EDTA were approximately 1:1:20 (La) and 1:1:10 (Lu). Solutions were repeatedly analyzed by UV spectroscopy over the course of 21 days for any spectral changes. The final pH of each solution was between 7.18 and 7.25.

The complex formed in situ between $La^{3+}$ and macropa was more rigorously challenged with excess DTPA. A solution containing 500 μM of complex, prepared using the $LaCl_3$ and macropa stock solutions described above, was left to equilibrate for 5 min. Subsequently, it was portioned into cuvettes and diluted with either 125 mM DTPA, 12.5 mM DTPA, 1.25 mM DTPA, or MOPS to yield solutions containing 1000-, 100-, 10-, or 0-fold excess DTPA and 100 μM concentration of macropa. These solutions were repeatedly analyzed by UV spectroscopy over the course of 21 days for any spectral changes. The final pH of each solution was between 7.11 and 7.42.

$^{225}Ac$ Radiolabeling of Macropa and DOTA. $^{225}Ac$ and $^{225}Ra$ were produced by the spallation of uranium carbide, separated downstream from other radionuclides by a mass separator using the Isotope Separator and Accelerator (ISAC) isotope separation on-line (ISOL) facility at TRIUMF (Vancouver, BC, Canada), and were collected via literature protocols.[103,104] $^{225}Ac$ was then separated from $^{225}Ra$ via DGA column[105,106] (branched, 50-100 μm, Eichrom Technologies LLC) and obtained in 0.05 M $HNO_3$ for use in radiolabeling experiments. Aluminum-backed TLC plates (silica gel 60, $F_{254}$, EMD Millipore, Darmstadt, Germany) were used to analyze $^{225}Ac$ radiolabeling reaction progress. Instant thin layer chromatography paper impregnated with silica gel (iTLC-SG, Agilent Technologies, Mississauga, ON, Canada) was used in $La^{3+}$ and serum stability challenges. TLC plates were developed and then counted on a BioScan System 200 imaging scanner equipped with a BioScan Autochanger 1000 and WinScan software at least 8 h later to allow time for daughter isotopes to decay completely, ensuring that the radioactive signal measured was generated by parent $^{225}Ac$. Quantitative radioactivity measurements of $^{225}Ac$, $^{221}Fr$, and $^{213}Bi$ were determined via gamma-spectroscopy using a high-purity germanium (HPGe) detector (Canberra GR1520, Meriden, Conn.) calibrated using a NIST-traceable mixed $^{133}Ba$ and $^{152}Eu$ source. Detector dead time was maintained below 10% for all measurements. Data was analyzed using Genie 2000 software (v3.4, Canberra, Meriden, Conn.).

Concentration Dependence. Various concentrations of macropa and DOTA were radiolabeled with $^{225}Ac^{3+}$ to determine the lowest concentration at which >95% radiolabeling still occurred. Stock solutions of $H_2$macropa·2HCl·4$H_2O$ ($10^{-3}$-$10^{-8}$ M) and $H_4$DOTA ($10^{-3}$, $10^{-5}$, and $10^{-7}$M) were prepared in $H_2O$. For each radiolabeling reaction, ligand (10 μL) and $^{225}$Ac (10-26 kBq, 10-30 μL) were sequentially added to $NH_4$OAc buffer (pH 6, 0.15 M, 150 μL) to give final ligand concentrations of 5.3×$10^{-5}$-5.9×$10^{-10}$ M for macropa and 5.9×$10^{-5}$-5.9×$10^{-9}$ M for DOTA. The final pH of all labeling reactions was between 5.5 and 6. The reaction solutions were maintained at ambient temperature or 80° C. Reaction progress was monitored at 5 and 30 min by spotting 3-5 μL of the reaction solution onto TLC plates. The plates were developed with a mobile phase of 0.4 M sodium citrate (pH 4) containing 10% MeOH and then counted. Under these conditions, [$^{225}$Ac (macropa)]$^+$ and [$^{225}$Ac(DOTA)]$^-$ remained at the baseline ($R_F$=0) and any unchelated $^{225}$Ac ($^{225}$Ac-citrate) migrated with the solvent front ($R_F$=1). Radiochemical yields (RCYs) were calculated by integrating area under the peaks on the radiochromatogram and dividing the counts associated with the $^{225}$Ac-complex ($R_F$=0) by the total counts integrated along the length of the TLC plate.

Kinetic Inertness of $^{225}$Ac Complexes of Macropa and DOTA.

General. Stock solutions of La$(NO_3)_3$ (0.001 M or 0.1 M) were prepared in $H_2O$. To the radiolabeled samples containing macropa (10 μL of $10^{-5}$ M stock; 1.0×$10^{-10}$ moles) or DOTA (10 L of $10^{-3}$ M stock; 1.0×$10^{-8}$ moles) and $^{225}$Ac (10 μL, 26 kBq) in $NH_4$OAc buffer (pH 6, 0.15 M, 150 μL), a 50-fold mole excess of $La^{3+}$ was added (5 μL, of 0.001 M or 0.1 M stock were added to solutions containing macropa and DOTA, respectively). The solutions were kept at room temperature and analyzed by iTLC at several time points over the course of 8 days. The iTLC plates were developed using citric acid (0.05 M, pH 5) as the eluent. Under these conditions, [$^{225}$Ac(macropa)]$^+$ and [$^{225}$Ac(DOTA)]$^-$ remained at the baseline ($R_F$=0) and any unchelated $^{225}$Ac ($^{225}$Ac-citrate) migrated with the solvent front ($R_F$=1). Percent of complex remaining intact was calculated by integrating area under the peaks on the radiochromatogram and dividing the counts associated with the $^{225}$Ac-complex ($R_F$=0) by the total counts integrated along the length of the iTLC plate.

Transmetalation by $La^{3+}$. [$^{225}$Ac(macropa)]$^+$ and [$^{225}$Ac (DOTA)]$^-$ were prepared using $10^{-5}$ M and $10^{-3}$ M stock solutions (10 μL) of macropa and DOTA, respectively, to give final ligand concentrations of 5.9×$10^{-7}$ M (macropa) and 5.9×$10^{-5}$ M (DOTA). After confirming a radiochemical yield of >90% by TLC using 0.4 M sodium citrate (pH 4) containing 10% MeOH as the mobile phase, 160 μL of human serum (an equal volume based on labeling reaction volume) were added to each radiolabeled solution. A control solution was also prepared in which water was substituted for ligand. The solutions were monitored over the course of 8 days by iTLC. The plates were developed with EDTA (50 mM, pH 5) as the eluent. Under these conditions, [$^{225}$Ac (macropa)]$^+$ and [$^{225}$Ac(DOTA)]$^-$ complexes remained at the baseline ($R_F$=0) and any $^{225}$Ac ($^{225}$Ac-EDTA) that had been transchelated by serum migrated with the solvent front ($R_F$=1). Percent of complex remaining intact was calculated.

In Vivo Biodistribution of $^{225}$Ac Complexes of Macropa and DOTA. All experiments were approved by the Institutional Animal Care Committee (IACC) of the University of British Columbia and were performed in accordance with the Canadian Council on Animal Care Guidelines. A total of 9 female C57BL/6 mice (6-8 weeks old, 20-25 g) were used for the biodistribution study of each radiometal complex, n=3 for each time point.

Macropa (100 μL of a 1 mg/mL solution in $NH_4$OAc) was diluted with 387 μL of $NH_4$OAc (1 M, pH 7), and an aliquot (203 μL) of $^{225}$Ac$(NO_3)_3$ (~157 kBq) was then added; the pH of this solution was adjusted to 6.5-7 by the addition of 1 M NaOH (210 μL, trace metal grade). After 5 min at ambient temperature, the reaction solution was analyzed by TLC (0.4 M pH 4 sodium citrate as the eluent), which confirmed >95% radiochemical yield. The reaction was allowed to proceed overnight, and the radiochemical yield was again confirmed to be >95% the following morning. At this time, mice were anesthetized by 2% isoflurane, and approximately 100 μL (10-15 kBq) of the [$^{225}$Ac(macropa)]$^+$ complex were injected into the tail vein of each mouse. After injection, mice were allowed to recover and roam freely in their cages, and were euthanized by $CO_2$ inhalation at 15 min, 1 h, or 5 h (n=3 at each time point) post-injection. Blood was collected by cardiac puncture and placed into an appropriate test tube for scintillation counting. Tissues collected included heart, liver, kidneys, lungs, small intestine, large intestine, brain, bladder, spleen, stomach, pancreas, bone, thyroid, tail, urine, and feces. Tissues were weighed and then counted with a calibrated gamma counter (Packard, Cobra II model 5002) using three energy windows: 60-120 keV (window A), 180-260 keV (window B), and 400-480 keV (window C). Counting was performed both immediately after sacrifice and after 7 days; counts were decay corrected from the time of injection and then converted to the percentage of injected dose (% ID) per gram of tissue (% ID/g). No differences were noted between the data; therefore, the biodistributions are reported using the data acquired immediately using window A.

The biodistribution studies of [$^{22}$Ac(DOTA)] and $^{22}$Ac $(NO_3)_3$ were carried out as described above for [$^{225}$Ac (macropa)]$^+$, with the following modifications. [$^{225}$Ac (DOTA)$^-$ was prepared by adding $^{27S}$Ac$(NO_3)_3$ (338 μL, 1.1 MBq) to a solution of DOTA (100 μg, 20 mg/mL in $H_2O$) in $NH_4$OAc (467 μL, 0.15 M, pH 7). The pH of the solution was adjusted to 7 using $NH_4$OAc (150 μL, 1 M, pH 7) and the solution was heated at 85° C. for 45 min. RCY>99% was confirmed by TLC as described above. [$^{225}$Ac(DOTA)]$^-$ was diluted with saline to a final concentration of 0.05 MBq/100 μL, and 100 μL were injected into each mouse. $^{225}$Ac $(NO_3)_3$(~58 μL, 0.4 MBq) was diluted and injected in the same manner as [$^{225}$Ac(DOTA)]$^-$. One mouse that was to be euthanized at the 5 h time point in the [$^{225}$Ac(DOTA)]$^-$ study died shortly after injection. In the same manner, one mouse that was to be euthanized at the 1 h time point in the $^{225}$Ac$(NO_3)_3$ study died.

Hydrolysis of Macropa-NCS and p-SCN-Bn-DOTA. To screw-capped vials containing approximately 1 mg of macropa-NCS (compound 12, n=4) or p-SCN-Bn-DOTA (n=5) was added 1 mL of 0.1 M pH 9.1 $NaHCO_3$ buffer containing 0.154 M NaCl, which had been passed through a column of pre-equilibrated Chelex. After stirring for 1 min, each solution was filtered through a 0.2 μm PES or PTFE membrane. Five μL aliquots were removed from the vials at various time points over the course of 46-72 h and analyzed by HPLC. Method D was employed for macropa-NCS. Method B was employed for p-SCN-Bn-DOTA using an Epic Polar C18 column, 120 Å, 10 μm, 25 cm×4.6 mm (ES Industries, West Berlin, N.J.) at a flow rate of 1 mL/min. Between samplings, the vials were stored at room temperature (23±1° C.) away from light. Hydrolysis was considered complete once the peak at 13.8 min (corresponding to 12) or 18.417 min (corresponding top-SCN-Bn-DOTA) had disappeared or had negligible integration. A linear regression performed on the plots of In peak area versus time provided the pseudo-first order rate constant ($k_{obs}$) as the negative slope. The half-life ($t_{1/2}$) was calculated using the equation $t_{1/2}=0.693/k_{obs}$. The half-life of each compound is reported as the mean±1 standard deviation.

Titration of Macropa-NHC(S)$NHCH_3$ Conjugate with $La^{3+}$. The titration of the macropa-NHC(S)$NHCH_3$ conjugate (13) with $La^{3+}$ was carried out at pH 7.4 for macropa, except that the stock solution of 13 (0.760 mM) was prepared in ACN instead of MOPS. The amount of ACN in the sample did not exceed 3.3% by volume. A wait time of 3 min after the addition of each aliquot was found to be sufficient for the sample to reach equilibrium before spectral acquisition. Complexation of the metal ion was monitored using the increase in absorbance at 300 nm. The pH of the solution at the end of the titration was 7.43.

Kinetic Inertness of La-Macropa-NHC(S)$NHCH_3$: Transchelation Challenge. Solutions of diethylenetriaminepentaacetic acid (DTPA; 125 mM and 12.5 mM) were prepared in MOPS buffer (pH 7.4). A MOPS solution containing macropa-NHC(S)$NHCH_3$ (126.7 μM, 16.7% ACN by volume) and $LaCl_3$ (126.2 μM) was prepared using the stock solutions described above and was left to equilibrate for 10 min. Subsequently, it was portioned into cuvettes and diluted with either 125 mM DTPA, 12.5 mM DTPA, or MOPS to yield solutions containing 1000-, 100-, or 0-fold excess DTPA. The final concentration of macropa-NHC(S)$NHCH_3$ in each cuvette was 25.3 μM. These solutions were repeatedly analyzed by UV spectrophotometry over the course of 21 days for any spectral changes. The final pH of each solution was between 7.42 and 7.49. The experiment was performed in triplicate.

Exemplary Synthesis and Biological Activity of $^2$Ac-macropa-RPS-070

Preparation of Di-tert-butyl (((S)-1-(tert-butoxy)-6-(3-(3-ethynylphenyl)ureido)-1-oxohexan-2-yl)carbamoyl)-L-glutamate (214)

214

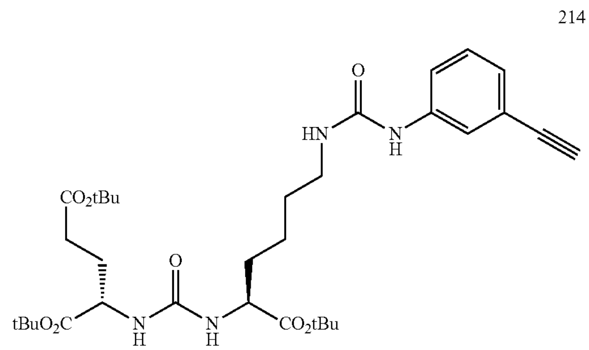 [SMILES: C#Cc1cccc(NC(=O)NCCCC[C@H](NC(=O)N[C@@H](CCC(=O)OC(C)(C)C)C(=O)OC(C)(C)C)C(=O)OC(C)(C)C)c1]

Alkyne 214 was prepared according to published methods[247] and isolated as an off-white powder. $^1$H NMR (500 MHz, $CDCl_3$) δ=7.90 (s, 1H), 7.58 (t, 1H, J=1.7 Hz), 7.51 (dd, 1H, $J_1$=8.2 Hz, $J_2$=1.3 Hz), 7.18 (t, 1H, J=7.9 Hz), 7.05 (d, 1H, J=7.7 Hz), 6.38 (d, 1H, J=7.9 Hz), 6.28 (br s, 1H), 5.77 (d, 1H, J=6.9 Hz), 4.32 (m, 1H), 4.02 (m, 1H), 3.53 (m, 1H), 3.05 (m, 1H), 3.00 (s, 1H), 2.39 (m, 2H), 2.07 (m, 1H), 1.88 (m, 1H), 1.74 (m, 1H), 1.62 (m, 1H), 1.49-1.37 (m, 4H), 1.41 (s, 18H), 1.37 (s, 9H).

Preparation of 2,5-Dioxopyrrolidin-1-yl $N^2$-(((9H-fluoren-9-yl)methoxy)carbonyl)-$N^6$-(tert-butoxycarbonyl)-L-lysinate (215)

215

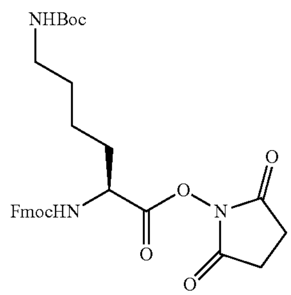

A suspension of Fmoc-L-Lys(Boc)-OH (5.0 g, 10.7 mmol) and N,N'-disuccinimidyl carbonate (2.74 g, 10.7 mmol) in $CH_2Cl_2$ (50 mL) was stirred at room temperature under argon. Then DIPEA (1.86 mL, 10.7 mmol) was added, and the suspension was stirred overnight. The solvent was evaporated under reduced pressure and the crude product was purified by flash chromatography (0-100% EtOAc in hexane). Lysine 215 was isolated as a white powder (2.5 g, 41%). $^1$H NMR (500 MHz, $CDCl_3$) δ=7.76 (d, 2H, J=7.6 Hz), 7.59 (d, 2H, J=7.3 Hz), 7.40 (t, 2H, J=7.4 Hz), 7.32 (t, 2H, J=7.3 Hz), 5.46 (br s, 1H), 4.71 (m, 2H), 4.45 (m, 2H), 4.23 (t, 1H, J=6.6 Hz), 3.14 (br s, 2H), 2.85 (s, 4H), 2.02 (m, 1H), 1.92 (m, 1H), 1.58 (m, 4H), 1.44 (s, 9H).

Preparation of tert-Butyl $N^2$-($N^2$-(((9H-fluoren-9-yl)methoxy)carbonyl)-$N^6$-(tert-butoxycarbonyl)-L-lysyl)-$N^6$-((benzyloxy)carbonyl)-L-lysinate (216)

216

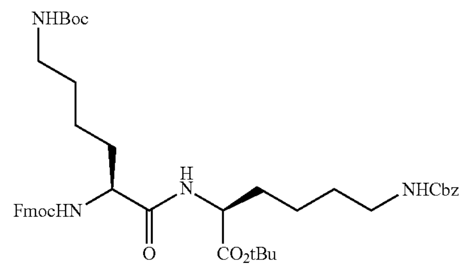

A suspension of L-Lys(Z)-OtBu·HCl (1.49 g, 4.0 mmol) in $CH_2Cl_2$ (15 mL) was treated with DIPEA (0.87 mL, 5.0 mmol). To the resulting mixture was added a solution of lysine 215 (2.2 g, 3.9 mmol) in $CH_2Cl_2$ (10 mL), and the reaction was stirred overnight at room temperature under argon. It was then washed with saturated NaCl solution, and the organic layer was dried over $MgSO_4$, filtered and concentrated under reduced pressure. The crude product was purified by flash chromatography (0-100% EtOAc in hexane), and di-lysine 216 was isolated as a white powder (2.2 g, 72%). $^1$H NMR (500 MHz, $CDCl_3$) δ=7.76 (d, 2H, J=7.5 Hz), 7.59 (d, 2H, J=7.3 Hz), 7.40 (t, 2H, J=7.5 Hz), 7.32 (m, 8H), 6.69 (br s, 1H), 5.60 (br s, 1H), 5.06 (m, 4H), 4.72 (br s, 1H), 4.43 (m, 1H), 4.38 (m, 1H), 4.21 (m, 1H), 3.14 (m, 4H), 1.85 (m, 2H), 1.73 (m, 2H), 1.50 (m, 4H), 1.46 (s, 9H), 1.44 (s, 9H), 1.39 (m, 4H).

Preparation of 2,5-Dioxopyrrolidin-1-yl 2-(4-iodophenyl)acetate (217)

217

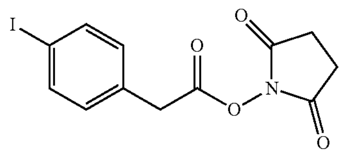

A solution of 2-(4-iodophenyl)acetic acid (786 mg, 3.0 mmol) and EDC-HCl (671 mg, 3.5 mmol) in $CH_2Cl_2$ (20 mL) was stirred for 15 min at room temperature under argon. Then N-hydroxysuccinimide (368 mg, 3.2 mmol) and $NEt_3$ (0.56 mL, 4.0 mmol) were added and the reaction was stirred for 7 h. It was then washed with saturated NaCl solution, and the organic layer was dried over $MgSO_4$, filtered and concentrated under reduced pressure. The crude residue was purified by flash chromatography (0-100% EtOAc in hexane), and the NHS ester 217 was isolated as a white solid (760 mg, 70%). $^1H$ NMR (500 MHz, $CDCl_3$) δ=7.69 (d, 2H, J=7.9 Hz), 7.09 (d, 2H, J=7.9 Hz), 3.88 (s, 2H), 2.83 (s, 4H).

Preparation of tert-Butyl $N^2$-($N^2$-(1-azido-3,6,9,12,15,18-hexaoxahenicosan-21-oyl)-$N^6$-(tert-butoxycarbonyl)-L-lysyl)-$N^6$-((benzyloxy)carbonyl)-L-lysinate (218)

218

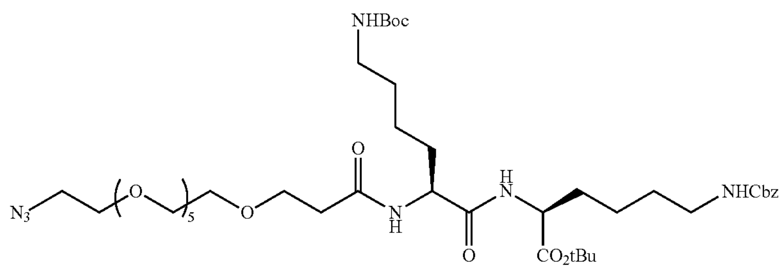

To a solution of Fmoc-protected di-lysine 216 (768 mg, 0.97 mmol) in $CH_2Cl_2$ (4 mL) was added $NHEt_2$ (2.07 mL, 20 mmol). The solution was stirred overnight at room temperature. The solvents were removed under reduced pressure, and the crude product, a yellow oil, was used without further purification. To a solution of this oil (183 mg, 0.32 mmol) in $CH_2Cl_2$ (3 mL) were added successively solutions of $NEt_3$ (57 μL, 0.41 mmol) in $CH_2Cl_2$ (1 mL) and azido-$PEG_6$-NHS ester (100 mg, 0.21 mmol; Broadpharm, USA) in $CH_2Cl_2$ (1 mL), and the reaction was stirred overnight at room temperature. It was then diluted with $CH_2Cl_2$ and washed successively with $H_2O$ and saturated NaCl solution. The organic layer was dried over $MgSO_4$, filtered and concentrated under reduced pressure to give azide 218 as a colorless oil (184 mg; 95%) without need for further purification. Mass (ESI+): 926.4 $[M+H]^+$. Calc. Mass=925.54.

Preparation of Di-tert-butyl (((S)-1-(tert-butoxy)-6-(3-(3-(1-((9S,12S)-9-(tert-butoxycarbonyl)-12-(4-((tert-butoxycarbonyl)amino)butyl)-3,11,14-trioxo-1-phenyl-2,17,20,23,26,29,32-heptaoxa-4,10,13-triazatetratriacontan-34-yl)-1H-1,2,3-triazol-4-yl)phenyl)ureido)-1-oxohexan-2-yl)carbamoyl)-L-glutamate (219)

219

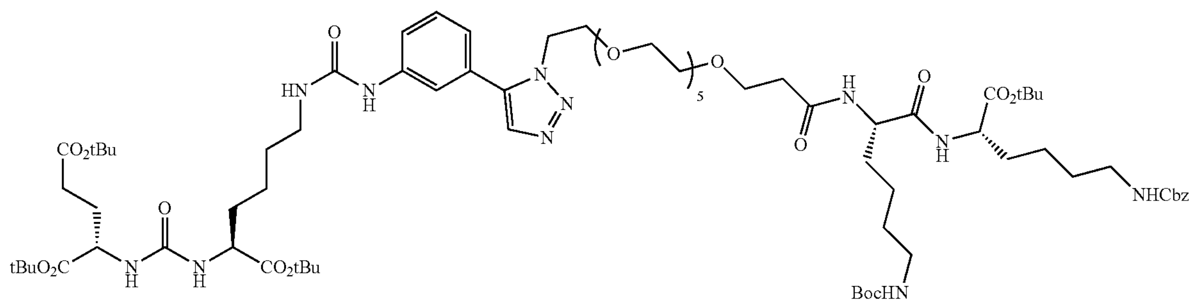

A solution of 100 μL of 0.5 M $CuSO_4$ and 100 μL of 1.5 M sodium ascorbate in DMF (0.5 mL) was mixed for 5 min and was then added to a solution of 218 (184 mg, 0.20 mmol) and 214 (132 mg, 0.21 mmol) in DMF (2.5 mL). The resulting mixture was stirred at room temperature for 45 min. It was then concentrated under reduced pressure and the crude residue was purified by flash chromatography (0-30% MeOH in EtOAc) to give triazole 219 as an orange oil (285 mg; 87%). Mass (ESI+): 1557.2 $[M+H]^-$. Calc. Mass=1555.90.

Preparation of Di-tert-butyl (((S)-1-(tert-butoxy)-6-(3-(3-(1-((23S,26S)-26-(tert-butoxycarbonyl)-23-(4-((tert-butoxycarbonyl)amino)butyl)-33-(4-iodophenyl)-21,24,32-trioxo-3,6,9,12,15,18-hexaoxa-22,25,31-triazatritriacontyl)-1H-1,2,3-triazol-4-yl)phenyl)ureido)-1-oxohexan-2-yl)carbamoyl)-L-glutamate (220)

220

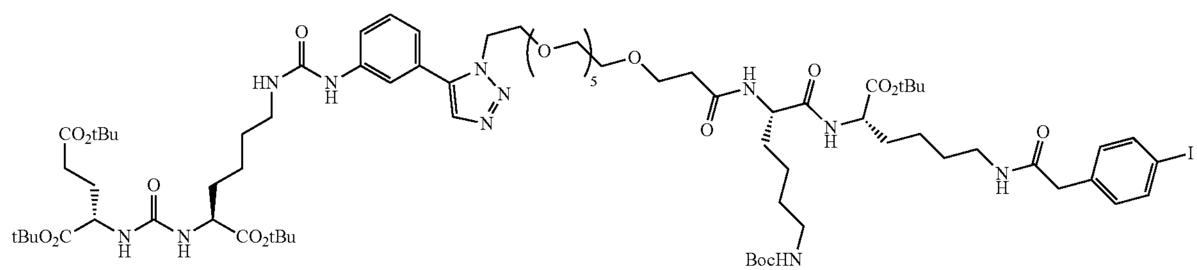

Cbz-Protected triazole 219 (285 mg, 0.18 mmol) was dissolved in MeOH (15 mL) in a two-neck flask. To the solution was added 10% Pd/C (20 mg), and the suspension was shaken and the flask evacuated. The suspension was then placed under an $H_2$ atmosphere and stirred overnight. It was filtered through celite, and the filter cake was washed three times with MeOH. The combined filtrate was concentrated under reduced pressure to give the free amine as a colorless oil (117 mg; 45%) that was used without further purification. Mass (ESI+): 1423.8 $[M+H]^+$. Calc. Mass=1422.77. To a solution of the amine (117 mg, 82 μmol) in $CH_2Cl_2$ (4 mL) was added a solution of DIPEA (23 μL, 131 mmol) in $CH_2Cl_2$ (1 mL), and the mixture was stirred at room temperature under argon. Then a solution of 217 (37 mg, 103 μmol) in $CH_2Cl_2$ (2 mL) was added, and the reaction was stirred at room temperature for 2 h. It was then poured into $H_2O$ (10 mL) and the layers were separated. The organic layer was dried over $MgSO_4$, filtered and concentrated under reduced pressure to give the crude product as a colorless semi-solid. The crude product was purified by prep TLC (10% MeOH in EtOAc) to give phenyl iodide 220 as a colorless oil (34 mg; 25%). Mass (ESI+): 1666.6 $[M+H]^+$. Calc. Mass=1665.80.

Preparation of (((S)-1-Carboxy-5-(3-(3-(1-((23S,26S)-26-carboxy-23-(4-(3-(2-carboxy-6-((16-((6-carboxypyridin-2-yl)methyl)-1,4,10,13-tetraoxa-7,16-diazacyclooctadecan-7-yl)methyl)pyridin-4-yl)thioureido)butyl)-33-(4-iodophenyl)-21,24,32-trioxo-3,6,9,12,15,18-hexaoxa-22,25,31-triazatritriacontyl)-1H-1,2,3-triazol-4-yl)phenyl)ureido)pentyl)carbamoyl)-L-glutamic acid (221, macropa-RPS-070)

221

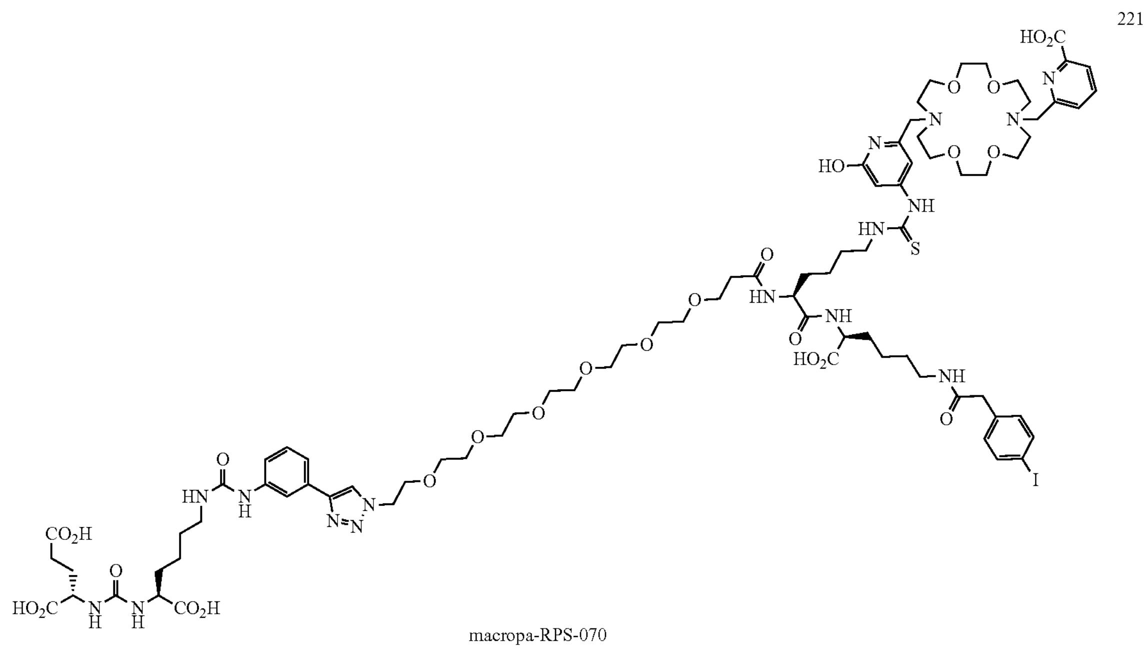 [SMILES: O=C(O)CC[C@H](NC(=O)N[C@@H](CCCCNC(=O)Nc1cccc(-c2cn(CCOCCOCCOCCOCCOCCOCCC(=O)N[C@@H](CCCCNC(=S)Nc3cc(O)nc(CN4CCOCCOCCN(Cc5cccc(C(=O)O)n5)CCOCCOCC4)c3)C(=O)N[C@@H](CCCCNC(=O)Cc3ccc(I)cc3)C(=O)O)nn2)c1)C(=O)O)C(=O)O]

macropa-RPS-070

To a solution of 220 (34 mg, 20 μmol) in $CH_2Cl_2$ (2 mL) was added TFA (0.5 mL), and the reaction was stirred at room temperature for 5 h. It was then concentrated under reduced pressure, and the crude product was diluted with $H_2O$ and lyophilized to give the free amine as a TFA salt. Mass (ESI+): 1342.5 $[M+H]^+$. Mass (ESI−): 1340.6 $[M-H]^-$ Calc. Mass=1341.50. To a solution of the amine (9 mg, 6.7 μmol) in DMF (0.5 mL) was added a solution of macropa-NCS (15 mg, 25.4 μmol) in DMF (0.5 mL). Then DIPEA (300 μL, 1.72 mmol) was added and the reaction was stirred at room temperature for 2 h. The volatiles were removed under reduced pressure and the crude product was purified by prep HPLC to give macropa-RPS-070 (221) as a white powder (5.4 mg; 42%). Mass (ESI+): 1932.76 $[M+H]^+$. 1931.09 $[M+H]^-$. Calc. Mass=1931.91.

Preparation of Radiosynthesis of $^{225}$Ac-macropa-RPS-070

General. All reagents were purchased from Sigma Aldrich unless otherwise noted, and were reagent grade. Hydrochloric acid (HCl) was traceSELECT® (>99.999%) for trace analysis quality. Aluminum-backed silica thin layer chromatography (TLC) plates were purchased from Sigma Aldrich. Stock solutions of 0.05 M HCl and 1 M $NH_4OAc$ were prepared by dilution in Milli-Q® water.

Radiolabeling Procedure. To a solution of $^{225}Ac(NO_3)_3$ (Oak Ridge National Laboratory, USA) in 0.05 M HCl (17.9 MBq in 970 μL) was added 20 μL of a 1 mg/mL solution of macropa-RPS-070 in DMSO. The pH was raised to 5-5.5 by addition of 90 μL 1 M $NH_4OAc$. The reaction was allowed to stand at room temperature for 20 min with periodic shaking. Then, 200 μL of the reaction solution was removed and diluted with 3.8 mL of normal saline (0.9% NaCl in deionized $H_2O$; VWR) to give a solution with a concentration of 910 kBq/mL. An aliquot was removed from the final solution and spotted onto an aluminum-backed silica TLC plate to determine radiochemical yield. An aliquot of the $^{225}Ac(NO_3)_3$ solution in 0.05M HCl was spotted in a parallel lane as a control. The plate was immediately run in a 10% v/v MeOH/10 mM EDTA mobile phase, and then allowed to stand for 8 h to enable radiochemical equilibrium to be reached. The plate was visualized on a Cyclone Plus Storage Phosphor System (Perkin Elmer) following a 3-min exposure on the phosphor screen. The radiochemical yield was expressed as a ratio of $^{225}$Ac-macropa-RPS-070 to total activity and was determined to be 98.1%.

Biodistribution Studies with $^{225}$Ac-Macropa-RPS-070.

Cell Culture. The PSMA-expressing human prostate cancer cell line, LNCaP, was obtained from the American Type Culture Collection. Cell culture supplies were from Invitrogen unless otherwise noted. LNCaP cells were maintained in RPMI-1640 medium supplemented with 10% fetal bovine serum (Hyclone), 4 mM L-glutamine, 1 mM sodium pyruvate, 10 mM N-2-hydroxyethylpiperazine-N-2-ethanesulfonic acid (HEPES), 2.5 mg/mL D-glucose, and 50 μg/mL gentamicin in a humidified incubator at 37° C./5% $CO_2$. Cells were removed from flasks for passage or for transfer to 12-well assay plates by incubating them with 0.25% trypsin/ethylenediaminetetraacetic acid (EDTA).

Inoculation of Mice with Xenografts. All animal studies were approved by the Institutional Animal Care and Use Committee of Weill Cornell Medicine and were undertaken in accordance with the guidelines set forth by the USPHS Policy on Humane Care and Use of Laboratory Animals. Animals were housed under standard conditions in approved facilities with 12 h light/dark cycles. Food and water was provided ad libitum throughout the course of the studies. Hairless male nu/nu mice were purchased from the Jackson Laboratory. For inoculation in mice, LNCaP cells were suspended at $4 \times 10^7$ cells/mL in a 1:1 mixture of PBS: Matrigel (BD Biosciences). Each mouse was injected in the left flank with 0.25 mL of the cell suspension. Biodistributions were conducted when tumors were in the range 100-400 $mm^3$.

Biodistribution of $^{225}$Ac-macropa-RPS-070 in LNCaP xenograft mice. Fifteen LNCaP xenograft tumor-bearing mice (5 per time point) were injected intravenously with a bolus injection of 85-95 kBq and 100 ng (50 pmol) of each ligand. The mice were sacrificed by cervical dislocation at 4, 24 and 96 h post injection. A blood sample was removed, and a full biodistribution study was conducted on the following organs (with contents): heart, lungs, liver, small intestine, large intestine, stomach, spleen, pancreas, kidneys, muscle, bone, and tumor. Tissues were weighed and counted on a 2470 Wizard Automatic Gamma Counter (Perkin Elmer). 1% ID/mL samples were counted prior to and following each set of tissue samples to enable decay correction to be undertaken. Counts were corrected for decay and for activity injected, and tissue uptake was expressed as percent injected dose per gram (% ID/g). Standard error measurement was calculated for each data point.

TABLE F

Organ distribution of $^{225}$Ac-macropa-RPS-070 at t = 4 h, 24 h, and 96 h following intravenous injection in LNCaP xenograft mice (n = 5 per time point). Values expressed as % ID/g.

| | 1 | 2 | 3 | 4 | 5 | Mean | SEM |
|---|---|---|---|---|---|---|---|
| **4 h** | | | | | | | |
| Blood | 0.90654 | 0.55246 | 1.11808 | 0.8276 | 0.65638 | 0.81221 | 0.0986 |
| Heart | 0.75759 | 0.65317 | 0.77395 | 0.75148 | 0.6585 | 0.71894 | 0.02604 |
| Lungs | 0.99558 | 0.60669 | 1.25979 | 0.98587 | 0.88664 | 0.94681 | 0.10516 |
| Liver | 1.62187 | 1.34632 | 1.74207 | 1.68077 | 1.3957 | 1.55735 | 0.0788 |
| Small Intestine | 0.1998 | 0.16282 | 0.3104 | 0.24413 | 0.17094 | 0.21762 | 0.02721 |
| Large Intestine | 1.36298 | 0.65162 | 1.27419 | 0.91656 | 0.81901 | 1.00487 | 0.13563 |
| Stomach | 0.33963 | 0.2471 | 0.30417 | 0.4109 | 0.21221 | 0.3028 | 0.03489 |
| Spleen | 1.40902 | 0.70804 | 1.61264 | 1.10815 | 0.8756 | 1.14269 | 0.16632 |
| Pancreas | 0.55487 | 0.41637 | 0.55317 | 0.4675 | 0.6604 | 0.53047 | 0.04182 |
| Kidneys | 65.5884 | 20.5274 | 108.233 | 33.654 | 33.0707 | 52.2146 | 15.8618 |
| Muscle | 0.68006 | 0.80579 | 0.72817 | 0.67666 | 0.65617 | 0.70937 | 0.02684 |
| Bone | 1.14861 | 1.12335 | 1.48731 | 0.92036 | 1.15463 | 1.16685 | 0.09106 |
| Tumor | 6.73177 | 10.7309 | 23.8367 | 15.3682 | 7.50352 | 12.8342 | 3.1429 |
| **24 h** | | | | | | | |
| Blood | 0.34825 | 0.31324 | 0.22083 | 0.29453 | 0.27697 | 0.29076 | 0.0211 |
| Heart | 0.52256 | 0.56334 | 0.4521 | 0.47914 | 0.46483 | 0.49639 | 0.02052 |
| Lungs | 0.53778 | 0.45077 | 0.46083 | 0.4286 | 0.44831 | 0.46526 | 0.01887 |
| Liver | 1.57844 | 1.47552 | 1.13776 | 1.14264 | 1.48473 | 1.36382 | 0.09305 |
| Small Intestine | 0.08784 | 0.09914 | 0.08822 | 0.09466 | 0.10376 | 0.09473 | 0.00309 |
| Large Intestine | 0.13296 | 0.1259 | 0.13252 | 0.13425 | 0.13176 | 0.13148 | 0.00145 |
| Stomach | 0.1296 | 0.12119 | 0.1119 | 0.14675 | 0.15329 | 0.13255 | 0.00773 |
| Spleen | 0.62075 | 0.65764 | 0.62013 | 0.57685 | 0.58554 | 0.61218 | 0.01443 |
| Pancreas | 0.39847 | 0.39119 | 0.50347 | 0.33315 | 0.31944 | 0.38914 | 0.03252 |
| Kidneys | 4.98792 | 4.25707 | 3.94586 | 3.66457 | 4.10348 | 4.19178 | 0.22185 |
| Muscle | 0.61193 | 0.5149 | 0.44832 | 0.78028 | 0.44579 | 0.56025 | 0.06276 |
| Bone | 1.27255 | 1.06645 | 0.83943 | 1.00576 | 0.69755 | 0.97635 | 0.09828 |
| Tumor | 11.6163 | 9.26927 | 7.50158 | 4.41446 | 8.04683 | 8.16969 | 1.17583 |
| **96 h** | | | | | | | |
| Blood | 0.19042 | 0.19188 | 0.15206 | 0.16528 | 0.23822 | 0.18757 | 0.01475 |
| Heart | 0.39939 | 0.42398 | 0.42861 | 0.45863 | 0.45595 | 0.43331 | 0.01098 |
| Lungs | 0.30165 | 0.50912 | 0.46944 | 0.37811 | 0.36979 | 0.40562 | 0.03717 |
| Liver | 0.79406 | 0.8144 | 0.73301 | 0.7917 | 0.79415 | 0.78546 | 0.01374 |
| Small Intestine | 0.04372 | 0.0577 | 0.03752 | 0.04431 | 0.04136 | 0.04492 | 0.00341 |
| Large Intestine | 0.04349 | 0.09663 | 0.04522 | 0.04198 | 0.03927 | 0.05332 | 0.01087 |
| Stomach | 0.03442 | 0.04708 | 0.03448 | 0.02845 | 0.02366 | 0.03362 | 0.00393 |
| Spleen | 0.48373 | 0.394 | 0.44261 | 0.43481 | 0.53966 | 0.45896 | 0.02469 |
| Pancreas | 0.09848 | 0.37696 | 0.30549 | 0.31625 | 0.33352 | 0.28614 | 0.04847 |
| Kidneys | 1.30286 | 1.3239 | 2.00405 | 1.39866 | 1.45955 | 1.4978 | 0.12958 |
| Muscle | 0.3022 | 0.52492 | 0.25089 | 0.29815 | 0.2528 | 0.32579 | 0.05095 |
| Bone | 0.86391 | 0.86874 | 0.83831 | 1.12223 | 0.82042 | 0.90272 | 0.05557 |
| Tumor | 4.04259 | 4.07799 | 6.73954 | 4.58107 | 4.84503 | 4.85724 | 0.49449 |

Conjugation of Macropa-NCS and n-SCN-Bn DOTA to Trastuzumab.

General. All glassware was washed overnight in 1M HCl. Saline (0.154 M NaCl) and all buffer solutions were passed through a column of Chelex-100 pre-equilibrated with the appropriate buffer. Trastuzumab (Tmab, Genentech) was purified using a Zeba spin desalting column (2 mL or 5 mL, 40 MWCO, Thermo Scientific, Waltham, Mass.) according to the manufacturer's protocol, with saline as the mobile phase. The concentration of purified Tmab was calculated via the Beer-Lambert law using $A_{280}$ and an $\varepsilon_{280}$ of 1.446 mL $mg^{-1}$ $cm^{-1}$.[107] Purified Tmab and Tmab conjugates were stored at 4° C.

Conjugation of Macropa-NCS to Tmab. A stock solution containing 4.4 mg/mL of macropa-NCS (12) was prepared in 0.1 M pH 9.1 $NaHCO_3$ buffer containing 0.154 M NaCl and was stored at −80° C. The stability of 12 during storage was verified by analytical HPLC. To a portion of Tmab in saline (74 μL) were added 12 (52 μL) and $NaHCO_3$ buffer (266 μL), so that the final concentrations of Tmab and 12 were 5.1 mg/mL and 0.59 mg/mL, respectively. Macropa-NCS was estimated to be in 16-fold molar excess to Tmab based on a molecular weight of 1045.76 g/mol for 12 (tetra-TFA salt). The pH of this solution was between 8 and 9 by litmus paper. The solution was rocked gently at room temperature for 17.5 h and then purified using a spin column.

Conjugation of p-NCS-Bn-DOTA to Tmab. A stock solution containing 3.05 mg/mL of p-NCS-Bn-DOTA was prepared in $H_2O$ and stored at −80° C. To a portion of Tmab in saline (66 μL) were added p-NCS-Bn-DOTA (49 μL) and $NaHCO_3$ buffer (274.5 μL), so that the final concentrations of Tmab and p-NCS-Bn-DOTA were 5.1 mg/mL and 0.38 mg/mL (16-fold molar excess of L), respectively. The pH of this solution was between 8 and 9 by litmus paper. The solution was rocked gently at room temperature for 17.5 h and then purified using a spin column.

Determination of Conjugate Protein Concentration by BCA Assay. The concentration of protein in macropa-Tmab and DOTA-Tmab conjugates was determined using the Pierce™ BCA Protein Assay kit (Thermo Scientific, Waltham, Mass., microplate protocol). Tmab was employed as the protein standard. A stock solution of purified Tmab was diluted with saline and the concentration of this solution (1.83 mg/mL) was determined using a NanoDrop 1000 Spectrophotometer (Thermo Scientific, Waltham, Mass.). The standard curve was linear ($r^2$=0.9966) over the concentration range measured (0-1828 μg/mL). The protein concentration of each conjugate was calculated from two independent dilutions, each measured in triplicate, and the results were averaged to give a protein concentration of 4.557 mg/mL for macropa-Tmab and 2.839 mg/mL for DOTA-Tmab.

Ligand-to-Protein Ratio Analysis by MALDI-ToF. The average number of macropa or DOTA ligands conjugated to Tmab was determined by MALDI-ToF MS/MS on a Bruker autoflex speed at the Alberta Proteomics and Mass Spectrometry Facility (University of Alberta, Canada) using a procedure described elsewhere.[108] Purified Tmab and the conjugates were analyzed in duplicate, and the $[M+H]^+$ mass signals from the chromatograms were averaged for each compound. The ligand-to-protein (L:P) ratio for each conjugate was obtained by subtracting the molecular weight of Tmab from the molecular weight of the conjugate, and subsequently dividing by the mass of the bifunctional ligand.

$^{225}$Ac Radiolabeling of Tmab Conjugates and Serum Stability of Complexes.

General. Instant thin layer chromatography paper impregnated with silica gel (iTLC-SG, Agilent Technologies, Mississauga, ON, Canada) was used to monitor the progress of . . . Ac radiolabeling reactions and to determine serum stability. TLC plates were developed as described below and then counted on a BioScan System 200 imaging scanner equipped with a BioScan Autochanger 1000 and WinScan software at least 8 h later to allow time for daughter isotopes to decay completely, ensuring that the radioactive signal measured was generated by parent $^{255}$Ac.

$^{225}$Ac Radiolabeling Studies. In a total reaction volume of 200 μL made up with $NH_4OAc$ buffer (pH 6, 0.15 M), $^{225}$Ac (10 or 20 kBq, 7-10 μL) was mixed with 25-100 μg of either macropa-Tmab (5.5-22 μL) or DOTA-Tmab (8.81-35.2 μL), and the pH was adjusted to ~5 with NaOH. A control solution was also prepared in which unmodified Tmab (25 μg) was substituted in place of conjugate. The reaction solutions were maintained at ambient temperature and analyzed at 5 min, 30 min, 1 h, 2 h, 3 h, and 4 h by spotting 8 μL in triplicate on iTLC strips. The strips were developed with a mobile phase of 0.05 M citric acid (pH 5). Under these conditions, $^{225}$Ac-macropa-Tmab and $^{225}$Ac-DOTA-Tmab remained at the baseline of the plate ($R_F$=0) and any unchelated $^{225}$Ac ($^{225}$Ac-citrate) migrated with the solvent front ($R_F$=1). Radiochemical yields (RCYs) were calculated by integrating area under the peaks on the radiochromatogram and dividing the counts associated with the $^{225}$Ac-complex ($R_F$=0) by the total counts integrated along the length of the TLC plate.

Stability of $^{225}$Ac-macropa-Tmab in Human Serum. A solution of $^{225}$Ac-macropa-Tmab was prepared using 100 μg of protein. After confirmation by TLC that a RCY of >95% had been achieved, human serum was thawed to room temperature and added to the radiolabeled immunoconjugate to give a solution containing 90% serum by volume. The sample was incubated at 37° C. At various time points over the course of 7 days, aliquots (15-30 μL) were removed from the sample and spotted in triplicate onto iTLC strips. The strips were developed using an EDTA (50 mM, pH 5.2) mobile phase and counted. Under these conditions, $^{225}$Ac-macropa-Tmab remained at the baseline ($R_F$=0) and any $^{225}$Ac ($^{225}$Ac-EDTA) that had been transchelated by serum migrated with the solvent front ($R_F$=1). Percent of complex remaining intact was calculated.

As an additional challenge, separate aliquots (39 μL) were also removed from the serum sample on days 1 and 7 and mixed with 50 mM DTPA (pH 7, 13 μL) to challenge off any $^{225}$Ac that was only loosely bound by the radioimmunoconjugate. After incubation of this solution at 37° C. for 15 minutes, an aliquot (30 μL) was spotted in triplicate on iTLC plates and developed using an EDTA (50 mM, pH 5.2) mobile phase. Percent of complex remaining intact was calculated.

In Vivo Biodistribution Studies of $[^{225}Ac(Macrona)]^+$, $[^{225}Ac(DOTA)]^-$, and $^{225}Ac(NO_3)_3$.

TABLE 1

Organ distribution of $^{225}$Ac complexes following intravenous injection in mice. Adult C57BL/6 mice were injected with $[^{225}Ac(macropa)]^+$, $[^{225}Ac(DOTA)]^-$, or $^{225}Ac(NO_3)_3$ and sacrificed after 15 min, 1 h, or 5 h. Values for each time point are given as % ID/g (n = 3) using energy window A (60-120 keV).

| Organ | 15 min | SD | 1 h | SD | 5 h | SD |
|---|---|---|---|---|---|---|
| $[^{225}Ac(macropa)]^+$ | | | | | | |
| blood | 5.11 | 2.82 | 0.40 | 0.38 | 0.01 | 0.01 |
| urine | 1378.82 | 971.53 | 489.11 | 26.75 | 12.78 | 6.10 |
| feces | 0.91 | 1.18 | 0.28 | 0.14 | 3.46 | 1.06 |
| heart | 2.19 | 0.60 | 0.31 | 0.24 | 0.10 | 0.11 |

TABLE 1-continued

Organ distribution of $^{225}$Ac complexes following intravenous injection in mice. Adult C57BL/6 mice were injected with $[^{225}Ac(macropa)]^+$, $[^{225}Ac(DOTA)]^-$, or $^{225}Ac(NO_3)_3$ and sacrificed after 15 min, 1 h, or 5 h. Values for each time point are given as % ID/g (n = 3) using energy window A (60-120 keV).

| Organ | 15 min | SD | 1 h | SD | 5 h | SD |
|---|---|---|---|---|---|---|
| liver | 2.28 | 0.41 | 0.75 | 0.18 | 0.39 | 0.03 |
| kidneys | 27.55 | 7.51 | 13.36 | 17.13 | 0.74 | 0.06 |
| lungs | 5.98 | 1.81 | 0.51 | 0.36 | 0.01 | 0.04 |
| small intestines | 2.64 | 1.08 | 1.10 | 0.47 | 0.29 | 0.20 |
| large intestines | 2.40 | 0.52 | 0.36 | 0.10 | 0.49 | 0.22 |
| brain | 0.26 | 0.09 | 0.12 | 0.07 | 0.02 | 0.02 |
| bladder | 46.74 | 24.65 | 6.23 | 7.44 | 4.25 | 5.27 |
| spleen | 2.52 | 1.08 | 0.51 | 0.19 | 0.11 | 0.03 |
| stomach | 2.97 | 0.72 | 0.41 | 0.08 | 0.01 | 0.06 |
| pancreas | 1.46 | 0.64 | 0.19 | 0.16 | 0.10 | 0.06 |
| bone (femur + joint) | 2.52 | 0.34 | 0.31 | 0.16 | 0.05 | 0.10 |
| thyroids | 28.23 | 17.90 | 3.18 | 2.21 | 0.10 | 7.95 |
| tail | 8.84 | 1.56 | 1.82 | 1.11 | 0.14 | 0.09 |
| $[^{225}Ac(DOTA)]^-$ | | | | | | |
| blood | 5.2881 | 2.9807 | 0.1144 | 0.0203 | 0.0140 | 0.0024 |
| urine | 1467.9186 | 1073.9229 | 158.6102 | 141.1945 | 1.1612 | 0.3653 |
| feces | 6.2730 | 8.7284 | 0.2035 | 0.2433 | 5.5318 | 1.7685 |
| heart | 2.3335 | 0.7337 | 0.1012 | 0.0853 | 0.0664 | 0.0091 |
| liver | 2.2520 | 0.5051 | 0.2715 | 0.1973 | 0.1010 | 0.0063 |
| kidneys | 27.6566 | 6.8974 | 1.4020 | 0.2124 | 0.6172 | 0.0168 |
| lungs | 5.7556 | 1.7234 | 0.1555 | 0.0800 | 0.0390 | 0.0135 |
| small intestines | 2.6370 | 1.3350 | 1.7207 | 2.1165 | 0.0967 | 0.0232 |
| large intestines | 2.3348 | 0.7436 | 0.1229 | 0.0551 | 0.2026 | 0.1073 |
| brain | 0.2655 | 0.0598 | 0.0224 | 0.0123 | 0.0213 | 0.0021 |
| bladder | 48.2703 | 26.4988 | 4.7351 | 4.9621 | 0.3551 | 0.0335 |
| spleen | 2.5905 | 1.3909 | 0.0938 | 0.0322 | 0.1380 | 0.0733 |
| stomach | 2.7440 | 0.8312 | 0.1367 | 0.1078 | 0.0852 | 0.0100 |
| pancreas | 1.5090 | 0.6828 | 0.0743 | 0.0752 | 0.0677 | 0.0090 |
| bone (femur + joint) | 2.6298 | 0.6802 | 0.4487 | 0.0586 | 0.2063 | 0.0231 |
| thyroids | −5.7725 | 27.0550 | 2.3564 | 2.7015 | 3.6425 | 1.8897 |
| tail | 8.8606 | 1.1879 | 0.8091 | 0.1272 | 0.3057 | 0.0766 |
| $^{225}Ac(NO_3)_3$ | | | | | | |
| blood | 40.966 | 6.455 | 20.8234 | 0.8102 | 1.9886 | 0.5457 |
| urine | 5.527 | 3.460 | 4.5194 | 0.4803 | 4.8267 | 3.6549 |
| feces | 0.240 | 0.070 | 0.2189 | 0.1167 | 0.9445 | 0.7998 |
| heart | 8.557 | 2.698 | 4.4261 | 1.2771 | 1.3450 | 0.2326 |
| liver | 22.899 | 1.788 | 39.8269 | 4.5062 | 59.8156 | 10.4928 |
| kidneys | 10.468 | 1.897 | 7.2170 | 1.5026 | 4.6910 | 2.3005 |
| lungs | 12.757 | 2.883 | 8.2412 | 1.9189 | 4.1871 | 3.8011 |
| small intestines | 2.002 | 0.094 | 1.5594 | 0.3191 | 1.3704 | 0.4345 |
| large intestines | 1.116 | 0.145 | 0.6035 | 0.4502 | 0.6479 | 0.2782 |
| brain | 0.614 | 0.283 | 0.2995 | 0.0893 | 0.0452 | 0.0343 |
| bladder | 1.477 | 0.689 | 0.9047 | 0.0759 | 1.4947 | 2.4402 |
| spleen | 22.733 | 4.962 | 34.8831 | 1.6768 | 62.9614 | 12.7041 |
| stomach | 2.348 | 0.250 | 1.6211 | 0.0147 | 2.6131 | 1.4450 |
| pancreas | 2.366 | 0.922 | 2.1771 | 0.8907 | 0.4874 | 0.4300 |
| bone (femur + joint) | 2.764 | 0.757 | 2.4707 | 0.1198 | 3.5460 | 0.6374 |
| thyroids | 4.391 | 1.511 | 2.5988 | 4.9499 | −2.7052 | 2.9758 |
| tail | 7.459 | 5.674 | 5.7939 | 1.8506 | 23.4055 | 19.5704 |

TABLE 2

Organ distribution of $^{225}Ac$ complexes following intravenous injection in mice. Adult C57BL/6 mice were injected with $[^{225}Ac(macropa)]$, $[^{225}Ac(DOTA)]^-$, or $^{225}Ac(NO_3)_3$ and sacrificed after 15 min, 1 h, or 5 h. Values for each time point are given as % ID/g (n = 3) using energy window B (180-260 keV).

| Organ | 15 min | SD | 1 h | SD | 5 h | SD |
|---|---|---|---|---|---|---|
| | | | $[^{225}Ac(macropa)]^+$ | | | |
| blood | 5.23 | 2.93 | 0.39 | 0.38 | 0.00 | 0.01 |
| urine | 1541.60 | 1105.98 | 517.19 | 11.65 | 13.51 | 6.04 |
| feces | 1.04 | 0.92 | 0.27 | 0.21 | 3.49 | 1.18 |
| heart | 2.39 | 0.80 | 0.20 | 0.31 | −0.04 | 0.12 |
| liver | 2.17 | 0.40 | 0.70 | 0.16 | 0.36 | 0.01 |
| kidneys | 27.86 | 7.39 | 12.97 | 17.16 | 0.78 | 0.14 |
| lungs | 5.83 | 1.81 | 0.54 | 0.25 | −0.05 | 0.14 |
| small intestines | 2.59 | 1.19 | 0.94 | 0.46 | 0.29 | 0.21 |
| large intestines | 2.53 | 0.57 | 0.22 | 0.18 | 0.45 | 0.27 |
| brain | 0.23 | 0.06 | 0.12 | 0.11 | −0.01 | 0.04 |
| bladder | 47.64 | 25.00 | 5.92 | 8.15 | 3.69 | 6.69 |
| spleen | 2.55 | 1.54 | 0.23 | 0.26 | 0.09 | 0.06 |
| stomach | 3.29 | 1.03 | 0.33 | 0.26 | 0.04 | 0.14 |
| pancreas | 1.63 | 0.73 | 0.12 | 0.22 | −0.12 | 0.16 |
| bone (femur + joint) | 2.69 | 0.63 | 0.17 | 0.11 | 0.02 | 0.01 |
| thyroids | −2.22 | 12.06 | 0.10 | 5.33 | −6.94 | 8.77 |
| tail | 9.39 | 1.59 | 1.82 | 1.04 | 0.13 | 0.05 |
| | | | $[^{225}Ac(DOTA)]^-$ | | | |
| blood | 5.6357 | 3.2852 | 0.1127 | 0.0403 | 0.0292 | 0.0172 |
| urine | 1635.4394 | 1233.7980 | 159.1628 | 143.0187 | 3.6967 | 3.3377 |
| feces | 1.0222 | 0.9859 | 0.2349 | 0.2923 | 3.3534 | 1.0198 |
| heart | 2.7276 | 0.7955 | 0.1378 | 0.1197 | 0.0879 | 0.0591 |
| liver | 2.1817 | 0.4921 | 0.2672 | 0.1890 | 0.2712 | 0.2370 |
| kidneys | 28.0858 | 6.9019 | 1.2560 | 0.1319 | 0.6718 | 0.1380 |
| lungs | 6.0147 | 1.8416 | 0.1946 | 0.1077 | 0.1289 | 0.0320 |
| small intestines | 2.5009 | 1.2567 | 1.8809 | 2.3424 | 0.2065 | 0.1617 |
| large intestines | 2.5365 | 0.7142 | 0.0813 | 0.0554 | 0.2527 | 0.1980 |
| brain | 0.2735 | 0.1473 | 0.0248 | 0.0120 | 0.0513 | 0.0110 |
| bladder | 54.4696 | 32.7034 | 4.7141 | 5.1077 | 0.7521 | 0.0884 |
| spleen | 2.9076 | 1.5773 | 0.0825 | 0.0965 | 0.0834 | 0.2219 |
| stomach | 2.7311 | 0.9322 | 0.1379 | 0.1390 | 0.1789 | 0.0565 |
| pancreas | 1.4929 | 1.2189 | 0.0746 | 0.0806 | 0.1266 | 0.0354 |
| bone (femur + joint) | 3.0357 | 0.7199 | 0.4126 | 0.0368 | 0.1478 | 0.1689 |
| thyroids | 1.6601 | 7.1867 | 2.6514 | 6.1376 | 16.2357 | 11.0860 |
| tail | 9.4746 | 1.5429 | 0.8973 | 0.0672 | 0.1634 | 0.0768 |
| | | | $^{225}Ac(NO_3)_3$ | | | |
| blood | 41.5628 | 6.0720 | 21.4460 | 1.0862 | 2.0018 | 0.5989 |
| urine | 5.0951 | 2.4036 | 7.0564 | 2.0984 | 3.3142 | 2.6426 |
| feces | 0.3857 | 0.1799 | 0.3300 | 0.1741 | 1.0201 | 0.9002 |
| heart | 8.3605 | 2.5149 | 4.5832 | 1.4669 | 1.3948 | 0.3318 |
| liver | 23.6091 | 2.1849 | 41.0995 | 5.1387 | 62.0765 | 10.0091 |
| kidneys | 9.6424 | 1.6131 | 6.8770 | 1.0099 | 3.8752 | 1.6179 |
| lungs | 12.9714 | 2.7540 | 8.4426 | 1.9117 | 4.3379 | 3.9596 |
| small intestines | 1.9641 | 0.1853 | 1.5192 | 0.2815 | 1.2201 | 0.3708 |
| large intestines | 1.1570 | 0.1960 | 0.5629 | 0.3460 | 0.6744 | 0.2893 |
| brain | 0.6536 | 0.2639 | 0.3247 | 0.0633 | 0.0290 | 0.0219 |
| bladder | 1.6996 | 0.7289 | 0.8092 | 0.2576 | 1.5234 | 2.6761 |
| spleen | 24.0497 | 5.3531 | 37.1540 | 0.1801 | 65.9117 | 13.1934 |
| stomach | 2.3704 | 0.3085 | 1.5867 | 0.2853 | 2.5322 | 1.4903 |
| pancreas | 2.2821 | 0.9761 | 2.1579 | 0.8408 | 0.4455 | 0.3936 |
| bone (femur + joint) | 2.7487 | 0.6608 | 2.7705 | 0.0730 | 3.8533 | 0.7991 |
| thyroids | 9.6295 | 8.0396 | 5.7426 | 3.0938 | −4.6044 | 2.5708 |
| tail | 8.0722 | 6.2766 | 6.4201 | 2.1693 | 25.4744 | 20.7518 |

TABLE 3

Organ distribution of $^{225}$Ac complexes following intravenous injection in mice. Adult C57BL/6 mice were injected with $[^{225}Ac(macropa)]^+$, $[^{225}Ac(DOTA)]^-$, or $^{225}Ac(NO_3)_3$ and sacrificed after 15 min, 1 h, or 5 h. Values for each time point are given as % ID/g (n = 3) using energy window C (400-480 keV).

| Organ | 15 min | SD | 1 h | SD | 5 h | SD |
|---|---|---|---|---|---|---|
| $[^{225}Ac(macropa)]^+$ | | | | | | |
| blood | 6.49 | 4.64 | 0.54 | 0.55 | 0.04 | 0.03 |
| urine | 2387.66 | 1987.77 | 641.63 | 49.58 | 22.27 | 8.14 |
| feces | 1.26 | 2.00 | 0.69 | 0.50 | 5.27 | 2.17 |
| heart | 2.87 | 1.51 | 0.23 | 0.97 | 0.28 | 0.84 |
| liver | 2.72 | 0.61 | 1.08 | 0.45 | 0.55 | 0.08 |
| kidneys | 33.46 | 5.62 | 17.38 | 21.12 | 1.07 | 0.37 |
| lungs | 7.55 | 3.24 | 0.84 | 0.62 | 0.15 | 0.14 |
| small intestines | 3.46 | 2.44 | 1.62 | 0.76 | 0.42 | 0.28 |
| large intestines | 3.02 | 1.11 | 0.79 | 0.51 | 0.68 | 0.17 |
| brain | 0.17 | 0.10 | 0.23 | 0.13 | −0.01 | 0.08 |
| bladder | 64.68 | 45.85 | 9.00 | 3.35 | 8.52 | 10.72 |
| spleen | 3.79 | 2.96 | 0.48 | 1.92 | 0.43 | 0.14 |
| stomach | 3.45 | 1.29 | 0.17 | 0.77 | 0.13 | 0.23 |
| pancreas | 3.00 | 2.21 | 0.43 | 1.01 | 0.13 | 0.29 |
| bone (femur + joint) | 3.74 | 1.27 | 0.70 | 0.36 | 0.08 | 0.16 |
| thyroids | −6.46 | 66.56 | 8.34 | 11.63 | 19.89 | 30.96 |
| tail | 11.75 | 0.66 | 2.57 | 1.39 | 0.28 | 0.10 |
| $[^{225}Ac(DOTA)]^-$ | | | | | | |
| blood | 7.2941 | 4.1461 | 0.1102 | 0.0707 | — | — |
| urine | 2691.0615 | 1906.4694 | 177.6788 | 168.4716 | — | — |
| feces | 1.5693 | 1.8307 | 0.4091 | 0.4652 | — | — |
| heart | 2.5579 | 2.0110 | 0.2857 | 0.2702 | — | — |
| liver | 2.9046 | 0.8757 | 0.2841 | 0.2157 | — | — |
| kidneys | 40.4489 | 10.8186 | 1.4787 | 0.7053 | — | — |
| lungs | 7.3872 | 1.9528 | 0.2551 | 0.1695 | — | — |
| small intestines | 3.8916 | 2.4605 | 2.0201 | 2.4443 | — | — |
| large intestines | 3.8419 | 1.8882 | 0.1381 | 0.2122 | — | — |
| brain | 0.1588 | 0.0692 | 0.0380 | 0.0968 | — | — |
| bladder | 76.0987 | 42.8592 | 6.9149 | 4.5152 | — | — |
| spleen | 1.5598 | 1.6847 | 0.2228 | 0.4642 | — | — |
| stomach | 3.2425 | 2.1465 | 0.1720 | 0.2911 | — | — |
| pancreas | 1.0290 | 1.1339 | 0.1730 | 0.1437 | — | — |
| bone (femur + joint) | 4.4224 | 1.8431 | 0.5654 | 0.2432 | — | — |
| thyroids | −109.5394 | 150.5455 | 3.5247 | 36.1530 | — | — |
| tail | 13.4731 | 3.2236 | 1.0280 | 0.3206 | — | — |
| $^{225}Ac(NO_3)_3$ | | | | | | |
| blood | 42.3521 | 6.5376 | 11.3736 | 15.9719 | 2.1769 | 0.7500 |
| urine | 19.8282 | 14.9210 | 104.9103 | 130.5319 | 5.8548 | 8.2799 |
| feces | 0.4896 | 0.2884 | 0.1122 | 0.1587 | 0.8535 | 0.2061 |
| heart | 9.0992 | 3.1686 | 3.3464 | 4.3204 | 1.2018 | 0.1929 |
| liver | 24.1147 | 1.8809 | 23.6180 | 33.2545 | 54.1727 | 4.7696 |
| kidneys | 14.2266 | 4.1528 | 6.2070 | 7.2061 | 4.2061 | 1.5123 |
| lungs | 14.4797 | 2.7960 | 5.2078 | 7.2810 | 5.4923 | 4.6341 |
| small intestines | 2.0956 | 0.0803 | 3.5548 | 1.8035 | 1.2922 | 0.6032 |
| large intestines | 1.5716 | 0.8096 | 0.4366 | — | 1.0259 | 0.5032 |
| brain | 0.6755 | 0.2338 | 0.4402 | 0.1057 | 0.0430 | 0.0773 |
| bladder | 1.9351 | 2.1420 | 2.2929 | 1.3941 | 3.4975 | 5.8177 |
| spleen | 25.4263 | 6.0011 | 38.1082 | — | 62.2357 | 17.5694 |
| stomach | 2.4232 | 0.3667 | 2.3350 | — | 2.0358 | 1.6514 |
| pancreas | 2.4405 | 0.5887 | 1.8508 | — | 0.4643 | 0.3109 |
| bone (femur + joint) | 3.4560 | 0.9882 | 2.7213 | — | 3.5851 | 1.4683 |

TABLE 3-continued

| Organ distribution of $^{225}Ac$ complexes following intravenous injection in mice. Adult C57BL/6 mice were injected with $[^{225}Ac(macropa)]^+$, $[^{225}Ac(DOTA)]^-$, or $^{225}Ac(NO_3)_3$ and sacrificed after 15 min, 1 h, or 5 h. Values for each time point are given as % ID/g (n = 3) using energy window C (400-480 keV). | | | | | | |
|---|---|---|---|---|---|---|
| Organ | 15 min | SD | 1 h | SD | 5 h | SD |
| thyroids | 3.5934 | 1.5023 | 0.0000 | — | −0.4455 | 3.5100 |
| tail | 9.1381 | 7.4041 | 9.0877 | — | 28.4443 | 30.7841 |

In Vivo Studies of $^{225}$Ac-Macropa-Tmab.

At the time points indicated in Table 4 below, an aliquot of complex in serum was removed and either directly analyzed by radio-TLC or first mixed with excess DTPA to remove any loosely-bound $^{225}$Ac. The decay-corrected values shown represent % activity associated with the complex at $R_F$=0 on the TLC plate after exposure to an EDTA mobile phase. Reported uncertainties (±1 SD) were derived from spotting TLC plates in triplicate at each time point. The % intact complex remaining was not significantly different for samples subjected to the DTPA challenge versus those that were not (p>0.05, 2-tail t-test). The results demonstrate that $^{225}$Ac remains strongly bound by macropa-Tmab in human serum over a 7-day period.

TABLE 4

| Complex stability (% intact complex remaining) of $^{225}$ Ac-macropa-Tmab in human serum at 37° C. | | | | |
|---|---|---|---|---|
| | 1 h | 1 day | 3 days | 7 days |
| Without DTPA Challenge | 96.4 ± 0.9 | 99.0 ± 0.5 | 98.7 ± 0.6 | 99.2 ± 0.4 |
| With DTPA Challenge | — | 91.5 ± 12 | — | 97.1 ± 1.6 |

Characterization of Eighteen-Membered Macrocyclic Ligands for Ion Chelation

Radium-223 ($^{223}$Ra) is the first therapeutic alpha (α)-emitting radionuclide to be approved for clinical use in cancer patients, and is effective in eradicating bone metastases. To harness the therapeutic potential of α-particles for soft-tissue metastases, the strategy of targeted alpha-particle therapy (TAT) has emerged, whereby lethal α-emitting radionuclides are conjugated to tumor-targeting vectors using bifunctional chelators to selectively deliver cytotoxic alpha radiation to cancer cells. Actinium-225 ($^{225}$Ac) was examined for use in TAT owing to its long 10-day half-life that is compatible with antibody-based targeting vectors and 4 high-energy α-emissions that are extremely lethal to cells. The 12-membered tetraaza macrocycle $H_4$DOTA is currently the state of the art for the chelation of the $^{225}Ac^{3+}$ ion, however, the thermodynamic stabilities of complexes of $H_4$DOTA decrease as the ionic radius of the metal ion increases, indicating that this ligand is not optimal for chelation of the of the $Ac^{3+}$ ion (the largest +3 ion on the periodic table). The macrocyclic complexes of the present technology provide a significant and unexpected improvement over known complexes, where the present examples ($H_2$macropa and $H_2$macropa-NCS; Scheme 1) illustrate the improved $^{225}$Ac bifunctional chelators according to the present technology.

Scheme 1. Structures of $H_2$macropa, $H_2$macropa-NCS ("macropa-NCS"), and macropa-$(OCH_2CH_2)$-Ph-NCS.

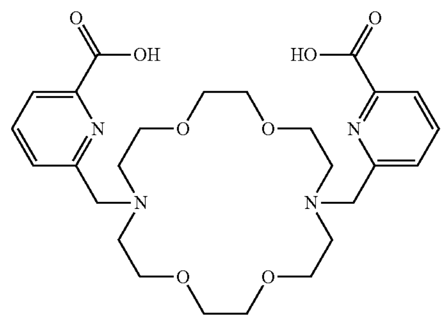

$H_2$macropa

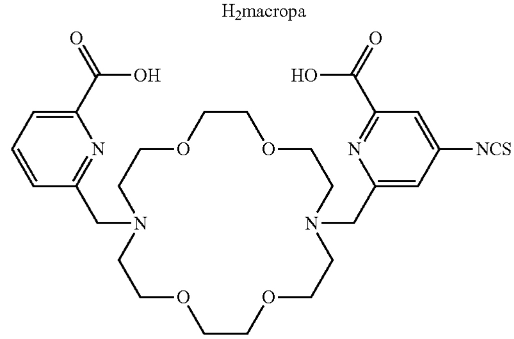

macropa-NCS

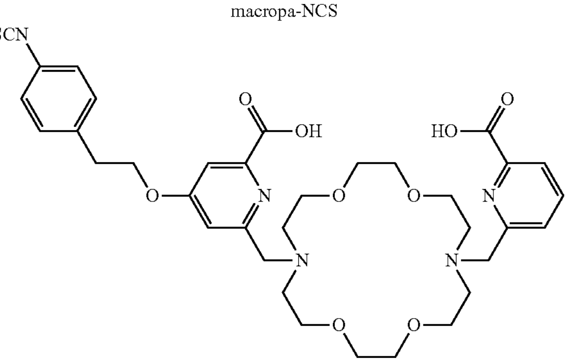

macropa-$(OCH_2CH_2)$—Ph-NCS

Previous studies have shown that macropa, for which the thermodynamic affinity for the whole lanthanide series was evaluated, is selective for the larger metal ions $La^{3+}$, $Pb^{2+}$, and $Am^{3+}$ over the smaller $Lu^{3+}$, $Ca^{2+}$, and $Cm^{3+}$ ions.[24-26] Without wishing to be bound by theory it was believed that macropa would effectively chelate the large $Ac^{3+}$ ion. Before assessing its Ac-chelation properties, complex formation was evaluated in situ between macropa and cold $La^{3+}$ and $Lu^{3+}$ ions. In these studies, $La^{3+}$ was used as a non-radioactive surrogate for $^{225}Ac^{3+}$ because it is chemically similar albeit slightly smaller (1.03 Å, CN 6). Complexation of the smaller $Lu^{3+}$ ion (0.861 Å, CN 6) by macropa was investigated to probe its size-selectivity. $La^{3+}$ and $Lu^{3+}$ titrations confirmed the high affinity of these metal ions for macropa at pH 7.4, consistent with the previously measured stability constants (log $K_{LaL}$=14.99, log $K_{LuL}$=8.25).[24] The kinetic inertness of these complexes formed in situ was investigated by challenging them with an excess of either ethylenediaminetetraacetic acid (EDTA) or diethylenetriaminepentaacetic acid (DTPA) chelators that have a higher thermodynamic affinity than macropa for $Lu^{3+}$ and $La^{3+}$ ions.[27] The $Lu^{3+}$ ion was transchelated within 1 min upon the addition of only 10 equiv of EDTA, whereas the $La^{3+}$ complex remained intact for up to 21 days in the presence of 1000 equiv of DTPA. These results demonstrate that, despite a strong thermodynamic preference for DTPA to transchelate $La^{3+}$, the high level of kinetic inertness of the macropa complex inhibits this process on a detectable time scale.

The $La^{3+}$ and $Lu^{3+}$ complexes of macropa were isolated and their solid-state structures were elucidated by X-ray crystallography (FIGS. 1A-1D). The $La^{3+}$ and $Lu^{3+}$ ions reside above the 18-membered macrocycle, and the two picolinate arms are positioned on the same side of the macrocycle. The coordination sphere of the $Lu^{3+}$ ion is satisfied by the ten donors of macropa with both picolinate arms deprotonated; by contrast, the larger $La^{3+}$ ion forms an 11-coordinate complex by the incorporation of an inner-sphere water molecule that penetrates the macrocycle. The ability of macropa to form stable 11-coordinate complexes is of particular significance because recent EXAFS studies have demonstrated that $Ac^{3+}$ prefers a coordination number of 11 in aqueous solutions.[29,30]

Macropa was examined for the chelation of the larger, radioactive $^{225}Ac^{3+}$ ion and compared to DOTA. Both ligands (59 μM) were incubated with $^{225}Ac$ (26 kBq) in 0.15 M $NH_4OAc$ buffer at pH 5.5-6, and the complexation reaction was monitored by radio-TLC after 5 min. Remarkably, macropa complexed all the $^{225}Ac$ after merely 5 min at RT, whereas DOTA only complexed 10% under these conditions. At 100-fold lower concentration (0.59 μM) of macropa, a L:M ratio of only 1800, radiolabeling was still complete at RT in 5 min. At this concentration, DOTA failed to form a complex with $^{225}Ac$. Taken together, these studies reveal macropa to exhibit excellent radiolabeling kinetics at ambient temperature and submicromolar ligand concentration, conditions under which DOTA fails.

The long half-life of $^{225}Ac$ necessitates its stable complex retention in vivo to avoid off-target damage to normal tissues arising from the release of free $^{225}Ac^{3+}$. Furthermore, the stability of $^{225}Ac$ complexes against transmetalation and transchelation needs to be high. To determine the kinetic inertness, $[^{225}Ac(macropa)]^+$ was challenged with $La^{3+}$ because of the established high affinity of macropa for this metal ion. A 50-fold excess of $La^{3+}$ with respect to ligand concentration was added to $^{225}Ac$-radiolabeled solutions of macropa (0.59 μM) at RT. Over 7 days, 98% of the $^{225}Ac$ complex remained intact by radio-TLC, signifying that a large molar equivalent of $La^{3+}$ is unable to displace $^{225}Ac^{3+}$. The stability of $[^{225}Ac(macropa)]^+$ in human serum was also evaluated by radio-TLC and revealed that $^{225}Ac^{3+}$ remains complexed by macropa for at least 8 days.

Evaluation of the Biodistribution of $[^{225}Ac(Macropa)]^+$ Complexes

Figure 2A:
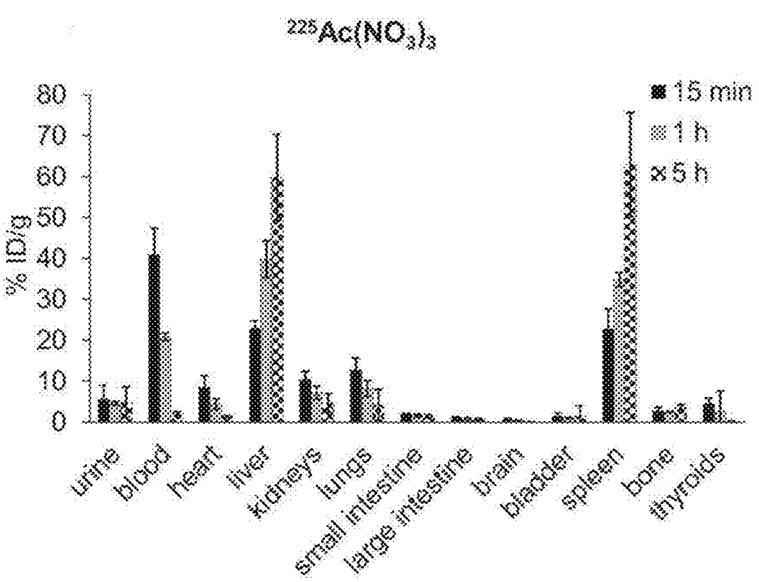
Figure 2B:
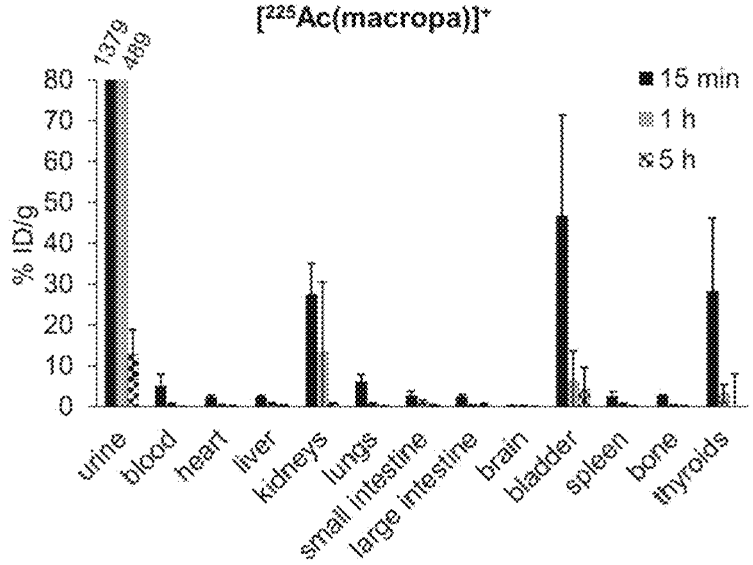
FIG. 2B, top view).
Figure 2C:
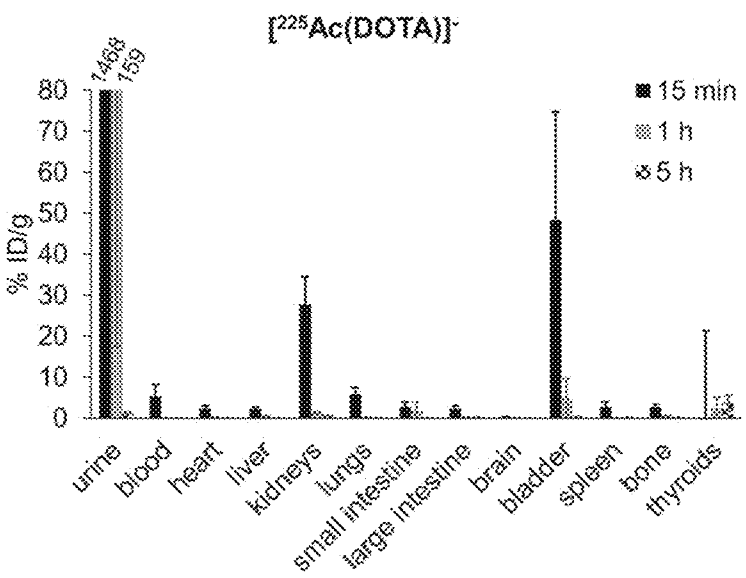

The in vivo stability $[^{225}Ac(macropa)]^+$ was examined by comparing its biodistribution to those of $^{225}Ac(NO_3)_3$ and $[^{225}Ac(DOTA)]^-$. C57BL/6 mice were injected via tail vein with 10-50 kBq of each radiometal complex and were sacrificed after 15 min, 1 h, or 5 h. The amount of $^{225}Ac$ retained in each organ was quantified by gamma counting and reported as the percent of injected dose per gram of tissue (% ID/g). The results of these studies are compiled in Tables 1-3. Inadequate stability of an $^{225}Ac$ complex leading to the loss of radioisotope in vivo is manifested by the accumulation of $^{225}Ac$ in the liver, spleen, and bone of mice.[11,12,32] FIG. 2A demonstrates slow blood clearance and excretion, coupled to large accumulation in the liver and spleen of the uncomplexed $^{225}Ac(NO_3)_3$. The biodistribution profile of $[^{225}Ac(macropa)]^+$ (FIG. 3B) differs markedly from that of $^{225}Ac(NO_3)_3$. $[^{225}Ac(macropa)]^+$ was rapidly cleared from mice, with very little activity measured in blood by 1 h post injection. Most of the injected dose was renally excreted and subsequently detected in the urine, demonstrating the moderate kidney and bladder uptake of $[^{225}Ac(macropa)]^+$ observed in mice at 15 min and 1 h post injection. Of significance, $[^{225}Ac(macropa)]^+$ did not accumulate in any organ over the time course of the study, indicating that the complex does not release free $^{225}Ac^{3+}$ in vivo. Its biodistribution profile was similar to that of $[^{225}Ac(DOTA)]^-$ (FIG. 3C), which has been previously shown to retain $^{225}Ac^{3+}$ in vivo.[7]

Synthesis and Characterization of $[^{225}Ac(Macropa)]^+$ TAT Complexes

Due to the inherent stability of the $[^{225}Ac(macropa)]^+$ complexes, macropa was incorporated into tumor-targeting constructs. To facilitate its conjugation, a reactive isothiocyanate functional group was installed onto one of the picolinate arms of macropa to give the novel bifunctional ligand macropa-NCS (Scheme 1). As illustrated in vide supra, macropa-NCS was synthesized over 8 steps and characterized by conventional techniques. For one tumor-targeting construct, macropa-NCS was s conjugated to trastuzumab (Tmab), an FDA-approved monoclonal antibody that targets the human epidermal growth factor receptor 2 (HER2) in breast and other cancers.[33] With a biological half-life of several weeks,[34,35] Tmab is an ideal vector to shuttle the long-lived $^{225}Ac$ radionuclide to tumor cells. $^{225}Ac$-macropa-Tmab displayed excellent stability in human serum at 37° C.; after 7 days, >99% of the complex remained intact (Table 4). Together, these results highlight the efficacy of macropa as a chelator for $^{225}Ac$ in antibody constructs as well as other cancer-targeted constructs.

REFERENCES

7. M. R. McDevitt, D. Ma, L. T. Lai, J. Simon, P. Borchardt, R. K. Frank, K. Wu, V. Pellegrini, M. J. Curcio, M. Miederer, et al., *Science* 2001, 294, 1537.
11. I. A. Davis, K. A. Glowienka, R. A. Boll, K. A. Deal, M. W. Brechbiel, M. Stabin, P. N. Bochsler, S. Mirzadeh, S. J. Kennel, *Nucl. Med. Biol.* 1999, 26, 581.
12. K. A. Deal, I. A. Davis, S. Mirzadeh, S. J. Kennel, M. W. Brechbiel, *J. Med. Chem.* 1999, 42, 2988.
24. A. Roca-Sabio, M. Mato-Iglesias, D. Esteban-Gómez, É. Tóth, A. de Blas, C. Platas-Iglesias, T. Rodriguez-Blas, *J. Am. Chem. Soc.* 2009, 131, 3331.
25. R. Ferreirós-Martinez, D. Esteban-Gómez, É. Tóth, A. de Blas, C. Platas-Iglesias, T. Rodríguez-Blas, *Inorg. Chem.* 2011, 50, 3772.
26. M. P. Jensen, R. Chiarizia, I. A. Shkrob, J. S. Ulicki, B. D. Spindler, D. J. Murphy, M. Hossain, A. Roca-Sabio, C. Platas-Iglesias, A. de Blas, et al., *Inorg. Chem.* 2014, 53, 6003.
27. A. E. Martell, R. M. Smith, *Critical Stability Constants: Vol.* 1, Plenum Press, New York; London, 1974.

29. M. G. Ferrier, E. R. Batista, J. M. Berg, E. R. Birnbaum, J. N. Cross, J. W. Engle, H. S. La Pierre, S. A. Kozimor, J. S. Lezama Pacheco, B. W. Stein, et al., *Nat. Commun.* 2016, 7, 12312.

30. M. G. Ferrier, B. W. Stein, E. R. Batista, J. M. Berg, E. R. Birnbaum, J. W. Engle, K. D. John, S. A. Kozimor, J. S. Lezama Pacheco, L. N. Redman, *ACS Cent. Sci.* 2017, 3, 176.

32. G. J. Beyer, R. Bergmann, K. Schomäcker, F. Rösch, G. Schäfer, E. V Kulikov, A. F. Novgorodov, *Isot. Isot. Environ. Heal. Stud* 1990, 26, 111.

33. M. M. Moasser, *Oncogene* 2007, 26, 6469.

34. B. Leyland-Jones, K. Gelmon, J.-P. Ayoub, A. Arnold, S. Verma, R. Dias, P. Ghahramani, *J. Clin. Oncol.* 2003, 21, 3965.

35. D. Leveque, L. Gigou, J. P. Bergerat, *Curr. Clin. Pharmacol.* 2008, 3, 51.

37. A. P. Kozikowski, F. Nan, P. Conti, J. Zhang, E. Ramadan, T. Bzdega, B. Wroblewska, J. H. Neale, S. Pshenichkin, J. T. Wroblewski, *J. Med Chem.* 2001, 44, 298.

38. K. P. Maresca, S. M. Hillier, F. J. Femia, D. Keith, C. Barone, J. L. Joyal, C. N. Zimmerman, A. P. Kozikowski, J. A. Barrett, W. C. Eckelman, et al., *J. Med Chem.* 2009, 52, 347.

39. S. M. Hillier, K. P. Maresca, F. J. Femia, J. C. Marquis, C. A. Foss, N. Nguyen, C. N. Zimmerman, J. A. Barrett, W. C. Eckelman, M. G. Pomper, et al., *Cancer Res.* 2009, 69, 6932.

40. J. A. Barrett, R. E. Coleman, S. J. Goldsmith, S. Vallabhajosula, N. A. Petry, S. Cho, T. Armor, J. B. Stubbs, K. P. Maresca, M. G. Stabin, et al., *J. Nucl. Med* 2013, 54, 380.

41. J. Kelly, A. Amor-Coarasa, A. Nikolopoulou, D. Kim, C. Williams Jr., S. Ponnala, J. W. Babich, *Eur. J. Nucl. Med Mol. Imaging* 2017, 44, 647.

42. A. Ghosh, W. D. W. Heston, *J. Cell. Biochem.* 2004, 91, 528.

43. M. S. Dennis, M. Zhang, Y. Gloria Meng, M. Kadkhodayan, D. Kirchhofer, D. Combs, L. A. Damico, *J. Biol. Chem.* 2002, 277, 35035.

44. C. E. Dumelin, S. Trüssel, F. Buller, E. Trachsel, F. Bootz, Y. Zhang, L. Mannocci, S. C. Beck, M. Drumea-Mirancea, M. W. Seeliger, et al., *Angew. Chem. Int. Ed.* 2008, 47, 3196.

102. M. Mato-Iglesias, A. Roca-Sabio, Z. Pálinkás, D. Esteban-Gómez, C. Platas-Iglesias, É. Tóth, A. de Blas, T. Rodríguez-Blas, *Inorg. Chem.* 2008, 47, 7840-7851.

103. A. Roca-Sabio, M. Mato-Iglesias, D. Esteban-Gómez, É. Tóth, A. de Blas, C. Platas-Iglesias, T. Rodriguez-Blas, *J. Am. Chem. Soc.* 2009, 131, 3331-3341.

104. V. J. Gatto, G. W. Gokel, *J. Am. Chem. Soc.* 1984, 106, 8240-8244.

105. E. R. Neil, M. A. Fox, R. Pal, L.-O. Palsson, B. A. O'Sullivan, D. Parker, *Dalton Trans.* 2015, 44, 14937-14951.

106. Z. E. A. Chamas, X. Guo, J.-L. Canet, A. Gautier, D. Boyer, R. Mahiou, *Dalton Trans.* 2010, 39, 7091-7097.

108. D. T. Corson, C. F. Meares, *Bioconjug. Chem.* 2000, 11, 292-299.

109. G. M. Sheldrick, *Acta Crystallogr*. Sect. A 2015, 71, 3-8.

110. G. M. Sheldrick, *Acta Crystallogr*. Sect. A 2008, 64, 112-122.

111. P. Múller, *Crystallogr. Rev.* 2009, 15, 57-83.

112. O. V Dolomanov, L. J. Bourhis, R. J. Gildea, J. A. K. Howard, H. Puschmann, *J. Appl. Crystallogr.* 2009, 42, 339-341.

113. J. Dilling, R. Krucken, L. Merminga, Eds., *ISAC and ARIEL: The TRIUMF Radioactive Beam Facilities and the Scientific Program*, Springer, Dordrecht, Netherlands, 2014.

114. J. R. Crawford, P. Kunz, H. Yang, P. Schaffer, T. J. Ruth, *Appl. Radiat. Isot.* 2017, 122, 222-228.

115. B. Zielinska, C. Apostolidis, F. Bruchertseifer, A. Morgenstern, *Solvent Extr. Ion Exch.* 2007, 25, 339-349.

116. V. Radchenko, J. W. Engle, J. J. Wilson, J. R. Maassen, F. M. Nortier, W. A. Taylor, E. R. Birnbaum, L. A. Hudston, K. D. John, M. E. Fassbender, *J. Chromatogr. A* 2015, 1380, 55-63.

117. M. P. Miranda-Hernandez, E. R. Valle-Gonzälez, D. Ferreira-Gömez, N. O. Përez, L. F. Flores-Ortiz, E. Medina-Rivero, *Anal. Bioanal. Chem.* 2016, 408, 1523-1530.

118. E. W. Price, K. J. Edwards, K. E. Carnazza, S. D. Carlin, B. M. Zeglis, M. J. Adam, C. Orvig, J. S. Lewis, *Nucl. Med. Biol.* 2016, 43, 566-576.

119. J. Kelly, A. Amor-Coarasa, A. Nikolopoulou, D. Kim, C. Williams, S. Ponnala, J. W. Babich, *Eur. J. Nucl. Med. Mol. Imaging* 2017, 44, 647-661.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I (I)

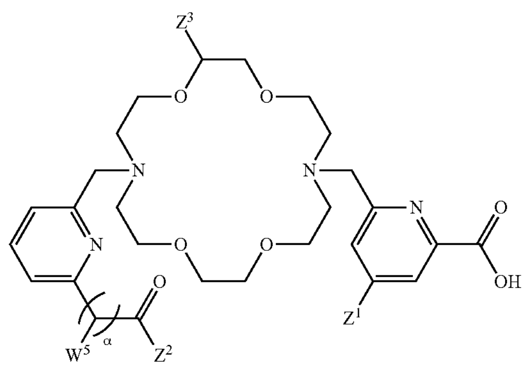

or a pharmaceutically acceptable salt thereof, wherein $Z^1$ is H or —$X^1$—$W^2$;

$Z^2$ is OH or NH—$W^3$;

$Z^3$ is H or $W^7$;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2R'$, —$SO_2(OR')$, —$SO_2NR'_2$, —P(O)$(OR')_2$, —P(O)R'(OR'), —P(O)$R'_2$, —CN, —OCN, —SCN, —NCO, —NCS, —NR'—$NH_2$, —N═C═N—R', —$SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)y_x$-R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2R'$, —$SO_2(OR')$, —$SO_2NR'_2$, —P(O)$(OR')_2$, —P(O)R'(OR'), —P(O)$R'_2$, —CN, —OCN, —SCN, —NCO, —NCS, —NR'—$NH_2$, —N═C═N—R', —$SO_2Cl$, —C(O)Cl, or an epoxide group; and R' is independently at each occurrence H, halo, —$N_3$, $C_1$-$C_6$ alkyl, $C_3$-$C_6$ cycloalkyl, $C_2$-$C_6$ alkenyl, $C_5$-$C_8$cycloalkenyl, $C_2$-$C_6$ alkynyl, $C_5$-$C_{10}$ cycloalkynyl, $C_5$-$C_6$ aryl, heterocyclyl, or heteroaryl.

B. The compound of Paragraph A, wherein the compound is of Formula III (III)

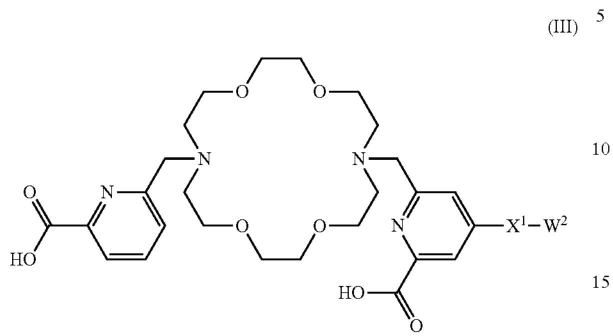

or a pharmaceutically acceptable salt thereof.

C. The compound of Paragraph A or Paragraph B, wherein the compound is

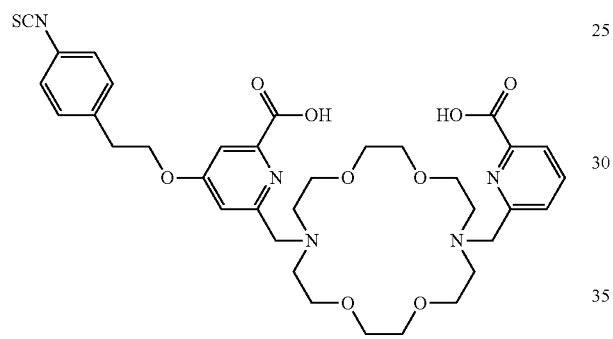

or pharmaceutically acceptable salt thereof.

D. The compound of Paragraph A, wherein the compound of Formula I is of Formula VI (VI)

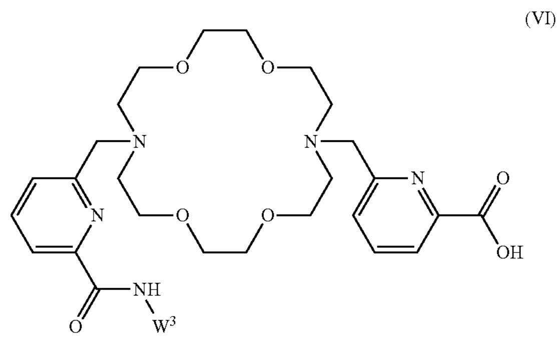

or a pharmaceutically acceptable salt thereof.

E. The compound of Paragraph A, wherein the compound of Formula I is of Formula IX (IX)

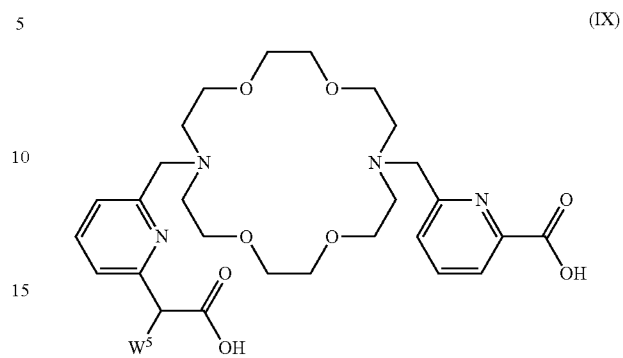

or a pharmaceutically acceptable salt thereof.

F. The compound of Paragraph A, wherein the compound of Formula I is of Formula XII (XII)

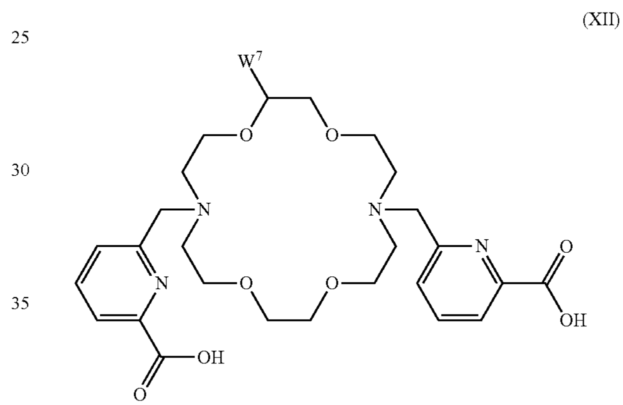

or a pharmaceutically acceptable salt thereof.

G. A compound of Formula IA (IA)

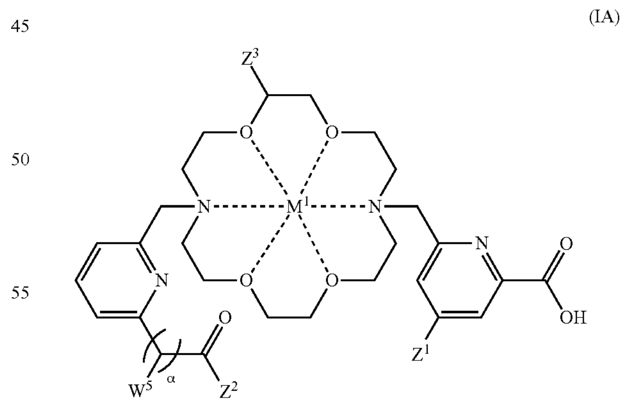

or a pharmaceutically acceptable salt thereof, wherein
$M^1$ is an alpha-emitting radionuclide;
$Z^1$ is H or —$X^1$—$W^2$;
$Z^2$ is OH or NH—$W^3$;
$Z^3$ is H or $W^7$;
α is 0 or 1;
$X^1$ is O, NH, or S;

$W^2$ and $W^3$ are each independently H, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)_y—R'$ where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)y_x$-R' where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group; and R' is independently at each occurrence H, halo, $—N_3$, $C_1$-$C_6$ alkyl, $C_3$-$C_6$ cycloalkyl, $C_2$-$C_6$ alkenyl, $C_5$-$C_8$cycloalkenyl, $C_2$-$C_6$ alkynyl, $C_8$-$C_{10}$ cycloalkynyl, $C_5$-$C_6$ aryl, heterocyclyl, or heteroaryl.

H. The compound of Paragraph G, wherein $M^1$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

I. The compound of Paragraph G or Paragraph H, wherein the compound of Formula I is of Formula IV (IV)

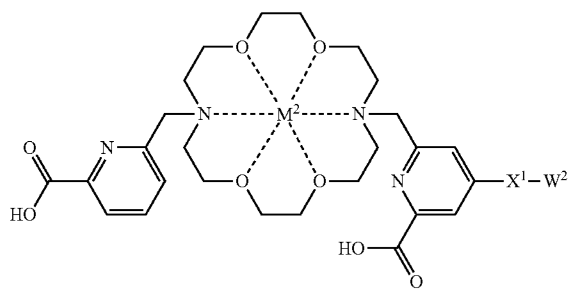

or a pharmaceutically acceptable salt thereof, wherein $M^2$ is an alpha-emitting radionuclide.

J. The compound of Paragraph I, wherein $M^2$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

K. The compound of Paragraph I, wherein the compound is

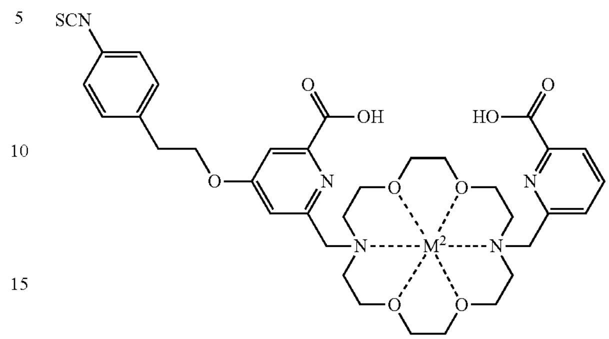

or a pharmaceutically acceptable salt thereof.

L. The compound of Paragraph K, wherein $M^2$ is actinium-225 ($^{221}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

M. The compound of Paragraph G or Paragraph H, wherein the compound of Formula IA is of Formula VIII (VII)

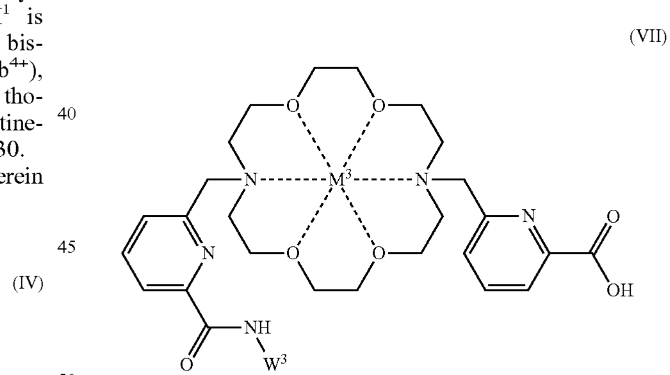

or a pharmaceutically acceptable salt thereof, wherein $M^3$ is an alpha-emitting radionuclide.

N. The compound of Paragraph M, wherein $M^3$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

O. The compound of Paragraph G or Paragraph H, wherein the compound of Formula IA is of Formula X (X)

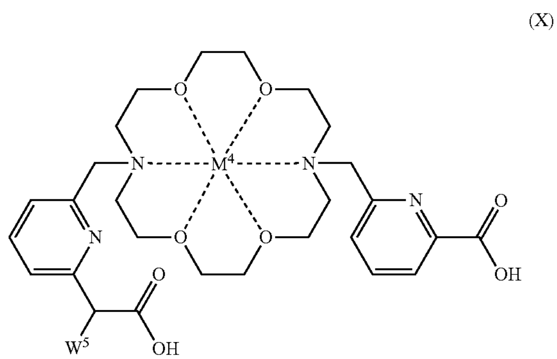

or a pharmaceutically acceptable salt thereof, wherein $M^4$ is an alpha-emitting radionuclide.

P. The compound of Paragraph O, wherein $M^4$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

Q. The compound of Paragraph G or Paragraph H, wherein the compound of Formula IA is of Formula XIII (XIII)

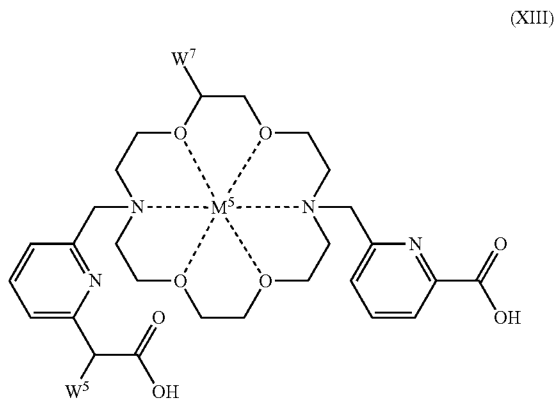

or a pharmaceutically acceptable salt thereof, wherein $M^5$ is an alpha-emitting radionuclide.

R. The compound of Paragraph Q, wherein $M^5$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

S. A targeting compound of Formula II (II)

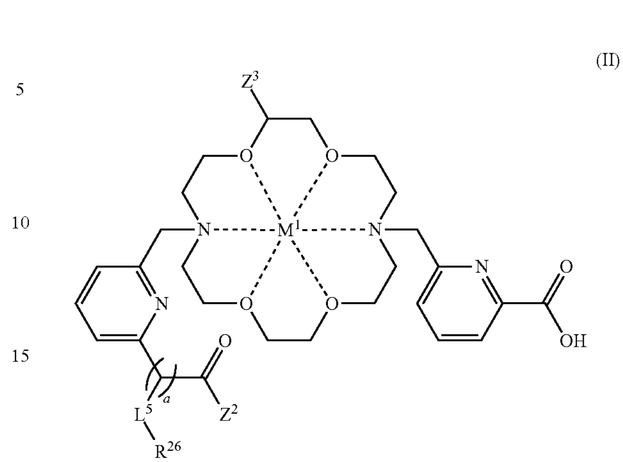

or a pharmaceutically acceptable salt thereof, wherein $M^1$ is an alpha-emitting radionuclide;

$Z^1$ is H or $-L^3-R^{22}$;

$Z^2$ is OH or $NH-L^4-R^{24}$;

$Z^3$ is H or $-L^6-R^{28}$.

α is 0 or 1;

$X^1$ is O, NH, or S;

$L^3$, $L^4$, $L^5$, and $L^6$ are independently at each occurrence a bond or a linker group; and $R^{22}$, $R^{24}$, $R^{26}$, and $R^{28}$ each independently comprises an antibody, antibody fragment (e.g., an antigen-binding fragment), a binding moiety, a binding peptide, a binding polypeptide (such as a selective targeting oligopeptide containing up to 50 amino acids), a binding protein, an enzyme, a nucleobase-containing moiety (such as an oligonucleotide, DNA or RNA vector, or aptamer), or a lectin.

T. The targeting compound of Paragraph S, wherein $M^1$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

U. The targeting compound of Paragraph S or Paragraph T, wherein $R^{22}$, $R^{24}$, $R^{26}$, and $R^{28}$ each independently comprise belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, Etaracizumab, an antigen-binding fragment of any thereof, a prostate specific membrane antigen ("PSMA") binding peptide, a somatostatin receptor agonist, a bombesin receptor agonist, a seprase binding compound, or a binding fragment of any thereof.

V. The targeting compound of any one of Paragraphs S-U, wherein the targeting compound of Formula II is of Formula V (V)

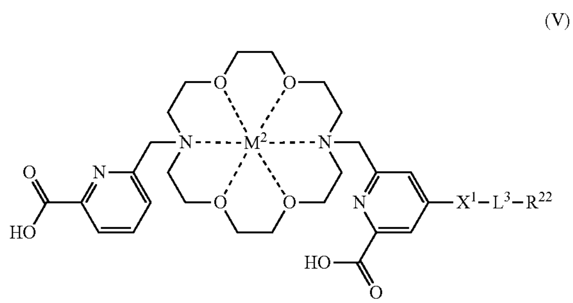

or a pharmaceutically acceptable salt thereof, wherein $M^2$ is an alpha-emitting radionuclide.

W. The targeting compound of Paragraph V, wherein $M^2$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

X. The targeting compound of any one of Paragraphs S-U, wherein the targeting compound of Formula II is of Formula VIII (VIII)

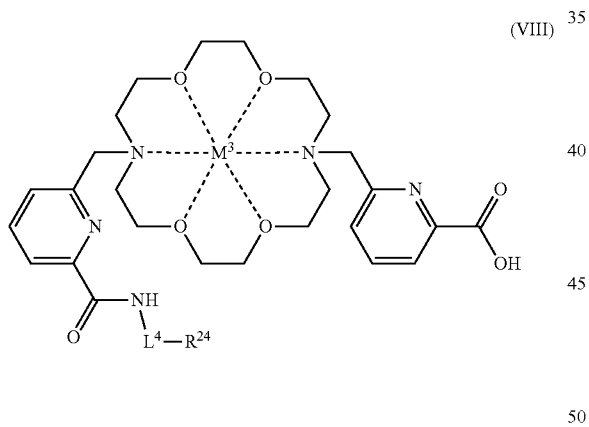

or a pharmaceutically acceptable salt thereof, wherein $M^3$ is an alpha-emitting radionuclide.

Y. The targeting compound of Paragraph X, wherein $M^3$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

Z. The targeting compound of any one of Paragraphs S-U, wherein the targeting compound of Formula II is of Formula XI (XI)

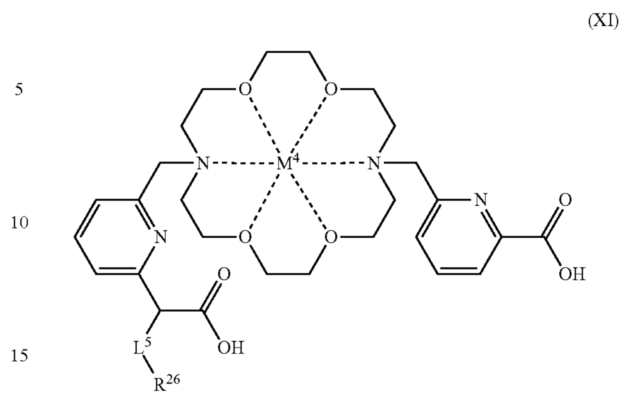

or a pharmaceutically acceptable salt thereof, wherein $M^4$ an alpha-emitting radionuclide.

AA. The targeting compound of Paragraph Z, wherein $M^4$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AB. The targeting compound of any one of Paragraphs S-U, wherein the targeting compound of Formula II is of Formula XIV (XIV)

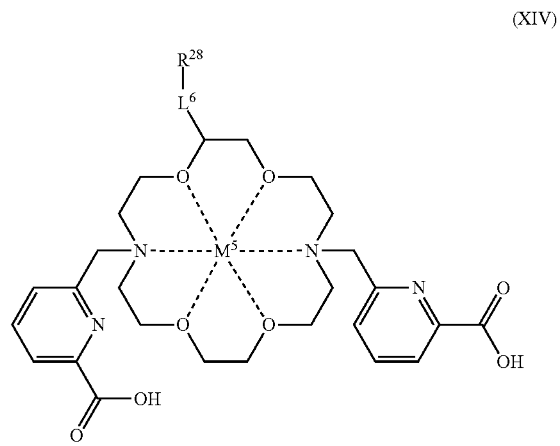

or a pharmaceutically acceptable salt thereof, wherein $M^5$ is an alpha-emitting radionuclide.

AC. The targeting compound of Paragraph AB, wherein $M^5$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AD. A modified antibody, modified antibody fragment, or modified binding peptide comprising a linkage arising from conjugation of a compound of Formula I (I)

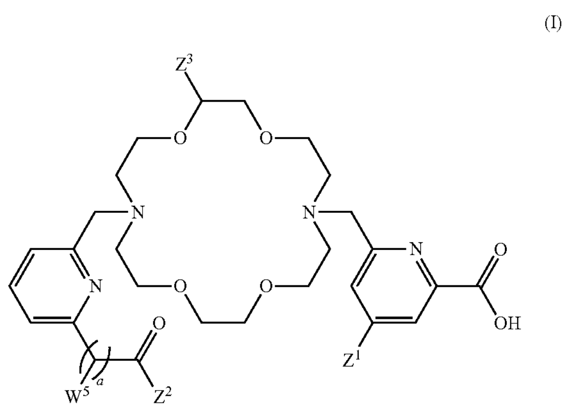

or pharmaceutically acceptable salt thereof, with an antibody, antibody fragment, or binding peptide, wherein $Z^1$ is H or —$X^1$—$W^2$;

$Z^2$ is OH or NH—$W^3$;

$Z^3$ is H or $W^7$;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)_y—R'$ where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)y_x$-R' where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group; and R' is independently at each occurrence H, halo, $—N_3$, $C_1$-$C_6$ alkyl, $C_3$-$C_6$ cycloalkyl, $C_2$-$C_6$ alkenyl, $C_5$-$C_8$cycloalkenyl, $C_2$-$C_6$ alkynyl, $C_5$-$C_{10}$ cycloalkynyl, $C_5$-$C_6$ aryl, heterocyclyl, or heteroaryl.

AE. The modified antibody, modified antibody fragment, or modified binding peptide of Paragraph AD, wherein the antibody comprises belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

AF. The modified antibody, modified antibody fragment, or modified binding peptide of Paragraph AD or Paragraph AE, wherein the antibody fragment comprises an antigen-binding fragment of belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

AG. The modified antibody, modified antibody fragment, or modified binding peptide of any one of Paragraphs AD-AF, wherein the binding peptide comprises a prostate specific membrane antigen ("PSMA") binding peptide, a somatostatin receptor agonist, a bombesin receptor agonist, a seprase binding compound, or a binding fragment thereof.

AH. The modified antibody, modified antibody fragment, or modified binding peptide of any one of Paragraphs AD-AG, wherein the compound of Formula I is of Formula III (III)

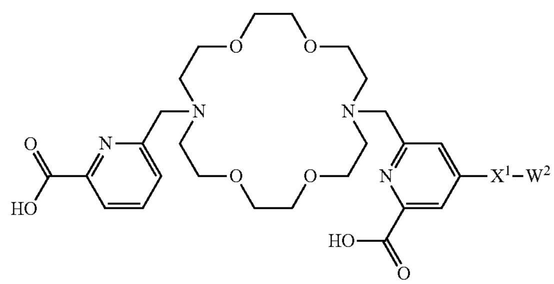

or a pharmaceutically acceptable salt thereof.

AI. The modified antibody, modified antibody fragment, or modified binding peptide of any one of Paragraphs AD-AH, wherein the linkage is a thiocyanate linkage; wherein the thiocyanate linkage arises from conjugation of the compound with the antibody, antibody fragment, or binding peptide; and wherein the compound is

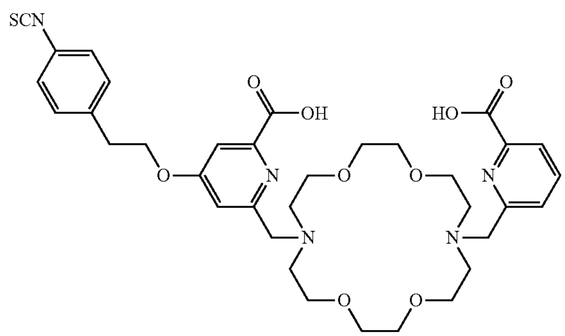

or pharmaceutically acceptable salt thereof.

AJ. The modified antibody, modified antibody fragment, or modified binding peptide of any one of Paragraphs AD-AG, wherein the compound of Formula I is of Formula VI (VI)

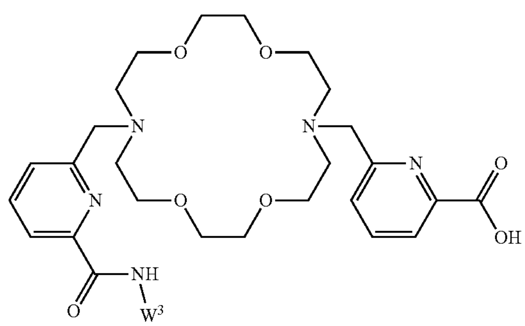

or a pharmaceutically acceptable salt thereof.

AK. The modified antibody, modified antibody fragment, or modified binding peptide of any one of Paragraphs AD-AG, wherein the compound of Formula I is of Formula IX (IX)

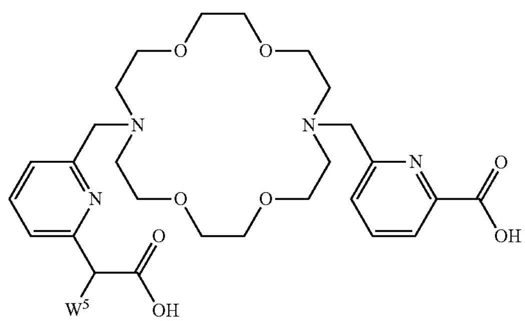

or a pharmaceutically acceptable salt thereof.

AL. The modified antibody, modified antibody fragment, or modified binding peptide of any one of Paragraphs AD-AG, wherein the compound of Formula I is of Formula XII (XII)

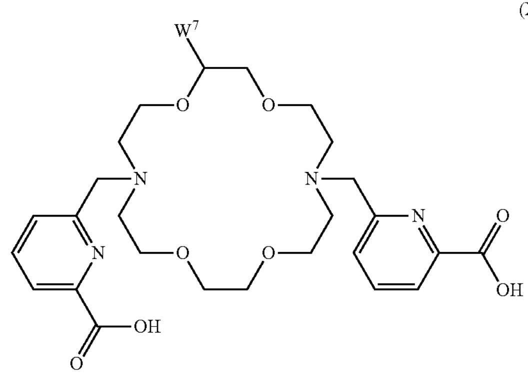

or a pharmaceutically acceptable salt thereof.

AM. A modified antibody, modified antibody fragment, or modified binding peptide comprising a linkage arising from conjugation of a compound of Formula IA (IA)

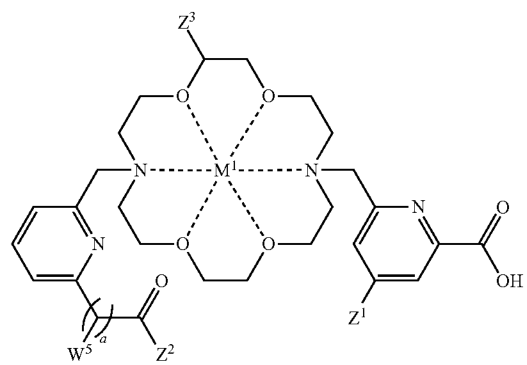

or a pharmaceutically acceptable salt thereof, with an antibody, antibody fragment, or binding peptide, wherein $M^1$ is an alpha-emitting radionuclide;

$Z^1$ is H or —$X^1$—$W^2$;

$Z^2$ is OH or NH—$W^3$;

$Z^3$ is H or $W^7$;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)_y$—R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2$R', —$SO_2$(OR'), —$SO_2$NR'$_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2$Cl, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, —$CH_2CH_2$—$(OCH_2CH_2)_w$—R' where w is 1, 2, 3, 4, 5, 6, 7, 8, 9, or 10, or —$CH_2CH_2$—$(OCH_2CH_2)_x$—OR' where x is 1, 2, 3, 4, 5, 6, 7, 8, 9, or 10, each of which may optionally be substituted with one or more of halo, —$N_3$, —OR', —$CH_2CH_2$—$(OCH_2CH_2)y_x$-R' where y is 1, 2, 3, 4, 5, 6, 7, 8, 9, or 10, —$CH_2CH_2$—$(OCH_2CH_2)_z$—OR' where z is 1, 2, 3, 4, 5, 6, 7, 8, 9, or 10, —SR', —OC(O)R', —C(O)OR', —C(S)OR', —S(O)R', —$SO_2$R', —$SO_2$(OR'), —$SO_2NR'_2$, —P(O)(OR')$_2$, —P(O)R'(OR'), —P(O)R'$_2$, —CN, —OCN, —SCN, —NCO, —NCS, —NR'—$NH_2$, —N═C═N—R', —$SO_2$Cl, —C(O)Cl, or an epoxide group; and R' is independently at each occurrence H, halo, —$N_3$, $C_1$-$C_6$ alkyl, $C_3$-$C_6$ cycloalkyl, $C_2$-$C_6$ alkenyl, $C_5$-$C_8$cycloalkenyl, $C_2$-$C_6$ alkynyl, $C_5$-$C_{10}$ cycloalkynyl, $C_5$-$C_6$ aryl, heterocyclyl, or heteroaryl.

AN. The modified antibody, modified antibody fragment, or modified binding peptide of Paragraph AM, wherein $M^1$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AO. The modified antibody, modified antibody fragment, or modified binding peptide of Paragraph AM or Paragraph AN, wherein the antibody comprises belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

AP. The modified antibody, modified antibody fragment, or modified binding peptide of any one of Paragraphs AM-AO, wherein the antibody fragment comprises an antigen-binding fragment of belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

AQ. The modified antibody, modified antibody fragment, or modified binding peptide of any one of Paragraphs AM-AP, wherein the binding peptide comprises a prostate specific membrane antigen ("PSMA") binding peptide, a somatostatin receptor agonist, a bombesin receptor agonist, a seprase binding compound, or a binding fragment thereof.

AR. The modified antibody, modified antibody fragment, or modified binding peptide of any one of Paragraphs AM-AQ, wherein the compound of Formula I is of Formula IV (IV)

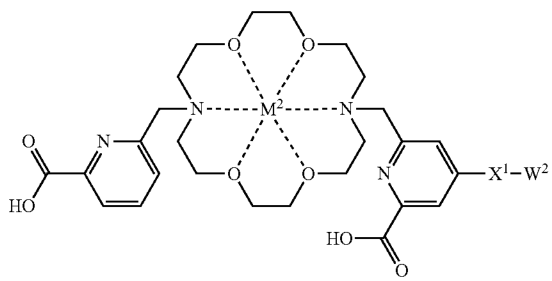

or a pharmaceutically acceptable salt thereof, wherein $M^2$ is an alpha-emitting radionuclide.

AS. The modified antibody, modified antibody fragment, or modified binding peptide of Paragraph AR, wherein $M^2$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AT. The modified antibody, modified antibody fragment, or modified binding peptide of Paragraph AR, wherein the linkage is a thiocyanate linkage; wherein the thiocyanate linkage arises from conjugation of the compound with the antibody, antibody fragment, or binding peptide; and wherein the compound is

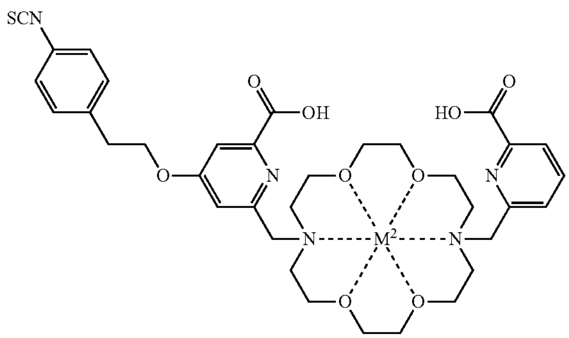

or a pharmaceutically acceptable salt thereof.

AU. The modified antibody, modified antibody fragment, or modified binding peptide of Paragraph AT, wherein $M^2$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AV. The modified antibody, modified antibody fragment, or modified binding peptide of any one of Paragraphs AM-AQ, wherein the compound of Formula IA is of Formula VIII (VII)

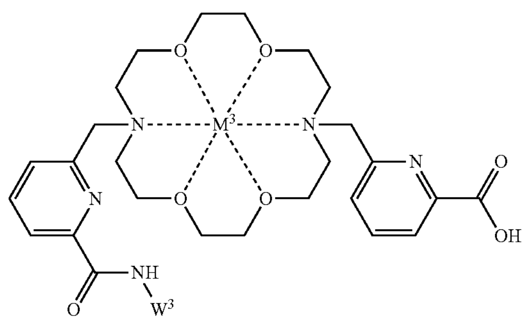

or a pharmaceutically acceptable salt thereof, wherein $M^3$ is an alpha-emitting radionuclide.

AW. The modified antibody, modified antibody fragment, or modified binding peptide of Paragraph AV, wherein $M^3$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AX. The modified antibody, modified antibody fragment, or modified binding peptide of any one of Paragraphs AM-AQ, wherein the compound of Formula IA is of Formula X (X)

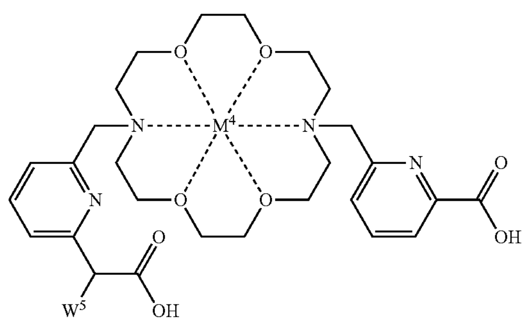

or a pharmaceutically acceptable salt thereof, wherein $M^4$ is an alpha-emitting radionuclide.

AY. The modified antibody, modified antibody fragment, or modified binding peptide of Paragraph AX, wherein $M^4$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

AZ. The modified antibody, modified antibody fragment, or modified binding peptide of any one of Paragraphs AM-AQ, wherein the compound of Formula IA is of Formula XIII (XIII)

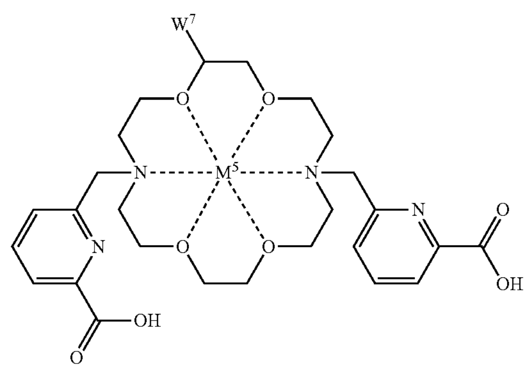

or a pharmaceutically acceptable salt thereof, wherein $M^5$ is an alpha-emitting radionuclide.

BA. The modified antibody, modified antibody fragment, or modified binding peptide of Paragraph AZ, wherein $M^5$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

BB. A composition comprising a pharmaceutically acceptable carrier and a compound of any one of Paragraphs A-R.

BC. A composition comprising a pharmaceutically acceptable carrier and a targeting compound of any one of Paragraphs S-AC or comprising a pharmaceutically acceptable carrier and a modified antibody, modified antibody fragment, or modified binding peptide of any one of Paragraphs AD-BA.

BD. A pharmaceutical composition useful in targeted radiotherapy of cancer and/or mammalian tissue over-expressing prostate specific membrane antigen ("PSMA") in a subject, wherein the pharmaceutical composition comprises a pharmaceutically acceptable carrier and a compound of any one of Paragraphs S-AC or a modified antibody, modified antibody fragment, or modified binding peptide of any one of Paragraphs AD-BA.

BE. The pharmaceutical composition of Paragraph BD, wherein the pharmaceutical composition comprises an effective amount for treating the cancer and/or mammalian tissue overexpressing PSMA of the compound or an effective amount for treating the cancer and/or mammalian tissue overexpressing PSMA of the modified antibody, modified antibody fragment, or modified binding peptide.

BF. The pharmaceutical composition of Paragraph BD or Paragraph BE, where the subject suffers from a mammalian tissue expressing a somatostatin receptor, a bombesin receptor, seprase, or a combination of any two or more thereof, and/or mammalian tissue overexpressing PSMA.

BG. The pharmaceutical composition of any one of Paragraphs BD-BF, wherein the subject suffers from one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, BH. The pharmaceutical composition of any one of Paragraphs BD-BG, wherein the subject suffers from one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer.

BI. The pharmaceutical composition of any one of Paragraphs BD-BH, wherein the pharmaceutical composition is formulated for intravenous administration, optionally comprising sterilized water, Ringer's solution, or an isotonic aqueous saline solution.

BJ. The pharmaceutical composition of any one of Paragraphs BD-BI, wherein the effective amount of the compound is from about 0.01 μg to about 10 mg of the compound per gram of the pharmaceutical composition.

BK. The pharmaceutical composition of any one of Paragraphs BD-BJ, wherein the pharmaceutical composition is provided in an injectable dosage form.

BL. A method of treating a subject, wherein the method comprises administering a targeting compound of any one of Paragraphs S-AC to the subject or administering a modified antibody, modified antibody fragment, or modified binding peptide of any one of Paragraphs AD-BA.

BM. The method of Paragraph BL, wherein the subject suffers from cancer and/or mammalian tissue overexpressing prostate specific membrane antigen ("PSMA")

BN. The method of Paragraph BM, wherein the method comprises administering an effective amount for treating the cancer and/or mammalian tissue overexpressing PSMA of the compound or an effective amount for treating the cancer and/or mammalian tissue overexpressing PSMA of the modified antibody, modified antibody fragment, or modified binding peptide BO. The method of any one of Paragraphs BL-BN, wherein the subject suffers from a mammalian tissue expressing a somatostatin receptor, a bombesin receptor, seprase, or a combination of any two or more thereof and/or mammalian tissue overexpressing prostate specific membrane antigen ("PSMA"), when administered to a subject.

BP. The method of any one of Paragraphs BL-BO, wherein the mammalian tissue comprises one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer.

BQ. The method of any one of Paragraphs BL-BP, wherein the subject suffers from one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer.

BR. The method of any one of Paragraphs BL-BQ, wherein the administering comprises parenteral administration.

BS. The method of any one of Paragraphs BL-BR, wherein the administering comprises intraveneous administration.

BT. The method of any one of Paragraphs BL-BS, wherein the effective amount is from about 0.1 μg to about 50 μg per kilogram of subject mass.

BU. A compound comprising a first domain having a blood-protein binding moiety with low specific affinity for the blood-protein, a second domain having a tumor targeting moiety with high affinity for a tumor antigen, and a third domain having a chelator.

BV. The compound of Paragraph BU, wherein the tumor antigen is PSMA, bombesin, somatostatin receptor, or seprase.

BW. The compound of Paragraph BU or Paragraph BV, wherein the blood protein binding moiety has specific affinity for albumin of about $0.5\text{-}50\times10^{-6}$ M, and the tumor targeting moiety has specific affinity for the tumor antigen of about $0.5\text{-}50\times10^{-9}$ M.

BX. A compound represented by the following structure

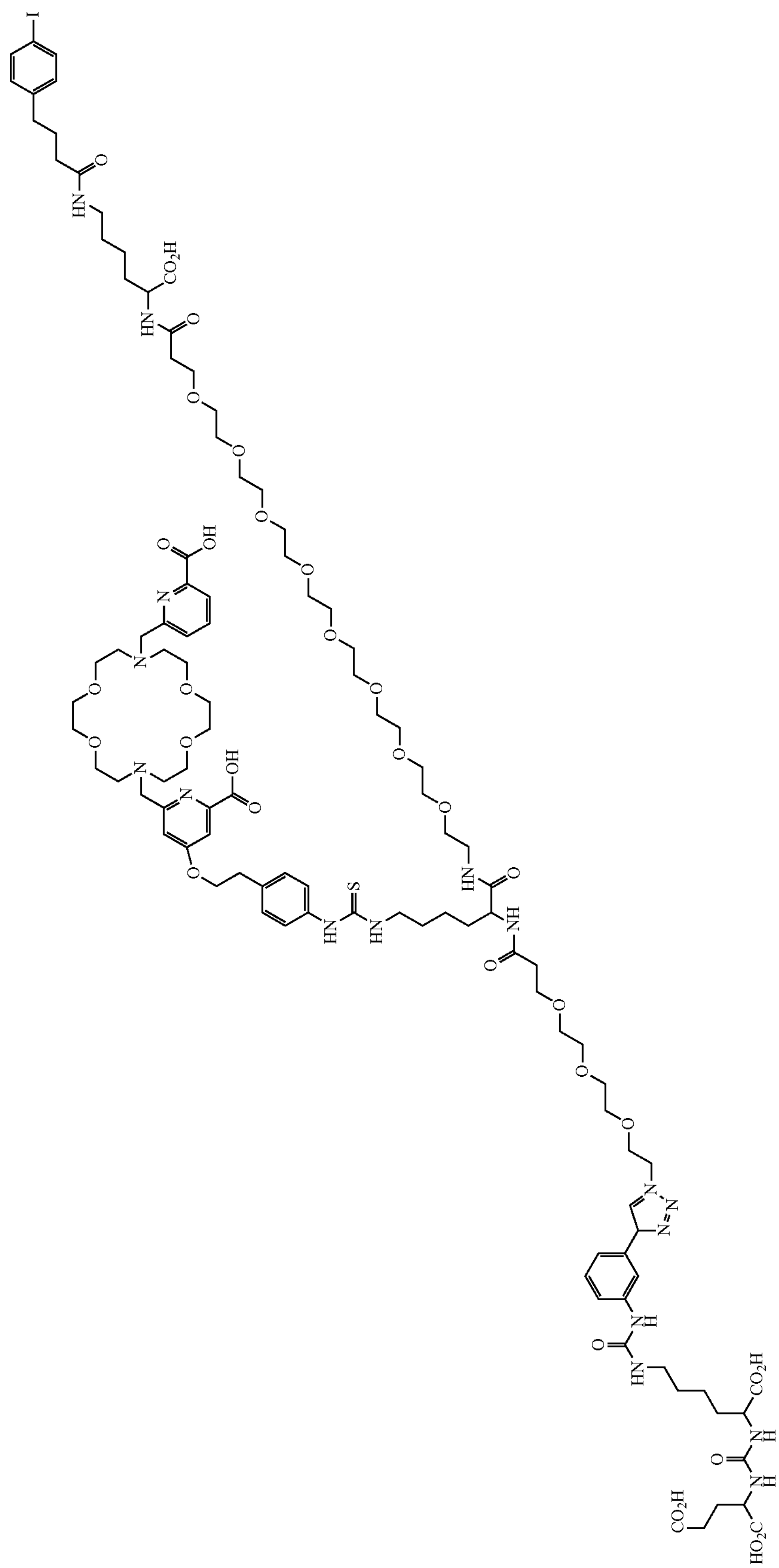

or a pharmaceutically acceptable salt thereof.

BY. A composition comprising the compound of Paragraph BX chelating $^{213}Bi^{3+}$, $^{211}At^{+}$, $^{225}Ac^{3+}$, $^{152}Dy^{3+}$, $^{212}Bi^{3+}$, $^{211}Bi^{3+}$, $^{217}At^{+}$, $^{227}Th^{4+}$, $^{226}Th^{4+}$, $^{233}Ra^{2+}$, $^{212}Pb^{2+}$, or $^{212}Pb^{4+}$.

BZ. A method of treating a subject, wherein the method comprises administering a composition of Paragraph BY to the subject.

CA. The method of Paragraph BZ, wherein the subject suffers from cancer and/or mammalian tissue overexpressing prostate specific membrane antigen ("PSMA")

CB. The method of Paragraph CA, wherein the method comprises administering an effective amount for treating the cancer and/or mammalian tissue overexpressing PSMA of the composition.

CC. The method of any one of Paragraphs BZ-CB, wherein the subject suffers from a mammalian tissue overexpressing prostate specific membrane antigen ("PSMA").

CD. The method of any one of Paragraphs BZ-CC, wherein the mammalian tissue comprises one or more of a growth hormone producing tumor, a neuroendocrine tumor, a pituitary tumor, a vasoactive intestinal peptide-secreting tumor, a small cell carcinoma of the lung, gastric cancer tissue, pancreatic cancer tissue, a neuroblastoma, and a metastatic cancer.

CE. The method of any one of Paragraphs BZ-CD, wherein the subject suffers from one or more of a glioma, a breast cancer, an adrenal cortical cancer, a cervical carcinoma, a vulvar carcinoma, an endometrial carcinoma, a primary ovarian carcinoma, a metastatic ovarian carcinoma, a non-small cell lung cancer, a small cell lung cancer, a bladder cancer, a colon cancer, a primary gastric adenocarcinoma, a primary colorectal adenocarcinoma, a renal cell carcinoma, and a prostate cancer.

CF. The method of any one of Paragraphs BZ-CE, wherein the administering comprises parenteral administration.

CG. The method of any one of Paragraphs BZ-CF, wherein the administering comprises intraveneous administration.

CH. The method of any one of Paragraphs BZ-CG, wherein the effective amount is from about 0.1 μg to about 50 μg per kilogram of subject mass.

Other embodiments are set forth in the following claims, along with the full scope of equivalents to which such claims are entitled.

What is claimed is:

1. A modified antibody, modified antibody fragment, or modified binding peptide comprising a linkage arising from conjugation of a compound of Formula I or Formula IA (I)

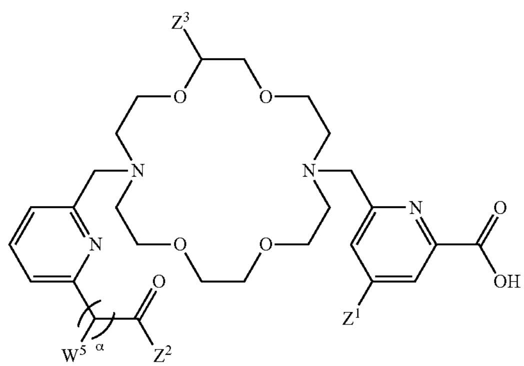

-continued (IA)

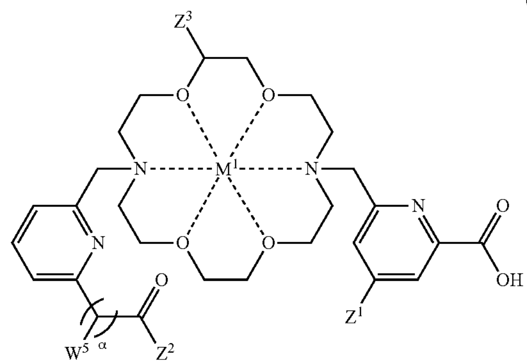

or a pharmaceutically acceptable salt thereof, with an antibody, antibody fragment, or binding peptide, wherein $M^1$ is an alpha-emitting radionuclide;

$Z^1$ is H or —$X^1$—$W^2$;

$Z^2$ is OH or NH—$W^3$;

$Z^3$ is H or $W^7$;

wherein at least one of $Z^1$ and $Z^3$ is not H or $Z^2$ is not OH and comprises the linkage arising from the conjugation of the compound of Formula I or Formula IA with the antibody, antibody fragment, or binding peptide;

α is 0 or 1;

$X^1$ is O, NH, or S;

$W^2$ and $W^3$ are each independently H, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)_y—R'$ where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group;

$W^5$ and $W^7$ are each independently OH, $NH_2$, SH, alkyl, cycloalkyl, alkenyl, cycloalkenyl, alkynyl, aryl, heterocyclyl, heteroaryl, $—CH_2CH_2—(OCH_2CH_2)_w—R'$ where w is 1, 2, 3, 4, 5, 6, 7, 8, 9, or 10, or $—CH_2CH_2—(OCH_2CH_2)_x—OR'$ where x is 1, 2, 3, 4, 5, 6, 7, 8, 9, or 10, each of which may optionally be substituted with one or more of halo, $—N_3$, —OR', $—CH_2CH_2—(OCH_2CH_2)y_x$-R' where y is 1, 2, 3, 4, 5, 6, 7, 8, 9, or 10, $—CH_2CH_2—(OCH_2CH_2)_z—OR'$ where z is 1, 2, 3, 4, 5, 6, 7, 8, 9, or 10, —SR', —OC(O)R', —C(O)OR', —C(S)OR', —S(O)R', $—SO_2R'$, $—SO_2(OR')$, $—SO_2NR'_2$, $—P(O)(OR')_2$, —P(O)R'(OR'), $—P(O)R'_2$, —CN, —OCN, —SCN, —NCO, —NCS, $—NR'—NH_2$, —N═C═N—R', $—SO_2Cl$, —C(O)Cl, or an epoxide group; and R' is independently at each occurrence H, halo, $—N_3$, $C_1$-$C_6$ alkyl, $C_3$-$C_6$ cycloalkyl, $C_2$-$C_6$ alkenyl, $C_5$-$C_8$ cycloalkenyl, $C_2$-$C_6$ alkynyl, $C_8$-$C_{10}$ cycloalkynyl, $C_5$-$C_6$ aryl, heterocyclyl, or heteroaryl.

2. The modified antibody, modified antibody fragment, or modified binding peptide of claim 1, wherein $M^1$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

3. The modified antibody, modified antibody fragment, or modified binding peptide of claim 1, wherein the antibody comprises belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

4. The modified antibody, modified antibody fragment, or modified binding peptide of claim 1, wherein the antibody fragment comprises an antigen-binding fragment of belimumab, Mogamulizumab, Blinatumomab, Ibritumomab tiuxetan, Obinutuzumab, Ofatumumab, Rituximab, Inotuzumab ozogamicin, Moxetumomab pasudotox, Brentuximab vedotin, Daratumumab, Ipilimumab, Cetuximab, Necitumumab, Panitumumab, Dinutuximab, Pertuzumab, Trastuzumab, Trastuzumab emtansine, Siltuximab, Cemiplimab, Nivolumab, Pembrolizumab, Olaratumab, Atezolizumab, Avelumab, Durvalumab, Capromab pendetide, Elotuzumab, Denosumab, Ziv-aflibercept, Bevacizumab, Ramucirumab, Tositumomab, Gemtuzumab ozogamicin, Alemtuzumab, Cixutumumab, Girentuximab, Nimotuzumab, Catumaxomab, or Etaracizumab.

5. The modified antibody, modified antibody fragment, or modified binding peptide of claim 1, wherein the binding peptide comprises a prostate specific membrane antigen ("PSMA") binding peptide, a somatostatin receptor agonist, a bombesin receptor agonist, a seprase binding compound, or a binding fragment thereof.

6. The modified antibody, modified antibody fragment, or modified binding peptide of claim 1, wherein the compound is of Formula III or a pharmaceutically acceptable salt thereof or the compound is Formula IV or a pharmaceutically acceptable salt thereof (III)

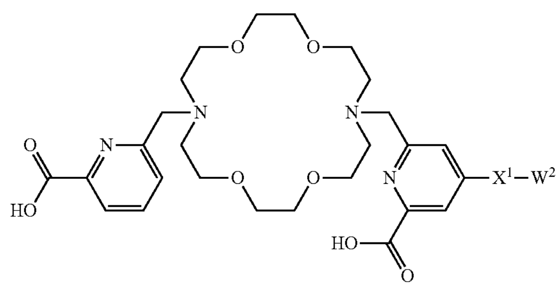

-continued (IV)

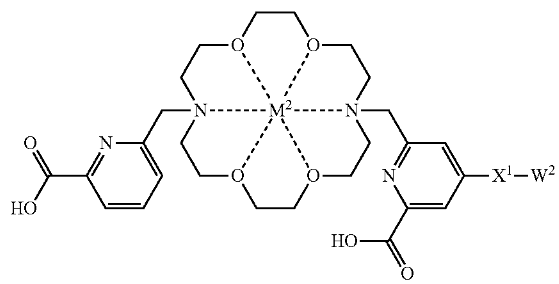

wherein $M^2$ is an alpha-emitting radionuclide.

7. The modified antibody, modified antibody fragment, or modified binding peptide of claim 6, wherein the compound is of Formula IV and wherein $M^2$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

8. The modified antibody, modified antibody fragment, or modified binding peptide of claim 1, wherein the compound is of Formula VI or a pharmaceutically acceptable salt thereof or the compound is of Formula VII or a pharmaceutically acceptable salt thereof (VI)

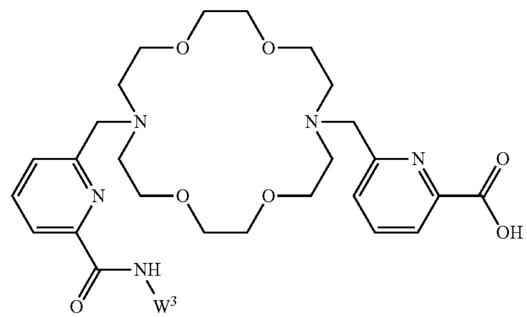

(VII)

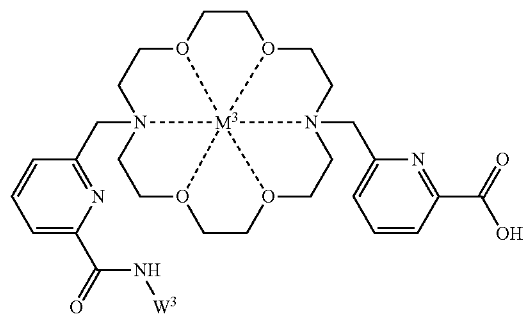

wherein $M^3$ is an alpha-emitting radionuclide.

9. The modified antibody, modified antibody fragment, or modified binding peptide of claim 8, wherein the compound is of Formula VII and wherein $M^3$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

10. The modified antibody, modified antibody fragment, or modified binding peptide of claim 1, wherein the compound is of Formula IX or a pharmaceutically acceptable salt thereof or the compound is of Formula X or a pharmaceutically acceptable salt thereof (IX)

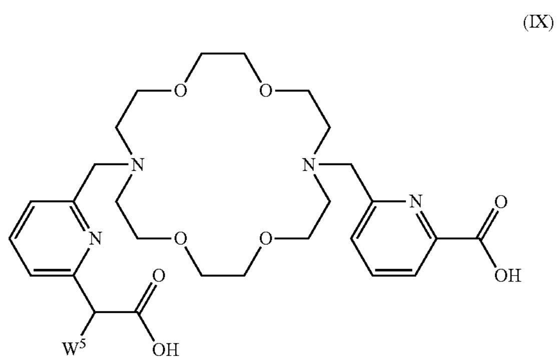

(X)

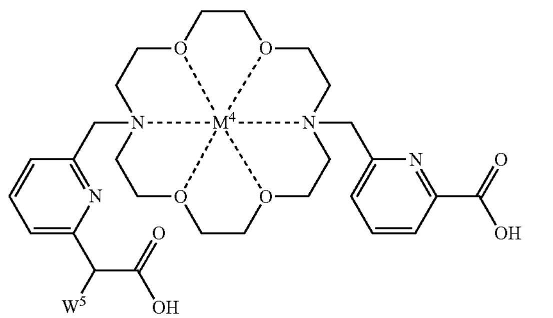

wherein $M^4$ is an alpha-emitting radionuclide.

11. The modified antibody, modified antibody fragment, or modified binding peptide of claim 10, wherein the compound is of Formula X and wherein $M^4$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

12. The modified antibody, modified antibody fragment, or modified binding peptide of claim 1, wherein the compound of Formula XII or a pharmaceutically acceptable salt thereof or the compound is of Formula XIII or a pharmaceutically acceptable salt thereof (XII)

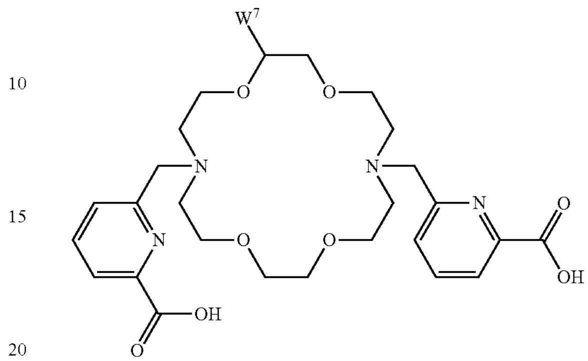

(XIII)

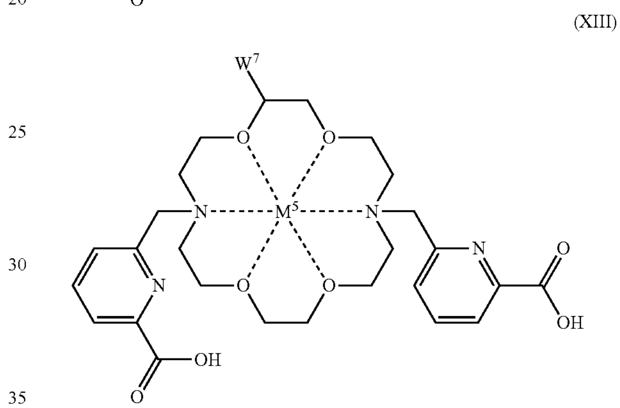

wherein $M^5$ is an alpha-emitting radionuclide.

13. The modified antibody, modified antibody fragment, or modified binding peptide of claim 12, wherein $M^5$ is actinium-225 ($^{225}Ac^{3+}$), radium-223 ($^{233}Ra^{2+}$), bismuth-213 ($^{213}Bi^{3+}$), lead-212 ($^{212}Pb^{2+}$ and/or $^{212}Pb^{4+}$), terbium-149 ($^{149}Tb^{3+}$), fermium-255 ($^{255}Fm^{3+}$), thorium-227 ($^{227}Th^{4+}$), thorium-226 ($^{226}Th^{4+}$), astatine-211 ($^{211}At^{+}$), astatine-217 ($^{217}At^{+}$), or uranium-230.

* * * * *